United States Patent
Englehart et al.

(10) Patent No.: US 12,159,699 B2
(45) Date of Patent: Dec. 3, 2024

(54) SYSTEMS AND METHODS FOR NODE GRAPH STORAGE FOR STORING PATIENT DATA ACROSS CLINICS

(71) Applicant: Michigan Health Information Network Shared Services, East Lansing, MI (US)

(72) Inventors: Matthew Englehart, Holland, MI (US); Timothy Allen Pletcher, Petoskey, MI (US)

(73) Assignee: MICHIGAN HEALTH INFORMATION NETWORK SHARED SERVICES, East Lansing, MI (US)

(*) Notice: Subject to any disclaimer, the term of this patent is extended or adjusted under 35 U.S.C. 154(b) by 89 days.

(21) Appl. No.: 18/199,002

(22) Filed: May 18, 2023

(65) Prior Publication Data

US 2023/0395211 A1 Dec. 7, 2023

Related U.S. Application Data

(60) Provisional application No. 63/348,751, filed on Jun. 3, 2022.

(51) Int. Cl.
*G16H 10/60* (2018.01)
*G06F 40/295* (2020.01)

(52) U.S. Cl.
CPC .......... *G16H 10/60* (2018.01); *G06F 40/295* (2020.01)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS 10,586,622 B2    3/2020  Livesay et al.
11,158,406 B2 *  10/2021  Lyman ................. G06V 10/225
(Continued)

OTHER PUBLICATIONS

Reese et al. 2020, "KG-COVID-19: a framework to produce customized knowledge graphs for COVID-19 response," bioRxiv [Preprint]. Aug. 1, 20208:2020.08.17.254839. doi: 10.1101/2020.08.17.254839. Update in: Patterns (N Y). Nov. 9, 2020;:100155. PMID: 32839776; PMCID: PMC7444288.*
(Continued)

*Primary Examiner* — Robert W Morgan
*Assistant Examiner* — Charles P Coleman
(74) *Attorney, Agent, or Firm* — Foley & Lardner LLP

(57) ABSTRACT

A method for prioritized updating of a node graph data structure includes storing a node graph comprising a plurality of patient nodes and a plurality of attribute nodes; receiving, by the one or more processors, a set of data from one or more data sources, each of the one or more data sources corresponding to a different clinic visited by one or more patients represented in the node graph; inserting a first piece of data regarding a first patient having a first patient node in the node graph into a first queue and a second piece of data regarding a second patient having a second patient node in the node graph into a second queue; and updating the node graph with the first piece of data prior to updating the node graph with the second piece of data.

20 Claims, 38 Drawing Sheets

(58) Field of Classification Search
CPC ........ G16H 20/13; G16H 20/17; G16H 30/00; G16H 40/00; G16H 50/00; G16H 70/00; G16H 10/60; G06Q 50/22–24; G06F 40/295
USPC .................................................. 705/3, 2, 20
See application file for complete search history.

(56) References Cited

U.S. PATENT DOCUMENTS

| | | | |
|---|---|---|---|
| 2018/0240536 A1 | 8/2018 | Bostic et al. | |
| 2019/0362452 A1* | 11/2019 | Brunets | H04L 43/067 |
| 2019/0363958 A1* | 11/2019 | Brunets | G06F 11/3024 |
| 2019/0363959 A1* | 11/2019 | Rice | H04L 67/306 |
| 2019/0364009 A1* | 11/2019 | Joseph | G06F 40/237 |
| 2019/0364117 A1* | 11/2019 | Rogynskyy | G06F 16/9535 |
| 2019/0364130 A1* | 11/2019 | Rogynskyy | H04M 15/60 |
| 2020/0160942 A1* | 5/2020 | Lyman | G06V 30/19173 |
| 2020/0357507 A1 | 11/2020 | Blalock et al. | |
| 2020/0379885 A1* | 12/2020 | Englehart | G06F 21/53 |
| 2021/0064542 A1* | 3/2021 | Jang | G06F 12/0246 |
| 2021/0090694 A1* | 3/2021 | Colley | G16B 40/00 |
| 2021/0183485 A1* | 6/2021 | Yao | G06V 10/764 |
| 2022/0020458 A1* | 1/2022 | Francois | G16H 10/60 |
| 2022/0156934 A1* | 5/2022 | Lyman | G16H 15/00 |
| 2022/0164337 A1* | 5/2022 | Korpman | G06F 16/9577 |

OTHER PUBLICATIONS

Xu et al. 2021, "Predictive Modeling of Clinical Events with Mutual Enhancement Between Longitudinal Patient Records and Medical Knowledge Graph," 2021 IEEE International Conference on Data Mining (ICDM), Auckland, New Zealand, 2021, pp. 777-786, doi: 10.1109/ICDM51629.2021.00089.*

* cited by examiner

's health.

SYSTEMS AND METHODS FOR NODE GRAPH STORAGE FOR STORING PATIENT DATA ACROSS CLINICS

CROSS-REFERENCE TO RELATED APPLICATIONS

This application claims the benefit of priority to U.S. Provisional Application No. 63/348,751, filed Jun. 3, 2022.

BACKGROUND OF THE DISCLOSURE

Storing patient data for patients in different clinics of a healthcare system is a historically analog process performed by physicians and administrators at the individual clinics. When patients visit the clinics to receive care, the patients may often visit individual clinics to seek an opinion and then never return or seek additional opinions at other clinics. Each clinic may store data generated from such a visit in a local database. Because the data is often not dispersed to other clinics, clinicians at the other clinics may often perform repetitive tests or not have a complete data set about the patients when giving diagnoses. Any attempt to store data in a common database may result in a database with an exceedingly large number of entries that only increases in size as patients continue to visit clinics for care. Accordingly, it can be difficult for a processor to sort and/or retrieve meaningful data about individuals in real-time when the individuals visit the clinics for treatment. Such retrieval may be difficult because the processor may have to query the databases for each entry that relates to the treatment of the patient.

SUMMARY OF THE DISCLOSURE

A computer implementing the systems and methods discussed herein may overcome the aforementioned technical deficiencies by providing a node graph data structure. For example, computers at different clinics may transmit data to a remote computing device that stores such a node graph data structure. The node graph data structure may include a web of data for different clinics, patients, attributes, locations, events, demographics, diagnoses, file types, quality scores, and any other type of data that relates to patient care. The data may be stored as nodes (e.g., data structures that include string identifiers of the patients and/or attributes) in the node graph. Nodes that are related to each other (e.g., data identifying a patient's name may be related to the patient's date of birth and/or a clinic the patient visited) may be linked to each other through edges that are connected to the related nodes. The remote computing device may receive such data from computers located at different clinics and aggregate the data into a single node graph data structure that does not store repetitive data for clinic visits made by the same patient. For instance, in the node graph data structure, a person's name would take up the same amount of memory as one item of data regardless of the number of visits the patient made to clinics. In systems not implementing the systems and methods described herein, the person's name would take up memory in a standard database separately for each visit because each visit may have its own entry in the database. Accordingly, the node graph data structure may require significantly fewer memory resources to store the data and require less time to retrieve the data. Thus, when a patient visits a clinic for a new visit, the remote computing device may quickly retrieve data about the patient from previous visits to other clinics to provide the clinic with a holistic view of the patient's health.

In one example of faster data retrieval, the computer implementing the systems and methods described herein may use the edges between nodes identified in a query to retrieve data for the query. For instance, upon receiving a request from a computer for data about a particular patient, the computer storing the node graph data structure may query the node graph data structure for a node containing the name of the patient. Upon identifying such a node, the computer may stop querying the node graph data structure because only one node containing the patient's name may be stored in the node graph. The computer may then identify the edges that connect the patient's node to attribute nodes indicating attributes of the patient. The computer may identify the attributes associated with nodes that are connected to the patient's node and generate a list of attributes of the patient from the identified attributes. The computer may generate and transmit a record containing the list of attributes to the requesting computing device. Thus, the computer may use substantially fewer computing resources to retrieve data from the node graph upon receipt of a request than computers in conventional systems, which would continuously search a database or set of databases (e.g., databases local to individual clinics) for each entry that contains the patient's name.

In another example of faster data retrieval, the computer implementing the systems and methods described herein may use the edges between nodes to identify a population of patients that have a common set of attributes. For instance, the computer may receive a request identifying multiple attributes. Upon receiving the request, the computer may request the node graph data structure for each of the attributes. The computer may identify the attribute nodes from the node graph data structure and then identify the edges to patient nodes from the attribute nodes. The computer may identify the patient nodes that have edges with each of the attribute nodes identified from the request and generate and transmit a record back to the requesting computing device with the list of patients that have edges with the attributes identified in the request. In this way, the computer may use the node graph data structure to quickly retrieve population lists of patients that meet requested criteria without querying an entire database for entries that contain such data.

One technical problem that arises when storing data from multiple clinics is the clinics may transmit data to the remote computer faster than the computer can add the data to the node graph. This problem can make using the system difficult for clinicians because certain types of data (e.g., protected health information (PHI)) and/or data from different sources may be more important for clinicians to make a diagnosis and therefore need to be available quickly upon upload to the remote computer. The more important data may be uploaded at the same time as other less important data, however, so there may be significant latency between the time the data is uploaded from the clinic to the computer and the time the data is added to the node graph. For example, the computer hosting the node graph may collect a variety of types of data about patients from different clinics such as the patients' demographic data (e.g., address and hair color) and PHI (e.g., a diagnosis or vital signs). Because the node graph may be generated to create a shared network to enable clinicians to quickly retrieve information about their patients, it can be important for clinicians to know if another clinician at the same or a different clinic diagnosed a patient with a disease or identified some other protected health information to aid in diagnosing the patient. Demographic information may not be as important to clinicians because it generally does not affect a diagnosis. However, given that the node graph may receive thousands of data files about patients each day, the important protected health information may enter into the same upload queue as the demographic information when the remote computer updates the data structure with incoming data. There is a need to prioritize protected health information when updating the node graph so clinics can have the information available in real-time instead of waiting as the system updates the data structure with less important demographic data.

A computer implementing the systems and methods described herein may solve the aforementioned technical problem by inserting data the computer receives into prioritized queues. A computer may insert the data into the prioritized queues based on the type, source, document type, or any other criteria of the data. The computer may retrieve the data from the queues based on the priority of the queues. The computer may then upload the data into the node graph data structure, thus ensuring the data can be available for retrieval by clinicians at other clinics in which the data did not originate in real-time. This provides improved computer functionality because the computer can prioritize uploading data to the data structure that needs to be available to clinicians quickly. The computer may upload the less time-sensitive data after the computer has uploaded data from the higher priority queue. Accordingly, the computer may upload the high-priority data with lower latency while still uploading all of the data the computer receives. Thus, the computer may use less processing power and memory when updating its stored data structure with data from different clinics while still enabling the system to make high-priority data available to clinicians in real-time.

Another technical problem that arises when storing data from multiple clinics in a node graph without data entries is that it can be difficult to maintain a history of the relationships between patients and attributes over time. A node graph that only uses identifications of patients and attributes and edges between the nodes for the patients and attributes may use a weighting system that indicates how strong the relationship is between the patient's names and their attributes (e.g., the likelihood that the patients have the attribute). While a weight may change over time, the changing weight may only provide a snapshot of the relationship between the patient and the attribute at the current time and does not indicate how the relationship changed over time or the strength of the relationship during previous time periods. Thus, the node graph may only store a current strength of the relationship between patients and attributes, inhibiting clinicians' ability to search patients' medical history and otherwise query the node graph for data about the patients from different time periods.

A computer implementing the systems and methods described herein may overcome the aforementioned technical deficiencies by generating multiple edges between the patient nodes and the attribute nodes. Each edge between a patient node and an attribute node may have its own weight and correspond to data the computer received during a specific time period. For example, the computer may store edges between a patient node and a medical diagnosis node for individual months of a year-long period. The computer may receive data from different clinics indicating the patient was undergoing treatment to overcome the medical diagnosis for six months until the patient was cured of the diagnosis. The computer may receive data from each visit to a clinic for such treatment and adjust the weight for the edges based on the months in which the computer received the data or the months in which the patient visited the clinics. Accordingly, the weights for the six-month period may vary between the months until the patient stopped visiting clinics for the treatment, causing the weights for each of the next six months to be zero or null or for there not to be any edges for the six-month period. Therefore, upon receiving a query for attributes about a patient for a certain time period, the system can evaluate the score for the edge that corresponds to the time period to determine whether to retrieve indications of the attributes. In this way, the computer may store a history of patient treatment using a node graph data structure without using the memory resources that would be required to store individual entries for every patient visit to a clinic.

Another technical problem that arises when storing data from multiple clinics in a node graph without data entries is that there may be various degrees of accuracy for the data depending on the clinics from which the data is received. For example, if a clinic provides data that is used to update the node graph during a time period, but the clinic is not currently treating the patient during the time period, the data may be unreliable because the data may be stale or may pertain to a different patient (e.g., an error at the clinic may cause the clinic to include the wrong patient name on an uploaded document). Accordingly, the node graph may need to be structured to account for these periods of unreliability.

A computer implementing the systems and methods described herein may overcome the aforementioned technical problem by generating a relationship status node within the node graph. The relationship status node may contain a history of care statuses between a patient and a particular clinic. The relationship status node may include indications of time periods in which a patient is received or is currently receiving care from the clinic. For instance, the node graph may store an edge between a patient node and a relationship status node and another edge between the relationship status node and a node identifying a clinic. The computer can dynamically update the relationship status node as the computer receives data indicating the patient is or is not under active care with the clinic. Accordingly, upon receiving a request for data about a patient from the clinic, the computer may identify time periods in which the patient was not under active care with the clinic and not retrieve any data that is associated with the time periods. Thus, the computer may use the node graph to avoid retrieving stale or inaccurate data in response to a request.

In one aspect, the present disclosure describes a method for prioritized updating of a data structure. The method may include receiving, by a processor, a set of data from one or more data sources; selecting, by the processor, a first queue for a first piece of data of the set of data based on the first piece of data including a first type of information and a second queue for a second piece of data of the set of data based the second piece of data including a second type of information; inserting, by the processor, the first piece of data into the first queue and the second piece of data into the second queue; retrieving, by the processor, the first piece of data from the first queue prior to retrieving the second piece of data from the second queue responsive to determining a stored condition indicating to retrieve a piece of data from the first queue prior to retrieving a piece of data from the second queue is satisfied; and updating, by the processor, a data structure with the retrieved first piece of data from the first queue.

In another aspect, the present disclosure describes a method for updating a node graph. The method may include storing, by a processor, a node graph including a plurality of entity nodes and a plurality of attribute nodes, each entity node of the plurality of entity nodes associated with a different entity and each attribute node of the plurality of attribute nodes associated with a different attribute; receiving, by the processor from a data source during a plurality of time periods, a plurality of data files including data for a first entity; identifying, by the processor, a plurality of edges between a first entity node of the plurality of entity nodes that identifies the first entity and an attribute node of the plurality of attribute nodes that identifies a first attribute of the first entity, each of the plurality of edges corresponding to a value and a different time period of the plurality of time periods; and for each of the plurality of data files, updating, by the processor, a value for an edge that corresponds to a time period associated with the data file.

In another aspect, the present disclosure describes a method for data storage and retrieval. The method may include storing, by a processor, a node graph including a plurality of entity nodes and a plurality of attribute nodes, each entity node of the plurality of entity nodes associated with a different entity and each attribute node of the plurality of attribute nodes associated with a different attribute; receiving, by the processor from a client device, a request for data including a plurality of identifications of a plurality of attributes; identifying, by the processor, a set of attribute nodes responsive to each attribute node of the set of attribute nodes having a matching identifier to an identification of the plurality of identifications; selecting, by the processor, a set of entity nodes associated with a set of entities responsive to determining each entity node of the set has an edge with each of the set of attribute nodes; and transmitting, by the processor, a record identifying the set of entities to the client device.

In another aspect, the present disclosure describes a method for data storage and retrieval. The method may include storing, by a processor, a node graph including a plurality of entity nodes and a plurality of attribute nodes, each entity node of the plurality of entity nodes associated with a different entity and each attribute node of the plurality of attribute nodes associated with a different attribute; receiving, by the processor from a client device, a request for data including an identification of a first entity; identifying, by the processor, an entity node associated with the first entity based on the identification; selecting, by the processor, a set of attribute nodes associated with a set of attributes responsive to determining each attribute node of the set of attribute nodes has an edge with the entity node; and transmitting, by the processor, a record identifying the set of attributes to the client device.

In yet another aspect, the present disclosure describes a method for data storage and retrieval. The method may include storing, by a processor, a node graph including a plurality of entity nodes and a plurality of group entity nodes, each entity node of the plurality of entity nodes associated with a different entity and each group entity node of the plurality of group entity nodes associated with a different group entity; linking, by the processor, an entity node of the plurality of entity nodes with a group entity node of the plurality of group entity nodes through a relationship status node, the relationship status node having an inactive status indicating an entity associated with the entity node is currently not receiving clinical care from a group entity associated with the group entity node; receiving, by the processor from a data source corresponding to the group entity, a data file including data identifying the entity; and adding, by the processor, a string including an active status to the relationship status node responsive to the data file including the data identifying the entity.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

The details of various embodiments of the methods and systems are set forth in the accompanying drawings and the description below.

DETAILED DESCRIPTION

For purposes of reading the description of the various embodiments below, the following descriptions of the sections of the specification and their respective contents may be helpful:

Section A describes embodiments of systems and methods for clinical node graph data structure storage; and Section B describes a computing environment which may be useful for practicing embodiments described herein.

A. Systems and Methods for Clinic Node Graph Data Structure Storage

As mentioned above, storing patient data for patients in different clinics of a healthcare system is a historically analog process performed by physicians and administrators at the individual clinics. When patients visit the clinics to receive care, the patients may often visit individual clinics to seek an opinion and then never return or they may seek additional opinions at other clinics. Each clinic may store data generated from such a visit in a local database. When doing so, the clinics often create individual entries for each visit, despite many visits being performed by the same patients over and over again. The different entries often contain repetitive data between each other (e.g., each entry for the same patient may have the same data for the patient's name, address, demographic information, and contact information), causing the databases storing the entries to require a large amount of memory to store the data. Further, because each clinic generally has its own local database, it can be difficult for a computer to query the clinic databases for data about particular patients because each database query would require a separate message transmission and for the computer that receives the query to search through a large number of entries in the computer's local data structure. Accordingly, storing and retrieving data for patients as they visit different clinics can require a large amount of memory resources and processing power by both the querying computer and the computers at the clinics that store the data.

Figure 1:
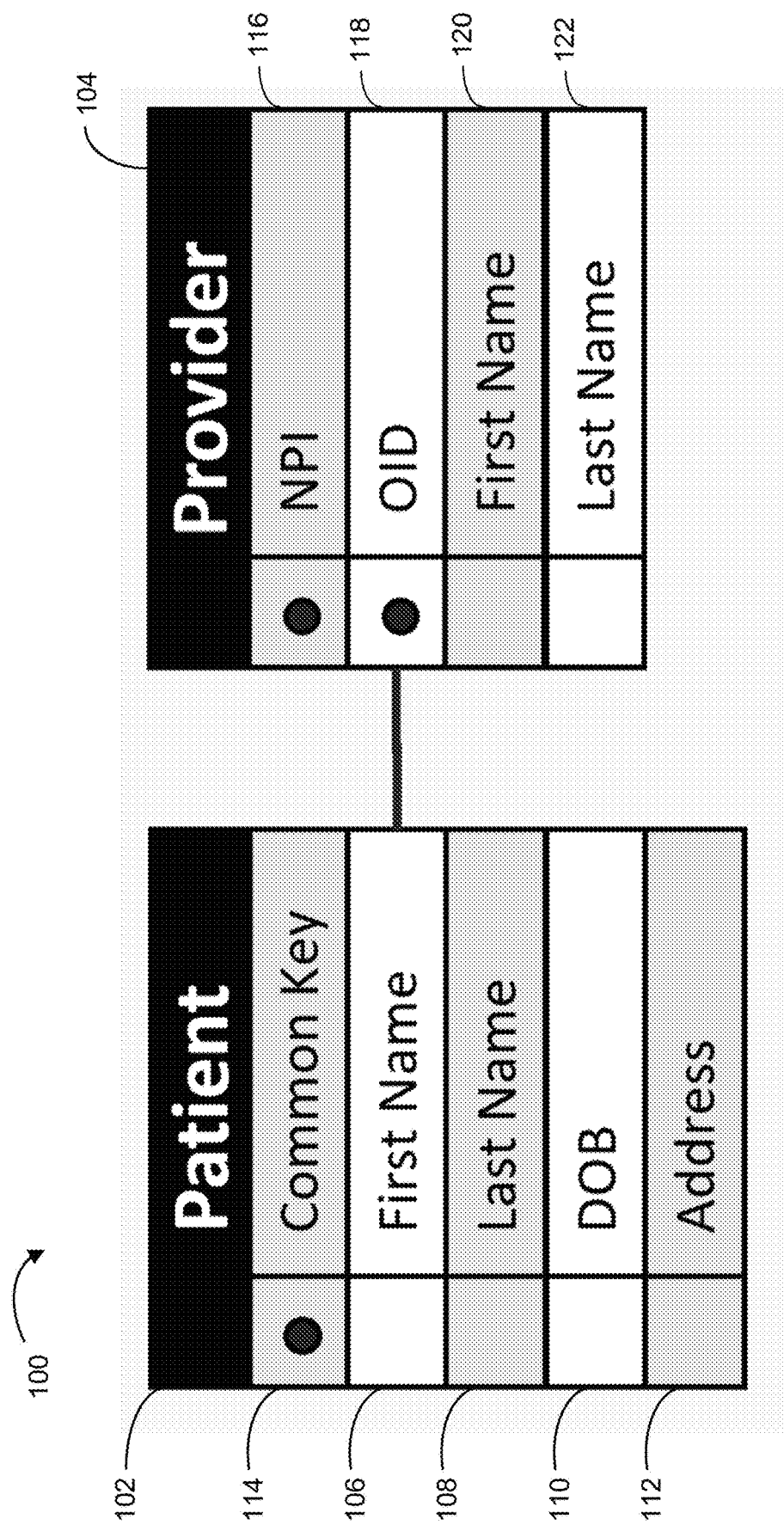
FIG. 1 is an illustration of an entry in a database that stores data about a patient receiving treatment from a particular clinic.

In one example of a solution to storing patient data for different clinics (e.g., healthcare providers) in a single database, FIG. 1 illustrates an example database 100 that includes individual entries for different patients that stores entries for different clinics. A computer not implementing the systems and methods described herein may store database 100 in memory. Database 100 may be a relational database that includes entries for each visit by patients to the different clinics and that includes separate attributes for the patients in the entries. For example, database 100 may include a patient entry 102 and a provider entry 104. Patient entry 102 may be an entry in database 100 that includes data about a particular patient and provider entry 104 may be an entry in database 100 that includes data about a particular clinic and patients that have visited the clinic. Patient entry 102 may include rows in database 100 that include data for particular attributes of the patient, such as a first name row 106, a last name row 108, a date of birth row 110, and an address row 112. Each of rows 106-112 may include a separate string of data about the patient. Patient entry 102 may also include a common key row 114 that connects patient entry 102 to different provider entries, such as provider entry 104 (e.g., the value in common key row 114 may match a value in provider entry 104). The connection may indicate the patient received care at the clinic. Provider entry 104 may include a national provider identifier row 116, an object identification number row 118, a first name row 120, and a last name row 122. Patient entry 102 and provider entry 104 may be linked because the value in common key row 114 may match the value in a corresponding common key row of provider entry 104 (not shown). The link may indicate that the patient received care at the clinic.

To store and retrieve data for patients and providers in database 100, a computer may have to use a significant amount of computer resources. For example, because each patient and clinic is associated with an individual entry and set of attributes, there can be a significant amount of overlap between attributes that patients share with each other (e.g., diagnoses, addresses, demographic attributes such as eye color, etc.) and with clinics. For example, as illustrated in FIG. 1, a patient may have an entry in database 100 that includes the patient's first name and last name. The patient's first name and last name may also be listed in an entry for a clinic indicating the patient visited the clinic. If the patient visited multiple clinics over a long time period, the patient's demographic and diagnostic information is likely in the entries for each clinic, causing the computer that stores database 100 to store a significant amount of repetitive data for the patient. Because the computer that stores database 100 may store data for hundreds of thousands of patients and thousands of clinics, the memory required to store data in this manner can be large.

Implementations of the systems and methods described herein overcome the aforementioned technical deficiencies by implementing a node graph data structure. For example, referring now to FIG. 2, a computer may store a node graph data structure 200. Node graph data structure 200 may include a patient node 202 and attribute nodes 204-216. Patient node 202 may include a string identification of a patient for which node graph data structure 200 stores data. Attribute nodes 204-216 may include attributes of the patient and may include a state attribute node 204, a zip code attribute node 206, a provider attribute node 208, a consent attribute node 210, a provider attribute node 212, a gap-in-care attribute node 214, and a payer attribute node 216. The patient associated with patient node 202 may have some form of relationship with each of the attributes of attribute nodes 204-216 which may be represented by the edges between patient node 202 and attribute nodes 204-216. Each of nodes 202-216 may only store data identifying the respective patient and attribute of the nodes. Patient node 202 may have edges with any number of attribute nodes and/or attribute nodes 204-216. The attribute nodes may have edges with any number of patient nodes. Other examples of nodes in node graph data structure 200 are nodes that indicate a patient's diagnosis, age bracket or age, gender, skin color, weight or weight bracket, etc. By storing patient data in a node graph data structure in this manner, node graph data structure 200 may store single instances of attribute identifications while indicating that multiple patients have the same attributes, thus minimizing the amount of data that is required to store such data.

Figure 2:
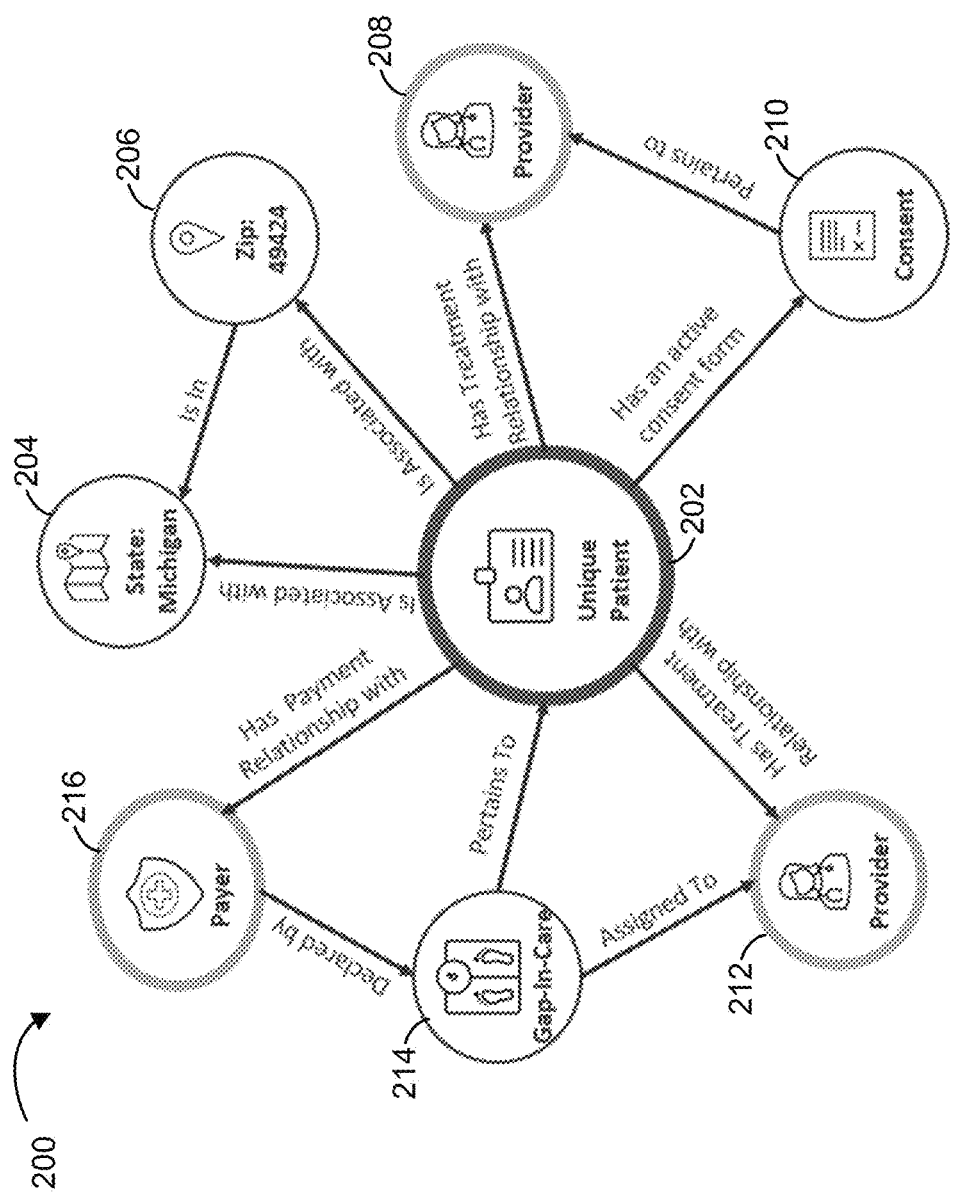
FIG. 2 is an illustration of an example node graph data structure that stores data for a patient and attributes of the patient in separate nodes and edges between the nodes, in accordance with some embodiments.

As illustrated in FIG. 2, the edges between patient node 202 and attribute nodes 204-216 may store data structures that include identifications of the types of relationships the patient associated with patient node 202 has with different attributes. For example, the patient may live in Michigan at an address with a 49424 zip code. Accordingly, the edge between patient node 202 and zip code attribute node 206 may have a string identifier indicating the patient "is associated with" zip code 49242 and the edge between patient node 202 and state attribute node 204 may have a string identifier indicating the patient "is associated with" the state of Michigan. An edge between state attribute node 204 and zip code attribute node 206 may have an "is in" identification that indicates the zip code 49424 is in Michigan. Patient node 202 and attribute nodes 208-216 may be similarly linked to each other through relationships such as "has treatment relationship with", "pertains to," "has an active consent form," "assigned to," "has payment relationship with," "declared by," etc. Such relationship information may be stored in individual data structures that are dedicated to storing information for individual edges in the node graph data structure. In this way, node graph data structure 200 may indicate the different relationships the patient has with attributes and what the relationships are.

Figure 3:
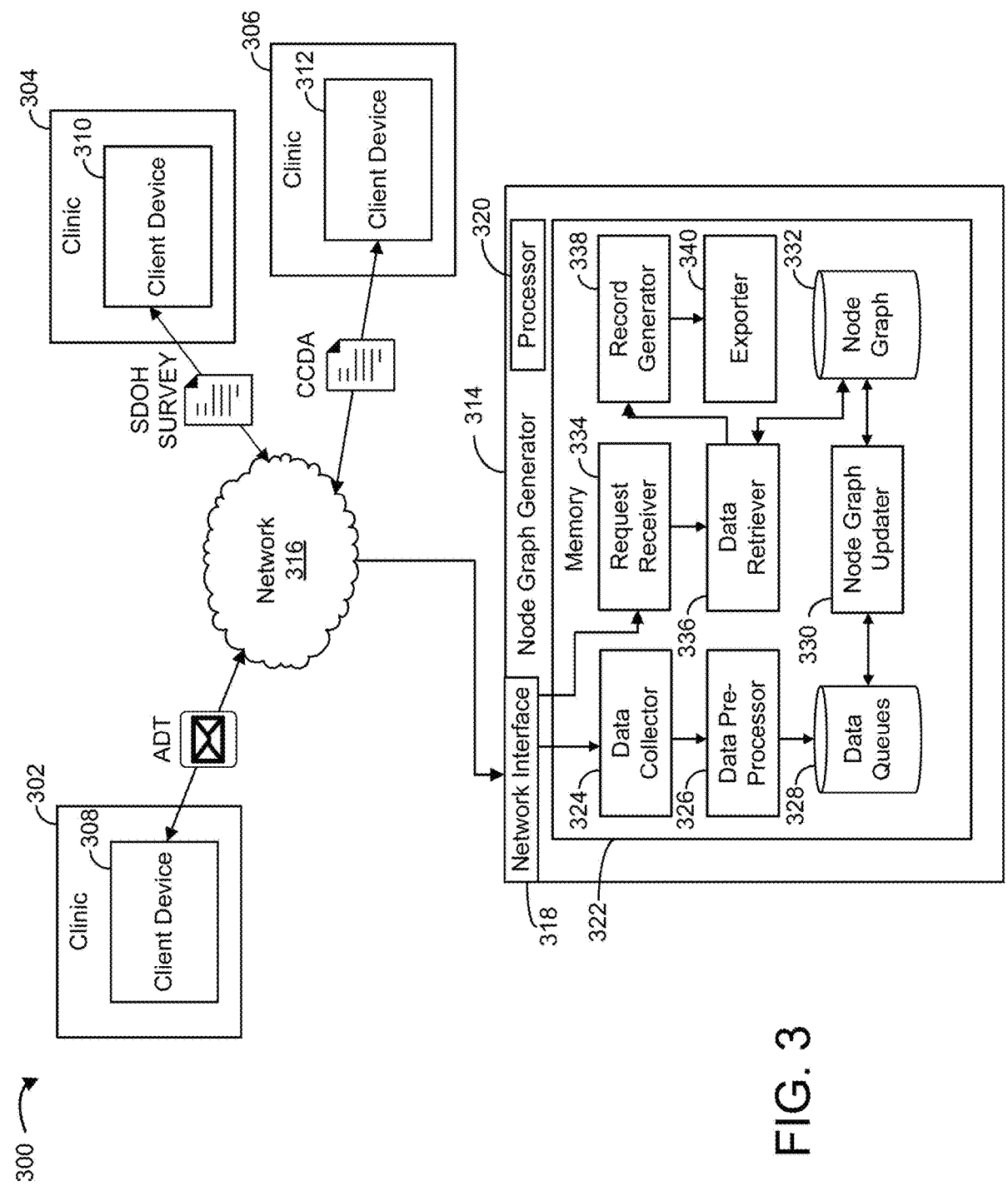
FIG. 3 is an illustration of an example node graph generation system, in accordance with some embodiments.

Referring now to FIG. 3, an illustration of an example node graph generation system 300 is shown, in some embodiments. In brief overview, node graph generation system 300 can include clinics 302, 304, and 306 that respectively operate and/or store client devices 308, 310, and 312. Client devices 308, 310, and 312 may communicate with a node graph generator 314 over a network 316. These components may operate together to store patient and clinic data in separate nodes of a node graph data structure in a central location (e.g., in node graph generator 314). Clinicians operating in clinics 302, 304, and 306 may operate client devices 308, 310, and 312 to request data about patients from node graph generator 314 to help perform a diagnosis as well as upload data about the same patients to node graph generator 314 about the patients' visits. Node graph generator 314 may use the node graph data structure to quickly retrieve any requested data (including data that was generated at other clinics) from the node graph data structure and transmit the data to the requesting client devices 308, 310, and 312. System 300 may include more, fewer, or different components than shown in FIG. 3. For example, there may be any number of client devices or computers that make up or are a part of node graph generator 314 or networks in system 300.

Clinics 302, 304, and 306 can include different types of healthcare clinics that provide care to patients. Examples of such clinics include emergency rooms, hospitals, primary care clinics, specialized clinics, mental health clinics, sports medicine clinics, chiropractor clinics, eye clinics, respiratory clinics, etc. Clinicians and doctors that treat patients at the clinics may create data files on client devices 308, 310, and 312 of different types of documents about patients' visits such as admission discharge and transfer documents (ADTs), consolidated clinical document architecture (CCDA) documents, social determinants of health (SOH) documents, attribution files, pre-adjudicated claims, etc. The files may include information about patients' visits to clinics 302, 304, and 306 such as the health statistics about the patients, medical diagnoses, updated demographic information that patients may fill out during the visits such as surgeries, vaccinations takes, prescribed medications, etc. Demographic information may include a patient's name, address, contact information, etc. Client devices 308, 310, and 312 may transmit the files containing the visit data to node graph generator 314 via network 316 for storage. Thus, node graph generator 314 may operate as a central storage device that stores patient data for clinics that are configured to provide data to node graph generator 314.

Client devices 308, 310, and 312 and/or node graph generator 314 can include or execute on one or more processors or computing devices and communicate via network 316. Network 316 can include computer networks such as the Internet, local, wide, metro, or other area networks, intranets, satellite networks, and other communication networks such as voice or data mobile telephone networks. Network 316 can be used to access information resources such as web pages, websites, domain names, or uniform resource locators that can be presented, output, rendered, or displayed on at least one computing device (e.g., client device 308, 310, or 312), such as a laptop, desktop, tablet, personal digital assistant, smartphone, portable computers, or speaker. For example, via network 316, client devices 308, 310, and 312 can request, from node graph generator 314, patient data about a particular patient or about a population of patients that have a defined set of attributes.

Each of client devices 308, 310, and 312, and/or node graph generator 314 can include or utilize at least one processing unit or other logic devices such as a programmable logic array engine or a module configured to communicate with one another or other resources or databases. The components of client devices 308, 310, and 312 and/or node graph generator 314 can be separate components or a single component. System 300 and its components can include hardware elements, such as one or more processors, logic devices, or circuits. As described herein, client devices can be referred to as client devices, computing devices, and/or computers.

Node graph generator 314 may comprise one or more processors that are configured to store and update a node graph data structure with patient data received from clinics 302, 304, and 306. Node graph generator 314 may comprise a network interface 318, a processor 320, and/or memory 322. Node graph generator 314 may communicate with client devices 308, 310, and 312 via network interface 318. Processor 320 may be or include an ASIC, one or more FPGAs, a DSP, circuits containing one or more processing components, circuitry for supporting a microprocessor, a group of processing components, or other suitable electronic processing components. In some embodiments, processor 320 may execute computer code or modules (e.g., executable code, object code, source code, script code, machine code, etc.) stored in memory 322 to facilitate the activities described herein. Memory 322 may be any volatile or non-volatile computer-readable storage medium capable of storing data or computer code.

Memory 322 may include a data collector 324, a data pre-processor 326, data queues 328, node graph updater 330, node graph data structure 332, request receiver 334, data retriever 336, record generator 338, and exporter 340, in some embodiments. In brief overview, components 324-340 may cooperate to collect different types of patient and clinic data from clinics 302, 304, and 306. Components 324-340 may store the collected data using a queue priority system to ensure high priority data (e.g., PHI data) is available for retrieval faster than lower priority data (e.g., demographic information). Components 324-340 may store the data in a node graph data structure such that the data about individual patients and data about populations of patients may be quickly retrieved upon receipt of a request for the data. Components 324-340 may use a weighting and relationship status node system to collect relevant data and avoid collecting stale or inaccurate data from the node graph data structure.

Components 324-340 may each include programmable instructions that, upon execution, cause processor 320 to perform a particular function. For example, data collector 324 may be or include an application programming interface (API) that communicates with corresponding APIs stored and executed by client devices 308, 310, and 312 at clinics 302, 304, and 306. Data pre-processor 326 may include programmable instructions that cause processor 320 to analyze and extract data from documents and/or data files that data collector collects via network interface 318. Data queues 328 may be or include a data base of prioritized queues from which extracted data can be retrieved to update a data structure, such node graph data structure 332. Node graph updater 330 may include programmable instructions that cause processor 320 to retrieve data from data queues 328 and add the retrieved data to node graph data structure 332. Node graph data structure 332 may be a graphical database that stores data for patients, clinics, and attributes of the patients in unique nodes. Request receiver 334 may be similar to or the same as data collector 324 and may include programmable instructions to receive requests for data from node graph data structure 332. Data retriever 336 may include programmable instructions that cause processor 320 to retrieve requested data from node graph data structure 332. Record generator 338 may include programmable instructions that cause processor 320 to generate a record or file with the retrieved data. Exporter 340 may include programmable instructions that cause processor 320 to export the generated record or data file back to the computing device that sent the request for which data was retrieved.

Node graph generator 314 may store node graph data structure 332. Node graph generator 314 may store node graph data structure 332 as a database in memory 322 such that node graph generator 314 may retrieve data from node graph data structure 332 upon receipt of a request. Node graph generator 314 may be a graph database with individual node graph data structures (e.g., nodes) that identify different entities or patients (e.g., entity or patient nodes), attributes of patients (e.g., attribute nodes), clinics (e.g., clinic or group entity nodes), lab result nodes, and other types of nodes. Each node in node graph data structure 332 may include a string identifier of the patient, attribute, or clinic the node represents or with which the node is associated. As described herein, for succinctness, references to attribute nodes may be references to clinic nodes, lab result nodes, and any other non-patient or non-entity nodes.

Node graph data structure 332 may also include edges between nodes that have a relationship with each other. For example, if a particular patient visited a clinic and was diagnosed with a disease during the visit, node graph data structure 332 may store an edge between the patient node for the patient and a clinic node for the clinic and an edge between the patient node and an attribute node for the disease. In some cases, node graph data structure 332 may also store an edge between the clinic node and the attribute node for the disease that indicates the disease was diagnosed at the clinic. Continuing with the example, if the patient visited another clinic and received the same diagnosis, the patient's node may have an edge with a clinic node for the second clinic and the clinic node may have an edge with the attribute node for the diagnosis. The nodes in node graph data structure 332 may have any number of edges with each other in node graph data structure 332.

In some embodiments, the nodes of node graph data structure 332 may be stored at coordinates in node graph data structure 332 and the edges may be stored as vectors. For example, a node may have coordinates in the form of (x,y) or (x,y,z) that indicate the position of the node in node graph data structure 332 and an edge may be a vector in the form of <x,y> or <x,y,z> with corresponding coordinates at at least one end of the vector as a position of the edge in node graph data structure 332. As nodes or edges are added to the node graph, node graph generator 314 may insert the edges and nodes at different positions.

In some embodiments, in addition to the edges between nodes, node graph data structure 332 may include relationship types of the edges. Node graph data structure 332 may store the relationship types in data structures that are dedicated to the individual edges. Node graph data structure 332 may store the relationships in data structures that are dedicated to the individual edges. The relationship types may indicate the types of relationships the nodes have with each other. For example, a patient node for a patient may have an "is associated with" relationship type with a zip code node if the patient lived in the zip code represented by the zip code node. Other examples of relationship types include "has an active consent form," "pertains to," "has treatment relationship with," "assigned to," "declared by," "has payment relationship with," "is in," "is diagnosed with," "is diagnosed by," "lives at," "can be contacted at," "previously had treatment relationship with," etc. When retrieving data from node graph data structure 332, node graph generator 314 may additionally retrieve the relationship data from the data structures of the edges and include the relationship data to provide context for the attributes.

In some embodiments, node graph data structure 332 may include weights (e.g., values or strength scores) for the edges between the nodes. The weights may be stored in the data structures for the edges. The weights may indicate the likelihood that the individual edges are correct. For example, a patient node may share an edge with a clinic node. The edge may have a weight on a scale (e.g., a scale from 1-100, a log scale, a natural log scale, etc.) that indicates the probability that the edge is correct and the patient has a relationship with the clinic. The weight may be based on "evidence" data collector 324 receives indicating the relationship between the patient node and the clinic node is correct. Evidence may be or include individual documents that include indications of the clinic and the patient, such as a document that includes both a string containing the patient's name and a string containing the name of the clinic. Node graph updater 330 may identify pieces of evidence, assign scores to the pieces of evidence based on the type of documents and/or the source or source types from which the evidence was received, as described below, and aggregate the scores together to obtain an aggregated score or the weight. In some embodiments, node graph updater 330 may calculate the weight from the aggregated score by performing another operation on the score, such as performing a natural log operation on the score. In doing so, node graph updater 330 may create a weight cap to stop the weights from increasing too much and to better control the weights of edges.

Node graph updater 330 may update the weights for the edges over time as node graph updater 330 receives data indicating the edge is correct. For example, node graph data structure 332 may store an edge between a patient node for a patient and a zip code node for a zip code indicating the patient lives in the zip code. The weight for the edge may be 20 out of 100 because node graph data structure 332 may not have a significant amount of evidence that indicates the patient lives at the zip code. Node graph generator 314 may receive a document file from a clinic with the patient's name and the zip code on it. Node graph updater 330 may identify the name and the zip code on the file and increase the weight for the edge based on the new document file that includes both the patient's name and the zip code. Node graph updater 330 may continuously update the edge over time to increase the weight of the edge. By doing so, node graph updater 330 may enable users to query node graph data structure 332 for data based on edges having weights above a defined threshold, therefore reducing the risk that data retriever 336 retrieves inaccurate data. Node graph generator 314 may similarly maintain and update any number of weights for edges between nodes.

In some embodiments, node graph data structure 332 may include multiple edges between a single pair of nodes. Each of the edges may be dedicated to data from a different overlapping or non-overlapping time period. For example, a patient node may share edges for different months with a diagnosis node. In some embodiments, the patient node may also have an edge for the "lifetime" of the relationship between the two nodes. Each of the edges may have its own weight indicating the likelihood that the relationship between the two nodes for the time period of the edge is correct.

Node graph updater 330 may update the weights for the edges based on the times in which the data files are received, the times in which the data files are generated, or the times in which the data files are transmitted. For example, upon receiving a data file, node graph updater 330 may identify a time stamp of the data file from an electronic document in the data file (e.g., identify a time on the electronic document using object character recognition techniques), a time in which node graph generator 314 received the data file, or a time stamp from the body or header of the data packet that contains the data file. Node graph updater 330 may identify a patient node and attribute nodes based on the nodes having identifiers that match the data in the data file. For each identified attribute node, node graph updater 330 may identify the edges between the patient node and the attribute node and compare the time stamp with the time periods of the edges. Based on the comparison, node graph updater 330 may identify the edge that is associated with a time period that encompasses the time stamp (e.g., includes the time and/or date of the time stamp) and increase the weight of the edge based on the data file containing data corresponding to the patient node and attribute node for the time period. In some embodiments, node graph updater 330 may additionally update an edge containing the weight for the lifetime of the relationship between the patient node and the attribute node based on the data. Node graph updater 330 may similarly update edges between the patient node and other attributes that node graph updater 330 updated based on data in the data file. In this way, node graph generator 314 may maintain a binned history of the data node graph generator 314 collects from clinics that can be used to retrieve data based on searches for data from different time periods.

Data collector 324 may receive a plurality of data files from a data source. Data collector 324 may receive the plurality of data files from a data source such as a client device at a clinic. The data files in the plurality of data files may correspond to different visits by patients at the clinic. For example, over the course of a day, multiple patients may visit a clinic for care. A clinician may speak to the patients and upload documents to a computer at the clinic indicating the clinician's diagnoses for the patients and other data generated from the visit. The computer may store the documents as data files in memory and transmit the data files to data collector 324.

Computers at clinics may transmit any type of documents as data files to data collector 324. Examples of types of documents the computers may transmit include, but are not limited to, ADT's, CCDA documents, SOH documents, attribution files, and pre-adjudicated claims. In some cases, different types of clinics may transmit different types of documents (e.g., an emergency clinic may generate and transmit different types of documents or documents with different types of data than a dermatology clinic). The documents may be stored in the data files as text documents and/or may include images.

In some embodiments, data collector 324 may store data files data collector 324 receives from clinics in a separate database, such as a relational database. Data collector 324 may store the data files with time stamps indicating the times and/or dates data collector 324 received the data files, the data files were generated, and/or the data files were transmitted. In some embodiments, data collector 324 may also store identifications of the individuals for which the data files include information. In some embodiments, data collector 324 may also store unique numerical or alphanumerical identifiers of the data files that can be used to quickly look up the respective data files.

Data pre-processor 326 may identify time stamps for each of the data files. Data pre-processor 326 may identify the time stamps for the data files by identifying the times in which the data files are received, the times in which the data files are generated, or the times in which the data files are transmitted, depending on the configuration of data pre-processor 326. For example, when data pre-processor 326 is configured to identify time stamps for the data files by identifying the times in which the data files are received, data pre-processor 326 may identify the time data pre-processor 326 received the data from an internal clock and store an association between the identified time and the data file in an internal database (e.g., a relationship database). In another example, when data pre-processor 326 is configured to identify the times in which the data files are transmitted, data pre-processor 326 may identify time stamps in the bodies or headers of the data packets that include the data files and store associations between the identified times and the data files in the database. In yet another example, when data pre-processor 326 is configured to identify the times in which the data in the data files was generated, data pre-processor 326 may use object recognition techniques and/or natural language processing techniques to identify times and/or dates in the text of the data files and store associations between the identified times and/or dates and/or the data files in the database.

Data pre-processor 326 may extract data from data files. Data pre-processor 326 may extract data from the data files using natural language processing techniques and/or object recognition techniques. For example, data pre-processor 326 may extract data from the data files by identifying patient names, patient attributes, medical diagnoses, clinic names, and other types of data from the data files. In some embodiments, data pre-processor 326 may identify the data in the data files responsive to the data matching stored values in memory 322 of node graph generator 314. Data pre-processor 326 may extract the data as key words such that data pre-processor 326 may compare the data to values of nodes in node graph data structure 332 to determine whether to generate new edges or update weights of the edges in node graph data structure 332.

Data pre-processor 326 may identify data from a data file. Data pre-processor 326 may identify data from the data file by identifying the file or location in memory that contains the extracted data from the data file. For example, data pre-processor 326 may scan the files of extracted data or the places in memory that contain the extracted data. Data pre-processor 326 may identify a file or location in memory from which data pre-processor 326 has not previously retrieved data to use to update node graph data structure 332.

Data pre-processor 326 may identify nodes from node graph data structure 332. In identifying the nodes, data pre-processor 326 may first identify the patient nodes that correspond to the patients for which the data of the data file was generated. To do so, data pre-processor 326 may identify an extracted name value from the data file. Data pre-processor 326 may determine the extracted name value is a name versus another type of value by comparing the extracted value to a database with strings of possible names. If data pre-processor 326 determines the extracted name value matches a string in the database of possible names, data pre-processor 326 may determine the value is a name. Upon determining the value is a name, data pre-processor 326 may label the data file from which the name value was extracted with an identification of the name to indicate the data from the data file is associated with the name. Data pre-processor 326 may store the labeled data file and/or the extracted data from the data file in data queues 328. In this way, data pre-processor 326 may identify the name of the patient that is associated with the data file.

In some embodiments, instead of or in addition to identifying the name from the data file, data pre-processor 326 may identify a common key for the data file. The common key may be a unique alphanumerical identifier for the patient. Data pre-processor 326 may identify the common key for the data file by extracting the common key from the data file itself. Data pre-processor 326 may also identify the common key by performing identity resolution or authentication on the data according to the methods described in U.S. Pat. No. 10,009,332, filed Mar. 9, 2015, the entirety of which is incorporated by reference herein. Data pre-processor 326 may authenticate the identity of the person identified in the document and identify the common key for the person, such from an index or database.

Upon data pre-processor 326 identifying the name value or common key for the data file and storing the data file and/or data in data queues 328, node graph updater 330 may identify the patient node that corresponds to the name or common key. Node graph updater 330 may identify the patient node that corresponds to the name or common key by querying the patient nodes in node graph data structure 332 for values that match the name value or the common key. Node graph updater 330 may identify a patient node for the data file responsive to the patient node having a matching string to the name value or common key.

Node graph updater 330 may identify attribute nodes (or any other type of nodes) in node graph data structure 332 that correspond to the other values from the data file. For example, node graph updater 330 may compare the extracted values from a data file to the non-patient nodes (e.g., attribute nodes) of node graph data structure 332. Node graph updater 330 may identify any of the attribute nodes that have matching values to the extracted values. Together, an attribute node that has a relationship with a patient node may be a patient node-attribute node pair.

Node graph updater 330 may determine whether the time stamp of the data file has a corresponding edge between the identified patient node and the identified attribute nodes. For example, after identifying the patient node and the attribute nodes for the data file, node graph updater 330 may identify the edges in the patient node-attribute node pairs. Node graph updater 330 may identify the time periods that correspond to each of the edges and compare the time and/or date of the time stamp with the time periods. Based on the comparison, for each patient node-attribute node pair, node graph updater 330 may determine if the patient node-attribute node pair contains an edge with a time period that includes the time. If node graph updater 330 does not identify an edge with a time period that includes the time for a patient node-attribute node pair, node graph updater 330 may determine the time stamp does not have a corresponding edge between the patient node and the attribute node of the patient node-attribute node pair. If node graph updater 330 identifies an edge with a time period that includes the time stamp for a patient node-attribute node pair, node graph updater 330 may determine the time stamp does have a corresponding edge between the patient node and the attribute node of the patient node-attribute node pair.

In some cases, the node graph updater 330 may maintain and increment a counter in the data structure of each edge that indicates the number of data sources that have provided data or evidence that corresponds to the edge. The example, the node graph updater 330 may identify the data sources that provided data or evidence that contributed to a score. For each unique data source, the node graph updater 330 can increment the counter. The node graph updater 330 can store the incremented counter in the data structure.

For each patient node-attribute node pair with an edge that corresponds to the time stamp, node graph updater 330 may update a weight of the corresponding edge. For example, node graph updater 330 may identify the weight of the corresponding edge from node graph data structure 332. Node graph updater 330 may identify the weight of the edge which may be stored in memory as an attribute of the edge with a list or count of data files that have been used to update the edge. Node graph updater 330 may update the list by storing an identification of the data file in the edge attribute or incrementing the counter to indicate another data file contains evidence that the patient node is linked to the attribute node. Node graph updater 330 may then update the weight by calculating a new weight by aggregating the new data file with the data files that were previously used to update the weight.

In some embodiments, node graph updater 330 may update the weight of the edge by assigning a weight to the data file. For example, node graph updater 330 may assign a weight to the data file based on the type of document in the data file and/or the source of the data file. Different types of data files may be associated with different weights. For example, ADTs may be associated with a higher weight than CCDAs which may be associated with a higher weight than SDOH surveys. Node graph updater 330 may store weights for any number of types of data files and the weights may be in any order between document types. Such weights may be trust scores indicating the level of trust node graph updater 330 (or an administrator configuring node graph updater 330) has that the information in the different types of documents is accurate. Node graph updater 330 may identify the type of document from the data in the document or from a document type in the data file that contains the document. Similarly, node graph updater 330 may store weights for different data sources. The weights may be trust scores indicating the level of trust node graph updater 330 (or an administrator configuring node graph updater 330) has that the information from the data sources is correct. For example, hospitals may be associated with higher weights than family practice clinics, which may have higher weights than community health organizations, etc. Node graph updater 330 may store weights for any number of types of data sources. Node graph updater 330 may aggregate, multiply, or perform any type of operation on the two weights for the data file to obtain an evidence weight for the data file and aggregate the evidence weight with the previously stored weight for the edge to obtain an aggregated weight. In some embodiments, node graph updater 330 may then calculate the natural logarithm of the aggregated weight to obtain a new weight for the edge. Accordingly, node graph updater 330 may take into account the evidence of the relationship between the attribute node and the patient node in the weight of the edge for the corresponding time period to the time stamp of the data file. Node graph updater 330 may similarly update the weights of edges for any number of data files.

For each patient node-attribute node pair without an edge that corresponds to the time stamp, node graph updater 330 generates an edge for a time period that includes the time and/or date of the time stamp. Node graph updater 330 may generate the time period to have a predefined length. In some embodiments, node graph updater 330 may store a series of defined time periods in memory. Upon determining there is not an edge between the patient node and the attribute node of the patient node-attribute node pair that corresponds to a time period including the time and/or date of the time stamp, node graph updater 330 may query memory 322 for a time period that is inclusive of the time and/or date of the time stamp. Upon identifying the time period, node graph updater 330 may insert an edge between the patient node and attribute node of the patient node-attribute node pair and retrieve and insert the identified time period as an attribute of the new edge. Node graph updater 330 may do so by inserting pointers (e.g., a selectable addresses that navigates the data processing system to the other node or otherwise an identification of the other node) in the nodes to the other node of the edge. Node graph updater 330 may then calculate a weight for the edge based on the document type and/or source of the data file that caused node graph updater 330 to generate the edge as described above. In this way, node graph updater 330 may maintain a dynamic node graph data structure that can store an increasing amount of data in a time-organized fashion.

Node graph updater 330 may determine if the attribute of the patient node-attribute node pair is the last attribute for which to store data from the data file. Node graph updater 330 may identify the data node graph updater 330 extracted from the data file and determine if all of the data had been matched to a patient node-attribute node pair. If node graph updater 330 identifies a new word or phrase that matches an attribute node, node graph updater 330 may repeat these operations until determining there is not any more data to use from the data file to update node graph data structure 332.

Node graph updater 330 may determine if the data file is the last data file. Node graph updater 330 may determine if the data file is the last data file by examining the batch of files for which node graph updater 330 is processing data. If node graph updater 330 determines there is another data file in the batch from which data was extracted, node graph updater 330 may identify the data file and repeat the operations until determining there are not any further data files to use to update node graph data structure 332.

Record generator 338 may generate a record indicating the update to node graph data structure 332 is complete for the batch of data files. The record may be an indication on a user interface that exporter 340 transmits to an administrative computer to indicate the data has been uploaded. In some embodiments, record generator 338 may generate the record to indicate a list of the updates node graph updater 330 made as a result of the batch upload. Record generator 338 may store such a record in memory 322. Accordingly, node graph generator 314 may maintain an active record of updates node graph updater 330 makes to node graph data structure 332.

Request receiver 334 may receive a request for data. The request for data may be a request for data about a particular patient or a request for data about patients that have a certain set of attributes. For example, the request may include a string identification of a patient (e.g., the patient's name or the patient's common key) in a data packet. In this example, node graph generator 314 may process the request as a request for data about the patient. In another example, the request may include string identifications of attributes (e.g., a set of attributes). In this example, the request may be for a population list of patients that share each of the attributes. Based on either of the example requests, data retriever 336 may query node graph data structure 332 for the requested data.

Data retriever 336 may determine a type of data being requested. Data retriever 336 may make this determination based on the context of the data in the body of the request. The types of data that may be requested are data (e.g., attributes) about a particular individual or patient and/or data about patients (e.g., a list of individuals or patients) that share a requested set of attributes. Data retriever 336 may determine the type of data being requested by identifying the data in the request. If data retriever 336 identifies a single name of a patient or any number of names of patients in the request, data retriever 336 may determine the request is for data about the named patient or named patients. If data retriever 336 identifies a list of attributes in the request, data retriever 336 may determine the request is for data about a population that includes the attributes.

Responsive to determining the request is for data about individual patients, data retriever 336 may identify edges of a patient node that corresponds to the named patient. To do so, data retriever 336 may query node graph data structure 332 using the name in the query. Data retriever 336 may identify a patient node that contains the name. Data retriever 336 may then identify an edge that connects the patient node to another node (e.g., an attribute node).

Data retriever 336 may determine if the identified edge has a weight that exceeds a threshold. The threshold may be a value that the requesting client device includes in the request or a stored value in memory of data retriever 336. The threshold may indicate a minimum level of confidence that the two nodes should be linked. Data retriever 336 may compare the weight of the edge to the threshold. If data retriever 336 determines the weight of the edge is less than the threshold, data retriever 336 may disregard the edge (e.g., not retrieve the attribute of the attribute node attached to the edge). However, if data retriever 336 determines the weight of the edge is equal to or greater than the threshold, data retriever 336 may identify (e.g., retrieve and temporarily store in random access memory) the attribute of the attribute node attached to the edge. Accordingly, data retriever 336 may only retrieve attributes to include in a response to a request for data about a patient for which data retriever 336 has enough evidence to satisfy a threshold in the request or a locally stored threshold.

Data retriever 336 may determine if the identified edge is the last edge connected to the patient node. Data retriever 336 may do so by scanning the patient node for edges. If data retriever 336 identifies another edge from the scan, data retriever 336 may repeat these operations until data retriever 336 does not identify an edge connected to an attribute node for which data retriever 336 has not evaluated or otherwise retrieved from memory.

In some embodiments, data retriever 336 may only identify edges that correspond to a time period that includes a date or time identified in the request. For example, data retriever 336 may receive a request for data about a patient from a specific time period or from a particular time. Data retriever 336 may receive such a request, for example, when a physician is seeking to look at the medical history of a patient and seeks to see previous vital signs or prior illnesses that a patient has had. Upon receiving the request, data retriever 336 may identify a patient node in node graph data structure 332 that corresponds to the patient identified in the request and identify the edges the patient node shares with other nodes. Data retriever 336 may identify the edges that correspond to the time period or time stamp included in the request. Data retriever 336 may compare the weights of identified edges to a threshold to determine which attributes to identify and use in response to the request. The requests may include identifications of one or more time stamps and time periods in addition to or instead of requests for attributes that correspond to a "lifetime" edges that includes a weight calculated for the lifetime in which the patient node and the attribute node have a relationship. Accordingly, data retriever 336 may store and provide historical information to inquiring clinicians to enable the clinicians to request historical information about patients.

If data retriever 336 determines the type of data is for a population that has a particular set of attributes, data retriever 336 may first identify the edges of attribute nodes of node graph data structure 332 that correspond to the set of attributes included in the request. To do so, data retriever 336 may query node graph data structure 332 using names of the attributes in the query. Data retriever 336 may identify the attribute nodes that contain the strings identifying the attributes. Data retriever 336 may then identify an edge that connects an attribute node to a patient node.

Data retriever 336 may determine whether a weight of the edge exceeds a threshold. Data retriever 336 may determine whether the weight of the edge exceeds the threshold in a similar manner to how data retriever 336 determined whether a weight of an edge exceeds a threshold when retrieving attributes about individual patients. If data retriever 336 determines the weight exceeds the threshold, data retriever 336 may disregard the edge (e.g., not store in random access memory). However, if data retriever 336 determines the weight of the edge exceeds the threshold, data retriever 336 may identify (e.g., retrieve and temporarily store in random access memory) an identification of the edge. Accordingly, data retriever 336 may only retrieve attributes to include in response to a request for data about a patient for which data retriever 336 has enough evidence to satisfy a threshold in the request or a locally stored threshold.

Data retriever 336 may determine if the identified edge is the last edge connected to the attribute nodes for the attributes identified in the request. Data retriever 336 may do so by scanning attribute nodes for edges data retriever 336 identified in response to the request but has not yet evaluated against a threshold. If data retriever 336 identifies another edge from the scan, data retriever 336 may repeat these operations until data retriever 336 does not identify an edge connected to an attribute node for which data retriever 336 has not evaluated or otherwise retrieved from memory.

Data retriever 336 may determine if a patient node has edges with each of the attribute nodes that were identified in response to the request. Data retriever 336 may identify a patient node in node graph data structure 332 in response to determining the patient node has at least one edge that data retriever 336 determined has a weight satisfying the threshold. Upon identifying the patient node, data retriever 336 may identify each of the attribute nodes that correspond to the attributes from the request and determine whether the patient node has an edge with each of the attribute nodes. If data retriever 336 determines there is at least one attribute node with which the patient node does not have an edge, data retriever 336 may disregard the patient node. If data retriever 336 determines the patient node has an edge with all of the attribute nodes, however, data retriever 336 may identify the patient node. Although not shown, data retriever 336 may repeat these operations for each patient node that has at least one edge with the attribute nodes identified based on the request until data retriever 336 has evaluated each of such patient nodes. In this way, data retriever 336 may identify a population of patients that have a requested set of attributes using a node graph data structure.

Record generator 338 may generate a record (e.g., a file, document, table, listing, message, notification, etc.) indicating the data the data processing system retrieved in response to receiving the request. For example, if data retriever retrieved data about a particular patient, record generator 338 may generate a list of attributes associated with attribute nodes that have edges with a patient node for the patient and satisfy criteria included in the request in a record. In another example, if data retriever 336 retrieved data about a population of patients that have a defined set of attributes, record generator 338 may generate a list of patients associated with patient nodes that have edges with attribute nodes that are associated with the requested attributes. Exporter 340 may transmit the record to the requesting client device in a data packet and/or as a user interface such that a user accessing the requesting client device can view the retrieved data. In this way, the data processing system may use a node graph data structure to store and retrieve data received from different clinics to provide data to requesting users.

Data collector 324 may receive a set of data from one or more data sources. The data sources may be computers of different types of clinics or healthcare providers. The set of data may include different entries of data that clinicians at the clinics or healthcare providers create to indicate attributes about patients that visit or visited the respective clinics or healthcare providers for treatment. The set of data may include data files that each include one or more documents with handwritten or typed data about the patients. Data collector 324 may receive such data from any number of data sources over time via an API data collector 324 may use to communicate with the data sources.

Data pre-processor 326 may parse the set of data. Data pre-processor 326 may parse the set of data using natural language processing and/or object recognition techniques. For example, data pre-processor 326 may retrieve data files from the set of data and/or identify words, phrases, and/or images from the data files using natural language processing and object recognition techniques. Data pre-processor 326 may extract the words, phrases, and images using such techniques and store the data in memory (e.g., random access memory) to parse the data.

In some embodiments, data pre-processor 326 may categorize the extracted data based on the type of the data. For example, data pre-processor 326 may compare the words, phrases, or images to a keyword database (e.g., a relational database) that indicates the types (e.g., PHI, provider name, demographic data, etc.) of data with which different words, phrases, or images are associated. Data pre-processor 326 may identify matches between the compared data and label the different words, phrases, or images based on the matches. In this way, data pre-processor 326 may create a labeled list of the data and the type of the data that data collector 324 receives from different clinics.

In some embodiments, in addition to or instead of categorizing the extracted data based on the type of the data, data pre-processor 326 may categorize the extracted data based on the data source that provided the data. For example, upon receiving a data file from a data source, data pre-processor 326 may identify the data source of the data file by identifying an identifier of the computing device that transmitted the data packet with the data file (e.g., identify an identifier in the data packet itself, an identifier that data collector 324 received when establishing a connection with the computing device such as a device address, a text identifier in the data file itself, etc.). Data pre-processor 326 may compare the identifier to a data source database that includes a list of data sources and their respective identifiers. Data pre-processor 326 may identify the data source that provided the data file based on the data source having a matching identification to an identifier in the database. Data pre-processor 326 may label the data file and/or the data that data pre-processor 326 extracted from the data file with an identification of the data source. In some embodiments, data pre-processor 326 may label the data with the source type (e.g., general practice clinic, hospital, emergency clinic, orthopedic clinic, etc.) in a similar manner (e.g., compare the identifier for the data source to a database containing identifications of source types). Thus, node graph generator 314 may maintain a record of the data sources that provided data files to node graph generator 314.

In some embodiments, in addition to or instead of categorizing the extracted data based on the type, source, and/or source type of the data, data pre-processor 326 may categorize the extracted data based on the file or document type of the file or document from which the data was extracted. Examples of file or document types include, but are not limited to, ADT's, CCDA's, SDOH surveys, attribution files, pre-adjudicated claims, etc. Data pre-processor 326 may identify the document type or file type by using natural language processing techniques or object character recognition techniques on the documents or files and identifying language or images that correspond to the document or file type. Data pre-processor 326 may then label the data extracted from the data files or documents based on the identified types.

Data pre-processor 326 may select queues in data queues 328 to insert the parsed data based on the types of information of the parsed data. Data queues 328 may be shared or separate dedicated locations to store data in memory. Each queue may be associated with a distinct priority (e.g., high, medium, or low, or 1, 2, or 3). Data pre-processor 326 may select the queues for each separate piece of data (e.g., text, phrase, or image) or for the data files themselves based on the labels (e.g., types of information) data pre-processor 326 determined for the data or the data files. To do so, data pre-processor 326 may identify the labels on the data or data files. Data pre-processor 326 may compare the labels to a database to identify the priorities that correspond to the labels. Upon identifying the priorities for the data or data files, data pre-processor 326 may insert the data or data files into the corresponding selected queues with matching priorities by storing the data or data files in the location or data queues 328.

Data pre-processor 326 may identify priorities for data or data files based on any combination of labels (e.g., data type, source, source type, document or data file type, etc.). For example, data pre-processor 326 may identify priorities for data based on the document or data file type of the data from which the data was extracted. Doing so may be advantageous in healthcare because different types of documents may have higher priority data about patients than other types of documents. For instance, an ADT may have higher priority data than and SDOH surveys because an ADT may be more likely to have PHI and/or information from ADTs may be more likely to include information that will create or significantly strengthen edges between nodes. In another example, data pre-processor 326 may identify the priorities of the individual pieces of data based on the types of data. For instance, data pre-processor 326 may identify higher priorities for PHI than for demographic data. In yet another example, data pre-processor 326 may identify the priorities of the data or the data files based on the sources or source types from which the data or data files originated. For instance, data pre-processor 326 may identify higher priorities from general practice clinics than from orthopedic clinics because general practice clinics may have more sensitive information (e.g., blood type, disease diagnoses, etc.). By prioritizing the data or data files in this manner, data pre-processor 326 may ensure higher priority information is available for retrieval from the data structure earlier than lower priority data, enabling physicians to have access to PHI faster to help the physicians make more accurate diagnoses.

Node graph updater 330 may initiate a data upload of the extracted data. Node graph updater 330 may do so by starting to retrieve data from the queues to upload into the data structure. Node graph updater 330 may initiate the data upload using a batch processing or continuous processing technique.

Node graph updater 330 may identify a queue from data queues 328 from which to retrieve data. Node graph updater 330 may identify the queue according to a stored set of criteria. For instance, node graph generator 314 may store a set of rules that indicate an order of queues from which to retrieve data. The rules may indicate to retrieve data from the queues in sequential order (e.g., retrieve all of the data from the highest priority queue, then from the next highest priority queue, etc.), retrieve a defined amount of data (e.g., a defined number of attributes) from each queue in a defined sequence and then repeating the sequence, or according to any other rules. Node graph updater 330 may identify a queue according to the set of criteria.

After identifying the queue, node graph updater 330 retrieves data from the queue. Node graph updater 330 may retrieve data from the queue in the order in which the data was stored. For example, when storing the data in the queue, node graph updater 330 may store time stamps with the data to indicate the time in which the data was stored. Node graph updater 330 may query timestamps in the queue and identify the data that is associated with the earliest time stamp and retrieve the identified data.

Node graph updater 330 may update the data structure with the retrieved data. Node graph updater 330 may update the data structure by adding the retrieved data to the data structure. In some embodiments, node graph updater 330 updates the data structure by updating a node graph data structure in a similar manner to the manner described above.

Node graph updater 330 may determine if there is any more data to retrieve to update the data structure. Node graph updater 330 may do so by querying the queues according to the stored set of criteria. For example, upon updating the data structure, node graph updater 330 may identify the next queue from which to retrieve data according to the stored criteria. Node graph updater 330 may query the queue for data, and if there is a piece of data in the queue, repeatedly retrieve and update the data structure with the data from the queue. If there is not any data left in the queue, node graph updater 330 may identify the next queue according to the stored criteria (e.g., the next queue in a sequence or the queue with the next highest priority) and query the next queue for data. Node graph updater 330 may continuously repeat these operations until node graph updater 330 determines there is not any more data to retrieve in data queues 328.

Upon determining there is not anymore data to retrieve from the queues, record generator 338 generates a notification indicating the update is complete. The notification may be a record that includes a list of data node graph updater 330 uploaded to node graph data structure 332. Exporter 340 may transmit the notification to an administrator device to indicate the data from the data files has been successfully uploaded to the data structure and is available for sharing.

Node graph updater 330 may link a patient node with a clinic node through a relationship status node. Node graph updater 330 may link the patient node with the clinic node in response to receiving a data file from a clinic associated with the clinic node indicating a patient associated with the patient node received or is actively receiving care from the clinic. To link the patient node with the clinic node, node graph updater 330 may generate a "relationship status" node. A relationship status node may be a node that contains a status history list indicating time periods in which a patient actively received care from a clinic. Node graph updater 330 may generate the relationship status node by instantiating a relationship status node at a location in the node graph that includes a string indicating the relationship status node is a relationship status node, such as "active care" or "relationship status." Node graph updater 330 may link the relationship status node with the patient node and the clinic node.

Data collector 324 may receive a data file from the clinic of the clinic node that identifies the patient and the clinic. Data collector 324 may receive the data file and parse the data file to determine the data file includes the identifications of the clinic and the patient.

Node graph updater 330 may add a string including an active status to the relationship status node. Node graph updater 330 may add the string including the "active" status to the relationship status node responsive to receiving the data file from the clinic. Node graph updater 330 may identify the status history list in the relationship status node and add strings indicating an identification of the status, a start date and/or time of the active status, and an expiration date and/or time of the active status. Node graph updater 330 may set the identification of the status as an alphanumerical character that sequentially increases for each active status node graph updater 330 adds to the relationship status node. Because the relationship status node includes a history of active statuses that have been added, node graph updater 330 may maintain a history indicating times in which patients received care from a patient.

In one example, node graph updater 330 may use the status relationship node to determine a time period for which to add new evidence (e.g., the time period edge for which to adjust a weight). For instance, node graph updater 330 may determine an "as of date" as the month or time period to apply a data file (or extracted data) to use as evidence. Node graph updater 330 may do so based on the time stamp node graph updater 330 assigned or determined for the data file. Next, node graph updater 330 may determine a month or time period score for the time period or month according to the following formula:

$$\text{LOG BASE 2(sum of monthly(evidence weight*source trust factor))}$$

The monthly or time period evidence count (e.g., a count of the number of evidence documents node graph generator 314 received for the month or time period) and data source count (e.g., a count of the number of data sources that provided data for the month or time period) that are stored as attributes of the edge (e.g., attributes stored in a vertex or separate data structure that stores data for the edge) may be updated based on the data file. Node graph updater 330 may also store a pointer to a separate database that stores the data file and a timestamp indicating when data from the data file was added to node graph data structure 332 in the attributes of the edge.

Node graph updater 330 may next evaluate the evidence to determine a status update is necessary. Node graph updater 330 may determine a status update is necessary if:
  a. the relationship is currently in an active status and the expiration date calculated based on the evidence being evaluated is greater than the current active expiration date. In this case, the current active expiration date should be updated based on the new evidence according to the equation:

EXPIRATION DATE=CURRENT DATE+EVIDENCE SCORE/EVIDENCE DECAY FACTOR.

b. the relationship is not currently active and the expiration date calculated based on the evidence being evaluated is greater than the current date (e.g., the expiration date is in the future). In this case, node graph updater 330 may create a new active status in the relationship status node with an as of date equal to the date the evidence is being processed and an expiration date equal to the expiration date calculated based on the new evidence. The expiration date may be calculated according to the equation:

EXPIRATION DATE=CURRENT DATE+EVIDENCE SCORE/EVIDENCE DECAY FACTOR.

c. The relationship is not currently active and the expiration date calculated based on the evidence being evaluated is greater than the most recent expiration date for the last expired active status (e.g., the expiration date calculated from the backdated evidence would extend the time period covered by the most recent active status even though it does not create a current active care status). This expiration date may need to be updated as it may facilitate access to more recent patient data than would be allowed by the statuses in the current status history node. Node graph updater 330 may mark the active care status as a post-dated active status (e.g., it is being applied retroactively so that it would be clear when data would have been shared and when it would not have).

In performing the above operations, node graph updater 330 may calculate weights for individual pieces of evidence based on the evidence or source of the evidence as described herein. Node graph updater 330 may calculate the scores for the edges such that the scores do not decay directly over time, but rather are binned by time period or month. If node graph updater 330 never receives a data file for a time period of an edge, node graph updater 330 may not create an edge for the time period. Finally, node graph updater 330 may track a status history independently of the weights for the individual months and indicate active periods of the relationship between two nodes. Every time evidence is submitted the evidence may be evaluated to determine if a new active status should be established or an existing expiration date updated. In this way, node graph generator 314 may store a record of when patients received care from particular clinics and when the patients stopped receiving such care.

Request receiver 334 may receive a request for data about a patient. The request may include a time stamp or time period indicating times from which to retrieve data. Upon receiving the request, data retriever 336 may identify the patient node for the patient from node graph data structure 332. Data retriever 336 may also identify the relationship status nodes to which the patient node is linked.

Data retriever 336 may determine whether the relationship status node indicates an active status for the time period or a time period that includes the time stamp. For each relationship status node, data retriever 336 may identify active status time periods (e.g., the time between the as of date and the expiration date of the active status) and determine if the respective relationship status nodes have an active status time period that includes the time period or time stamp in the request. For any relationship status that does not include such an active status, node graph updater 330 may insert a label in memory indicating not to retrieve any data from the data source for the request.

Upon identifying relationship status nodes with an active status time period containing the time period or the time stamp, data retriever 336 may retrieve data that is associated with the clinic nodes linked by the relationship node with the active status. For example, data retriever 336 may identify the clinic nodes that are linked to relationship nodes with an active status for the time period or timestamp in the request. Data retriever 336 may retrieve identifications of the clinics associated with such clinic nodes to send in a response to the request, in some embodiments only responsive to determining the weight for the edge that corresponds to the requested time period or time stamp and/or the exceeds a threshold. Thus, data retriever 336 may retrieve a list of clinics from which the patient received active care during a requested time period.

In some embodiments, data retriever 336 may additionally or instead identify pointers to the data files in the edge for the time period between the patient node and the clinic node. Data retriever 336 may identify the pointers from the edge by accessing the pointers from the attributes of the edge. Data retriever 336 may select the pointers to access the locations of the data files from a database (e.g., a local database stored in data retriever 336 or a remote database stored by another computer). Data retriever 336 may retrieve the data files and/or the name of the clinic from the clinic node.

Record generator 338 may generate a record from the retrieved data. Record generator 338 may generate the record by creating a folder that includes the retrieved data files and/or a document indicating names of the clinics that had an active care status during the requested time period or time of the time stamp. Exporter 340 may then transmit the record to the requesting computing device.

Figure 4:
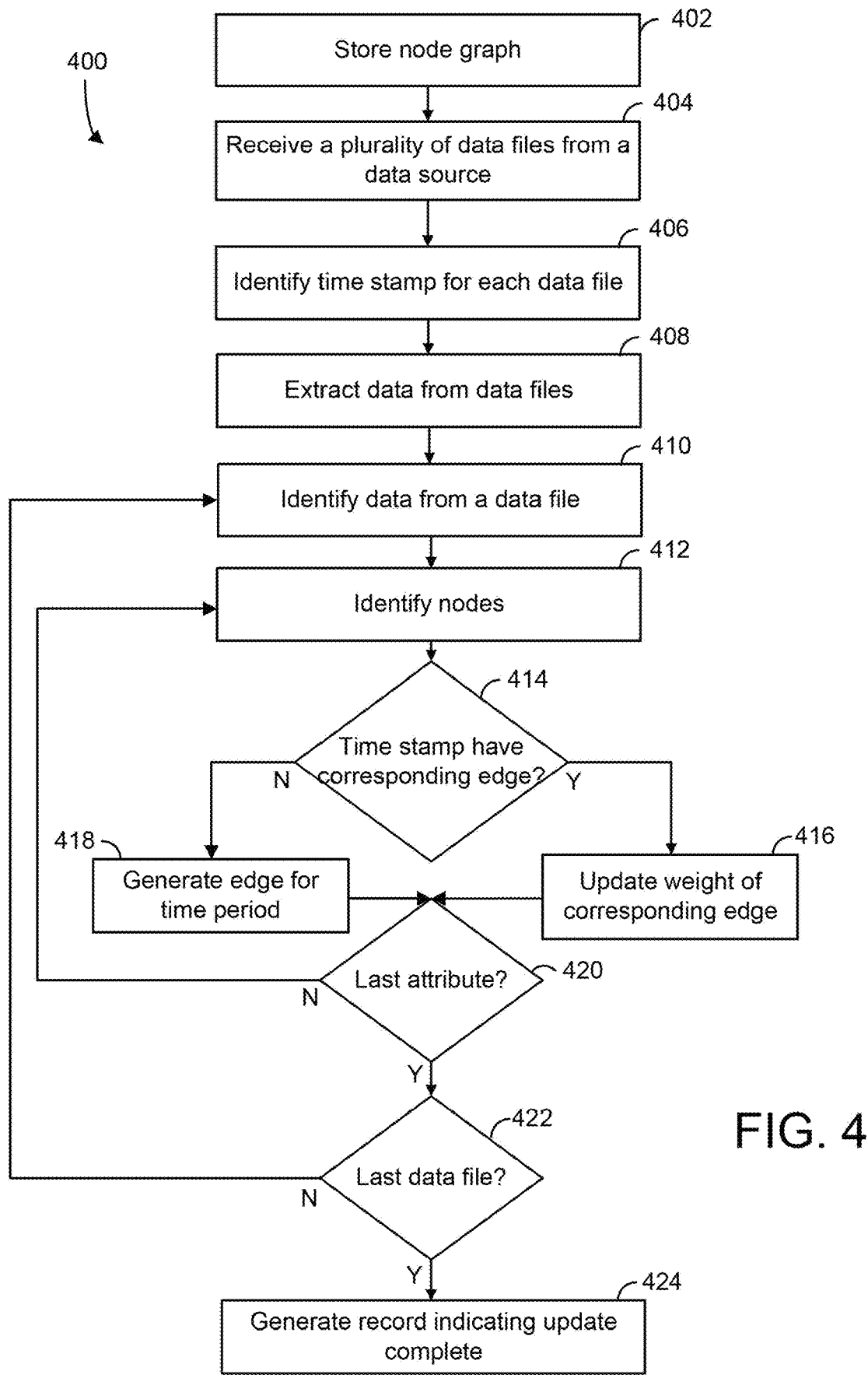
FIG. 4 is an example method for generating a node graph data structure to maintain historical data, in accordance with some embodiments.

Referring now to FIG. 4, an example method 400 for updating a node graph data structure is shown, in accordance with some embodiments. Method 400 can be performed by a data processing system (e.g., a client device 308, 310, or 312 or a node graph generator 314, shown and described with reference to FIG. 3, a server system, etc.). Method 400 may include more or fewer operations and the operations may be performed in any order. Performance of method 400 may enable the data processing system to store a node graph data structure in a manner in which historical data and attributes for patients for different time periods can be retrieved directly from the node graph data structure without requiring searching entries in a typical relationship database. For example, for a patient, the data processing system may receive data files from one or more data sources (e.g., clinics) that a patient visited when seeking or receiving care. The data files may be generated at the data sources and uploaded to the data processing system. The data files may include time stamps indicating when the data files were generated, the dates and times in which the patient visited the data sources, or the dates and times in which the data sources transmitted the data files to the data processing system. The data processing system may identify the patient's name, time stamps, and attributes from the data files and identify the patient node and attribute nodes that correspond to the identified data in the node graph data structure. The data processing system may identify edges between the patient nodes and the attribute nodes that correspond to time periods that include the time stamps of the data files. The data processing system may update weights (e.g., strengths scores) of the edges based on the data files containing identifications of the attributes according to a set of criteria. The data processing system may generate a record indicating the node graph data structure update is complete upon updating the node graph data structure based on each of the data files. In this way, the data processing system may store a history of data in a node graph data structure that can be used to retrieve data about patients from different time periods, which would otherwise be difficult or impossible in graphs that only contain single edges between nodes.

At operation 402, the data processing system stores a node graph data structure. The data processing system may store the node graph data structure as a database in memory such that the data processing system may retrieve data from the node graph data structure upon receipt of a request. The node graph data structure may be a graph database with individual node graph data structures (e.g., nodes) that identify different entities or patients (e.g., entity or patient nodes), attributes of patients (e.g., attribute nodes), clinics (e.g., clinic or group entity nodes), lab results, and other types of nodes. Each node in the node graph data structure may include a string identifier of the patient, attribute, or clinic the node represents or with which the node is associated. As described herein, for succinctness references to attribute nodes may be references to clinic nodes, lab result nodes, and any other non-patient or entity nodes.

The node graph data structure may also include edges between nodes that have a relationship with each other. For example, if a particular patient visited a clinic and was diagnosed with a disease during the visit, the node graph data structure may store an edge between the patient node for the patient and a clinic node for the clinic and an edge between the patient node and an attribute node for the disease. In some cases, the node graph data structure may also store an edge between the clinic node and the attribute node for the disease that indicates the disease was diagnosed at the clinic. Continuing with the example, if the patient visited another clinic and received the same diagnosis, the patient's node may have an edge with a clinic node for the second clinic and the clinic node may have an edge with the attribute node for the diagnosis. The nodes in the node graph data structure may have any number of edges with each other in the node graph data structure.

In some embodiments, the nodes of the node graph data structure may be stored at coordinates in the node graph data structure and the edges may be stored as vectors. For example, a node may have coordinates in the form of (x,y) or (x,y,z) that indicate the position of the node in the node graph data structure and an edge may be a vector in the form of <x,y> or <x,y,z> with corresponding coordinates at at least one end of the vector as a position of the edge in the node graph data structure. As nodes or edges are added to the node graph, the data processing system may insert the edges and nodes at different positions.

In some embodiments, in addition to the edges between nodes, the node graph data structure may include relationship types of the edges. The node graph data structure may store the relationship types in data structures that are dedicated to the individual edges. The node graph data structure may store the relationships in data structures that are dedicated to the individual edges. The relationship types may indicate the types of relationships the nodes have with each other. For example, a patient node for a patient may have an "is associated with" relationship type with a zip code node if the patient lived in the zip code represented by the zip code node. Other examples of relationship types include "has an active consent form," "pertains to," "has treatment relationship with," "assigned to," "declared by," "has payment relationship with," "is in," "is diagnosed with," "is diagnosed by," "lives at," "can be contacted at," "previously had treatment relationship with," etc. When retrieving data from the node graph data structure, the data processing system may additionally retrieve the relationship data from the data structures of the edges and include the relationship data to provide context for the attributes.

In some embodiments, the node graph data structure may include weights for the edges between the nodes. The weights may be stored in the data structures for the edges. The weights may indicate the likelihood that the individual edges are correct. For example, a patient node may share an edge with a clinic node. The edge may have a weight (e.g., a value or strength score) on a scale (e.g., a scale from 1-100, a log scale, a natural log scale, etc.) that indicates the probability that the edge is correct and the patient has a relationship with the clinic. The weight may be based on "evidence" the data processing system receives indicating the relationship between the patient node and the clinic node is correct. Evidence may be or include individual documents that include indications of the clinic and the patient, such as a document that includes both a string containing the patient's name and a string containing the name of the clinic. The data processing system may identify pieces of evidence, assign scores to the pieces of evidence based on the type of documents and/or the source or source types from which the evidence was received, as described below, and aggregate the scores together to obtain an aggregated score or the weight. In some embodiments, the data processing system may calculate the weight from the aggregated score by performing another operation on the score, such as performing a natural log operation on the score. In doing so, the data processing system may create a weight cap to stop the weights from increasing too much and to better control the weights of edges.

The data processing system may update the weights for the edges over time as the data processing system receives data indicating the edge is correct. For example, the node graph data structure may store an edge between a patient node for a patient and a zip code node for a zip code indicating the patient lives in the zip code. The weight for the edge may be 20 out of 100 because the data processing system may not have a significant amount of evidence that indicates the patient lives at the zip code. The data processing system may receive a document file from a clinic with the patient's name and the zip code on it. The data processing system may identify the name and the zip code on the file and increase the weight for the edge based on the new document file that includes both the patient's name and the zip code. The data processing system may continuously update the edge over time to increase the weight of the edge. By doing so, the data processing system may enable users to query the node graph data structure for data based on edges having weights above a defined threshold, therefore reducing the risk that the data processing system retrieves inaccurate data. The data processing system may similarly maintain and update any number of weights for edges between nodes.

In some embodiments, the node graph data structure may include multiple edges between a single pair of nodes. Each of the edges may be dedicated to data from a different overlapping or non-overlapping time period. For example, a patient node may share edges for different months with a diagnosis node. In some embodiments, the patient node may also have an edge for the "lifetime" of the relationship between the two nodes. Each of the edges may have its own weight indicating the likelihood that the relationship between the two nodes for the time period of the edge is correct.

The data processing system may update the weights for the edges based on the times in which the data files are received, the times in which the data files are generated, or the times in which the data files are transmitted. For example, upon receiving a data file, the data processing system may identify a time stamp of the data file from an electronic document in the data file (e.g., identify a time on the electronic document using object character recognition techniques), a time in which the data processing system received the data file, or a time stamp from the body or header of the data packet that contains the data file. The data processing system may identify a patient node and attribute nodes based on the nodes having identifiers that match the data in the data file. For each identified attribute node, the data processing system may identify the edges between the patient node and the attribute node and compare the time stamp with the time periods of the edges. Based on the comparison, the data processing system may identify the edge that is associated with a time period that encompasses the time stamp (e.g., includes the time and/or date of the time stamp) and increase the weight of the edge based on the data file containing data corresponding to the patient node and attribute node for the time period. In some embodiments, the data processing system may additionally update an edge containing the weight for the lifetime of the relationship between the patient node and the attribute node based on the data. The node graph data structure may similarly update edges between the patient node and other attributes that the data processing system updated based on data in the data file. In this way, the data processing system may maintain a binned history of the data the data processing system collects from clinics that can be used to retrieve data based on searches for data from different time periods.

At operation 404, the data processing system receives a plurality of data files from a data source. The data processing system may receive the plurality of data files from a data source such as a client device at a clinic. The data files in the plurality of data files may correspond to different visits by patients at the clinic. For example, over the course of a day, multiple patients may visit a clinic for care. A clinician may speak to the patients and upload documents to a computer at the clinic indicating the clinician's diagnoses for the patients and other data generated from the visit. The computer may store the documents as data files in memory and transmit the data files to the data processing system.

Computers at clinics may transmit any type of documents as data files to the data processing system. Examples of types of documents the computers may transmit include, but are not limited to, ADT's, CCDA documents, SOH documents, attribution files, and pre-adjudicated claims. In some cases, different types of clinics may transmit different types of documents (e.g., an emergency clinic may generate and transmit different types of documents or documents with different types of data than a dermatology clinic). The documents may be stored in the data files as text documents and/or may include images.

In some embodiments, the data processing system may store data files the data processing system receives from clinics in a separate database, such as a relational database. The data processing system may store the data files with time stamps indicating the times and/or dates the data processing system received the data files, the data files were generated, and/or the data files were transmitted. In some embodiments, the data processing system may also store identifications of the individuals for which the data files include information. In some embodiments, the data processing system may also store unique numerical or alphanumerical identifiers of the data files that can be used to quickly look up the respective data files.

At operation 406, the data processing system identifies time stamps for each of the data files. The data processing system may identify the time stamps for the data files by identifying the times in which the data files are received, the times in which the data files are generated, or the times in which the data files are transmitted, depending on the configuration of the data processing system. For example, when the data processing system is configured to identify time stamps for the data files by identifying the times in which the data files are received, the data processing system may identify the time the data processing system received the data from an internal clock and store an association between the identified time and the data file in an internal database (e.g., a relationship database). In another example, when the data processing system is configured to identify the times in which the data files are transmitted, the data processing system may identify time stamps in the bodies or headers of the data packets that include the data files and store associations between the identified times and the data files in the database. In yet another example, when the data processing system is configured to identify the times in which the data in the data files was generated, the data processing system may use object recognition techniques and/or natural language processing techniques to identify times and/or dates in the text of the data files and store associations between the identified times and/or dates and/or the data files in the database.

At operation 408, the data processing system extracts data from data files. The data processing system may extract data from the data files using natural language processing techniques and/or object recognition techniques. For example, the data processing system may extract data from the data files by identifying patient names, patient attributes, medical diagnoses, clinic names, and other types of data from the data files. In some embodiments, the data processing system may identify the data in the data files responsive to the data matching stored values in memory of the data processing system. The data processing system may extract the data as key words such that the data processing system may compare the data to values of nodes in the node graph data structure to determine whether to generate new edges or update weights of the edges in the node graph data structure.

At operation 410, the data processing system identifies data from a data file. The data processing system may identify data from the data file by identifying the file or location in memory that contains the extracted data from the data file. For example, the data processing system may scan the files of extracted data or the places in memory that contain the extracted data. The data processing system may identify a file or location in memory from which the data processing system has not previously retrieved data to use to update the node graph data structure.

At operation 412, the data processing system identifies nodes from the node graph data structure. In identifying the nodes, the data processing system may first identify the patient nodes that correspond to the patients for which the data of the data file was generated. To do so, the data processing system may identify an extracted name value from the data file. The data processing system may determine the extracted name value is a name versus another type of value by comparing the extracted value to a database with strings of possible names. If the data processing system determines the extracted name value matches a string in the database of possible names, the data processing system may determine the value is a name. Upon determining the value is a name, the data processing system may label the data file from which the name value was extracted with an identification of the name to indicate the data from the data file is associated with the name. In this way, the data processing system may identify the name of the patient that is associated with the data file.

In some embodiments, instead of or in addition to identifying the name from the data file, the data processing system may identify a common key for the data file. The common key may be a unique alphanumerical identifier for the patient. The data processing system may identify the common key for the data file by extracting the common key from the data file itself. The data processing system may also identify the common key by performing identity resolution or authentication on the data. The data processing system may authenticate the identity of the person identified in the document and identify the common key for the person, such from an index or database.

Upon identifying the name value for the data file, the data processing system may identify the patient node that corresponds to the name. The data processing system may identify the patient node that corresponds to the name by querying the patient nodes in the node graph data structure for values that match the name value. The data processing system may identify a patient node for the data file responsive to the patient node having a matching string to the name value.

The data processing system may identify attribute nodes (or any other type of nodes) in the node graph data structure that correspond to the other values from the data file. For example, the data processing system may compare the extracted values from a data file to the non-patient nodes (e.g., attribute nodes) of the node graph data structure. The data processing system may identify any of the attribute nodes that have matching values to the extracted values. Together, an attribute node that has a relationship with a patient node may be a patient node-attribute node pair.

At operation 414, the data processing system determines whether the time stamp of the data file has a corresponding edge between the identified patient node and the identified attribute nodes. For example, after identifying the patient node and the attribute nodes for the data file, the data processing system may identify the edges in the patient node-attribute node pairs. The data processing system may identify the time periods that correspond to each of the edges and compare the time and/or date of the time stamp with the time periods. Based on the comparison, for each patient node-attribute node pair, the data processing system may determine if the patient node-attribute node pair contains an edge with a time period that includes the time. If the data processing system does not identify an edge with a time period that includes the time for a patient node-attribute node pair, the data processing system may determine the time stamp does not have a corresponding edge between the patient node and the attribute node of the patient node-attribute node pair. If the data processing system identifies an edge with a time period that includes the time stamp for a patient node-attribute node pair, the data processing system may determine the time stamp does have a corresponding edge between the patient node and the attribute node of the patient node-attribute node pair.

For each patient node-attribute node pair with an edge that corresponds to the time stamp, at operation 416, the data processing system updates a weight of the corresponding edge. For example, the data processing system may identify the weight of the corresponding edge from the node graph data structure. The data processing system may identify the weight of the edge which may be stored in memory as an attribute of the edge with a list or count of data files that have been used to update the edge. The data processing system may update the list by storing an identification of the data file in the edge attribute or incrementing the counter to indicate another data file contains evidence that the patient node is linked to the attribute node. The data processing system may then update the weight by calculating a new weight by aggregating the new data file with the data files that were previously used to update the weight.

In some embodiments, the data processing system may update the weight of the edge by assigning a weight to the data file. For example, the data processing system may assign a weight to the data file based on the type of document in the data file and/or the source of the data file. Different types of data files may be associated with different weights. For example, ADTs may be associated with a higher weight than CCDAs which may be associated with a higher weight than SDOH surveys. The data processing system may store weights for any number of types of data files and the weights may be in any order between document types. The data processing system may identify the type of document from the data in the document or from a document type in the data file that contains the document. Similarly, the data processing system may store weights for different data sources. For example, hospitals may be associated with higher weights than family practice clinics, which may have higher weights than community health organizations, etc. The data processing system may store weights for any number of types of data sources. The data processing system may aggregate, multiply, or perform any type of operation on the two weights for the data file to obtain an evidence weight for the data file and aggregate the evidence weight with the previously stored weight for the edge to obtain an aggregated weight. In some embodiments, the data processing system may then calculate the natural logarithm of the aggregated weight to obtain a new weight for the edge. Accordingly, the data processing system may take into account the evidence of the relationship between the attribute node and the patient node in the weight of the edge for the corresponding time period to the time stamp of the data file. The data processing system may similarly update the weights of edges for any number of data files.

For each patient node-attribute node pair without an edge that corresponds to the time stamp, at operation 418, the data processing system generates an edge for a time period that includes the time and/or date of the time stamp. The data processing system may generate the time period to have a predefined length. In some embodiments, the data processing system may store a series of defined time periods in memory. Upon determining there is not an edge between the patient node and the attribute node of the patient node-attribute node pair that corresponds to a time period including the time and/or date of the time stamp, the data processing system may query memory for a time period that is inclusive of the time and/or date of the time stamp. Upon identifying the time period, the data processing system may insert an edge between the patient node and attribute node of the patient node-attribute node pair and retrieve and insert the identified time period as an attribute of the new edge. The data processing system may then calculate a weight for the edge based on the document type and/or source of the data file that caused the data processing system to generate the edge as described above. In this way, the data processing system may maintain a dynamic node graph data structure that can store an increasing amount of data in a time-organized fashion.

At operation 420, the data processing system determines if the attribute of the patient node-attribute node pair is the last attribute for which to store data from the data file. The data processing system may identify the data the data processing system extracted from the data file and determine if all of the data had been matched to a patient node-attribute node pair. If the data processing system identifies a new word or phrase that matches an attribute node, the data processing system may repeat operations 412 until determining there is not any more data to use from the data file to update the node graph data structure.

At operation 422, the data processing system determines if the data file is the last data file. The data processing system may determine if the data file is the last data file by examining the batch of files for which the data processing system is processing data. If the data processing system determines there is another data file in the batch from which data was extracted in operation 408, the data processing system may identify the data file and repeat operations 410-422 until determining there are not any further data files to use to update the node graph data structure.

At operation 424, the data processing system generates a record indicating the update to the node graph data structure is complete for the batch of data files. The record may be an indication on a user interface that the data processing system transmits to an administrative computer to indicate the data has been uploaded. In some embodiments, the data processing system may generate the record to indicate a list of the updates the data processing system made as a result of the batch upload. The data processing system may store such a record in memory. Accordingly, the data processing system may maintain an active record of updates the data processing system makes to the node graph data structure.

Figure 5:
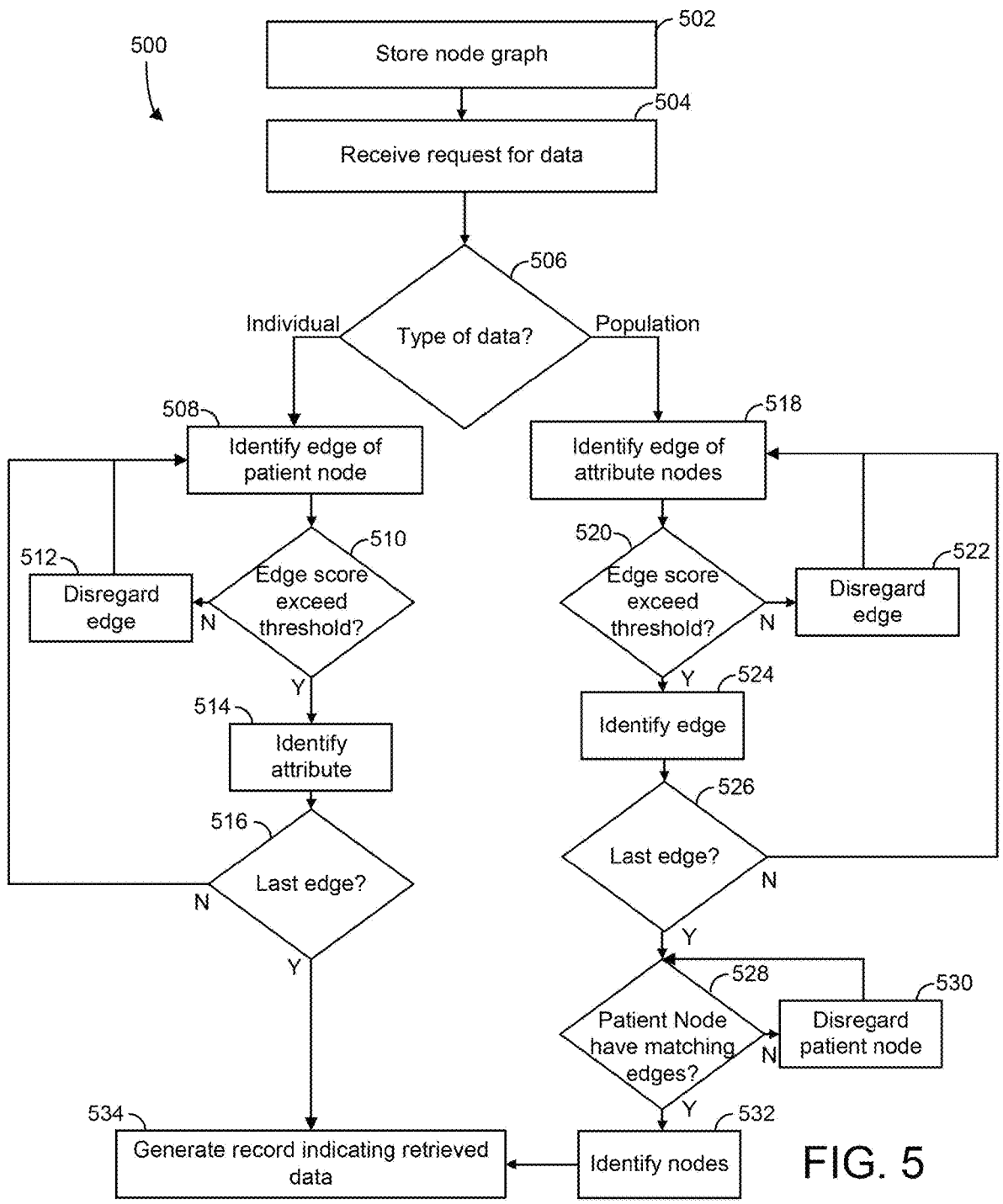
FIG. 5 is an example method for retrieving data from a node graph data structure, in accordance with some embodiments.

Referring now to FIG. 5, an example method 500 for retrieving data from a node graph data structure is shown, in accordance with some embodiments. Method 500 can be performed by a data processing system (e.g., a client device 308, 310, or 312 or a node graph generator 314, shown and described with reference to FIG. 3, a server system, etc.). Method 500 may include more or fewer operations and the operations may be performed in any order. Performance of method 500 may enable the data processing system to store a node graph data structure in a manner in which a user can transmit a request to the data processing system for individual or population data and the data processing system may quickly retrieve the data from the node graph data structure without searching entries in a typical relationship database. For example, the data processing system may store a node graph data structure that contains data in patient nodes and attribute nodes. The data processing system may receive a request about an individual patient. The data processing system may identify the patient node for the individual patient and retrieve data from the attribute nodes that have edges with the patient node. The data processing system may instead receive a request for a population that has a certain set of attributes. The data processing system may identify the attribute nodes that correspond to the set of attributes in the request and identify the patient nodes that have edges with each of the identified attributes. The data processing system may transmit the identified data to the requesting client device. In this way, the data processing system may store and retrieve data without querying an entire database of entries to respond to a request.

At operation 502, the data processing system stores a node graph data structure. The data processing system may store the node graph data structure in a similar manner to how the data processing system stores the node graph data structure in operation 402, as described with reference to FIG. 4.

At operation 504, the data processing system receives a request for data. The request for data may be a request for data about a particular patient or a request for data about patients that have a certain set of attributes. For example, the request may include a string identification of a patient (e.g., the patient's name) in a data packet. In this example, the data processing system may process the request as a request for data about the patient. In another example, the request may include string identifications of attributes (e.g., a set of attributes). In this example, the request may be for a population list of patients that share each of the attributes. Based on either of the example requests, the data processing system may query the node graph data structure for the requested data.

At operation 506, the data processing system determines a type of data being requested. The data processing system may make this determination based on the context of the data in the body of the request. The types of data that may be requested are data (e.g., attributes) about a particular individual or patient and/or data about patients (e.g., a list of individuals or patients) that share a requested set of attributes. The data processing system may determine the type of data being requested by identifying the data in the request. If the data processing system identifies a single name of a patient (or any number of names of patients) in the request, the data processing system may determine the request is for data about the named patient (or named patients). If the data processing system identifies a list of attributes in the request, the data processing system may determine the request is for data about a population that includes the attributes.

Responsive to determining the request is for data about individual patients, at operation 508, the data processing system identifies edges of a patient node that corresponds to the named patient. To do so, the data processing system may query the node graph data structure using the name in the query. The data processing system may identify a patient node that contains the name. The data processing system may then identify an edge that connects the patient node to another node (e.g., an attribute node).

At operation 510, the data processing system determines if the identified edge has a weight that exceeds a threshold. The threshold may be a value that the requesting client device includes in the request or a stored value in memory of the data processing system. The threshold may indicate a minimum level of confidence that the two nodes should be linked. The data processing system may compare the weight of the edge to the threshold. If the data processing system determines the weight of the edge is less than the threshold, at operation 512, the data processing system disregards the edge (e.g., does not retrieve the attribute of the attribute node attached to the edge). However, if the data processing system determines the weight of the edge is equal to or greater than the threshold, at operation 514, the data processing system identifies the attribute of the attribute node attached to the edge. Accordingly, the data processing system may only retrieve attributes to include in a response to a request for data about a patient for which the data processing system has enough evidence to satisfy a threshold in the request or a locally stored threshold.

At operation 516, the data processing system determines if the identified edge is the last edge connected to the patient node. The data processing system may do so by scanning the patient node for edges. If the data processing system identifies another edge from the scan, the data processing system may repeat operations 508-516 until the data processing system does not identify an edge connected to an attribute node for which the data processing system has not evaluated or otherwise retrieved from memory.

In some embodiments, the data processing system may only identify edges that correspond to a time period that includes a date or time identified in the request. For example, the data processing system may receive a request for data about a patient from a specific time period or from a particular time. The data processing system may receive such a request, for example, when a physician is seeking to look at the medical history of a patient and seeks to see previous vital signs or prior illnesses that a patient has had. Upon receiving the request, the data processing system may identify a patient node in the node graph data structure that corresponds to the patient identified in the request and identify the edges the patient node shares with other nodes. The data processing system may identify the edges that correspond to the time period or time stamp included in the request. The data processing system may compare the weights of identified edges to a threshold to determine which attributes to identify and use in response to the request. The requests may include identifications of one or more time stamps and time periods in addition to or instead of requests for attributes that correspond to a "lifetime" edges that includes a weight calculated for the lifetime in which the patient node and the attribute node have a relationship. Accordingly, the data processing system may store and provide historical information to inquiring clinicians to enable the clinicians to request historical information about patients.

If at operation 506 the data processing system determines the type of data is for a population that has a particular set of attributes, at operation 518, the data processing system first identifies the edges of attribute nodes of the node graph data structure that correspond to the set of attributes included in the request. To do so, the data processing system may query the node graph data structure using names of the attributes in the query. The data processing system may identify the attribute nodes that contain the strings identifying the attributes. The data processing system may then identify an edge that connects an attribute node to a patient node.

At operation 520, the data processing system determines whether a weight of the edge exceeds a threshold. The data processing system may determine whether the weight of the edge exceeds the threshold in a similar manner to how the data processing system determined whether a weight of an edge exceeds a threshold in operation 510. If the data processing system determines the weight exceeds the threshold, at operation 522, the data processing system may disregard the edge (e.g., not store in random access memory). However, if the data processing system determines the weight of the edge exceeds the threshold, at operation 524, the data processing system identifies (e.g., retrieve and temporarily store in random access memory) an identification of the edge. Accordingly, the data processing system may only retrieve attributes to include in response to a request for data about a patient for which the data processing system has enough evidence to satisfy a threshold in the request or a locally stored threshold.

At operation 526, the data processing system determines if the identified edge is the last edge connected to the attribute nodes for the attributes identified in the request. The data processing system may do so by scanning attribute nodes for edges the data processing system identified in response to the request but has not yet evaluated against a threshold. If the data processing system identifies another edge from the scan, the data processing system may repeat operations 518-528 until the data processing system does not identify an edge connected to an attribute node for which the data processing system has not evaluated or otherwise retrieved from memory.

At operation 528, the data processing system determines if a patient node has edges with each of the attribute nodes that were identified in response to the request. The data processing system may identify a patient node in the node graph data structure in response to determining the patient node has at least one edge that the data processing system determined has a weight satisfying the threshold. Upon identifying the patient node, the data processing system may identify each of the attribute nodes that correspond to the attributes from the request and determine whether the patient node has an edge with each of the attribute nodes. If the data processing system determines there is at least one attribute node with which the patient node does not have an edge, at operation 530, the data processing system disregards the patient node. If the data processing system determines the patient node has an edge with all of the attribute nodes, however, at operation 532 the data processing system identifies the patient node. Although not shown, the data processing system may repeat operations 528-532 for each patient node that has at least one edge with the attribute nodes identified based on the request until the data processing system has evaluated each of such patient nodes. In this way, the data processing system may identify a population of patients that have a requested set of attributes using a node graph data structure.

At operation 534, the data processing system generates a record (e.g., a file, document, table, listing, message, notification, etc.) indicating the data the data processing system retrieved in response to receiving the request. For example, if the data processing system retrieved data about a particular patient, the data processing system may generate a list of attributes associated with attribute nodes that have edges with a patient node for the patient and satisfy criteria included in the request in a record. In another example, if the data processing system retrieved data about a population of patients that have a defined set of attributes, the data processing system may generate a list of patients associated with patient nodes that have edges with attribute nodes that are associated with the requested attributes. The data processing system may transmit the record to the requesting client device in a data packet and/or as a user interface such that a user accessing the requesting client device can view the retrieved data. In this way, the data processing system may use a node graph data structure to store and retrieve data received from different clinics to provide data to requesting users.

Figure 6:
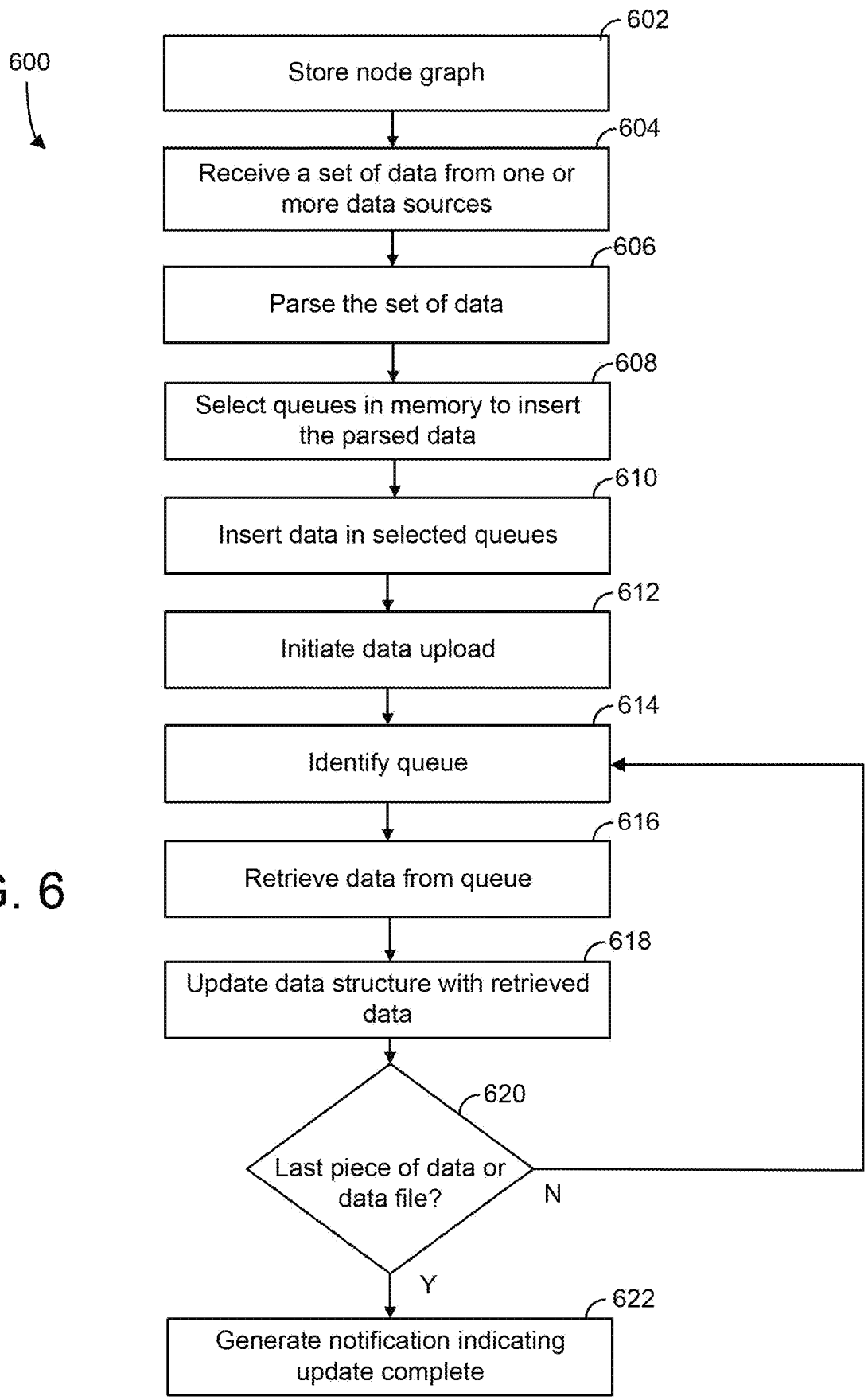
FIG. 6 is an example method for updating a data structure using a prioritized queuing system, in accordance with some embodiments.

Referring now to FIG. 6, an example method 600 for updating a data structure (e.g., a node graph data structure) using a prioritized queuing system is shown, in accordance with some embodiments. Method 600 can be performed by a data processing system (e.g., a client device 308, 310, or 312 or a node graph generator 314, shown and described with reference to FIG. 3, a server system, etc.). Method 600 may include more or fewer operations and the operations may be performed in any order. Performance of method 600 may enable the data processing system to update a data structure in a manner that enables high priority information to be available more quickly to users accessing the data structure than lower priority information. For example, the data processing system may store a node graph data structure that contains data for different patients as described herein. The data processing system may receive a set of data from one or more data sources. The data processing system may parse the data to determine the different types of the data and the sources of the data. The data processing system may insert the parsed data into queues in memory according to selection criteria. The queues may be prioritized queues that are each dedicated to storing different sets of data based on the importance that the data is shareable quickly. The data processing system may then retrieve the data from the queues according to the priority of the queues (e.g., retrieve data from the high priority data first followed by the next highest priority queue, etc.). The data processing system may then add the data from the queues to the data structure in the order in which the data was retrieved from the queues. In this way, the data processing system may enable certain types of data (e.g., PHI) shareable more quickly than other types of data (e.g., demographic data) to ensure the high priority data is available for retrieval faster than lower priority data, which may useful if a physician requests health information about a patient that was recently uploaded to the data structure.

At operation 602, the data processing system stores a node graph data structure. The data processing system may store the node graph data structure in a similar manner to how the data processing system stores the node graph data structure in operation 402, as described with reference to FIG. 4. In some embodiments, instead of or in addition to storing a node graph data structure, the data processing system may store another type of data structure.

At operation 604, the data processing system receives a set of data from one or more data sources. The data sources may be computers of different types of clinics or healthcare providers. The set of data may include different entries of data that clinicians at the clinics or healthcare providers create to indicate attributes about patients that visit or visited the respective clinics or healthcare providers for treatment. The set of data may include data files that each include one or more documents with handwritten or typed data about the patients. The data processing system may receive such data from any number of data sources over time via an API the data processing system may use to communicate with the data sources.

At operation 606, the data processing system parses the set of data. The data processing system may parse the set of data using natural language processing and/or object recognition techniques. For example, the data processing system may retrieve data files from the set of data and/or identify words, phrases, and/or images from the data files using natural language processing and object recognition techniques. The data processing system may extract the words, phrases, and images using such techniques and store the data in memory (e.g., random access memory) to parse the data.

In some embodiments, the data processing system may categorize the extracted data based on the type of the data. For example, the data processing system may compare the words, phrases, or images to a keyword database (e.g., a relational database) that indicates the types (e.g., PHI, provider name, demographic data, etc.) of data with which different words, phrases, or images are associated. The data processing system may identify matches between the compared data and label the different words, phrases, or images based on the matches. In this way, the data processing system may create a labeled list of the data and the type of the data that the data processing system receives from different clinics.

In some embodiments, in addition to or instead of categorizing the extracted data based on the type of the data, the data processing system may categorize the extracted data based on the data source that provided the data. For example, upon receiving a data file from a data source, the data processing system may identify the data source of the data file by identifying an identifier of the computing device that transmitted the data packet with the data file (e.g., identify an identifier in the data packet itself, an identifier that the data processing system received when establishing a connection with the computing device such as a device address, a text identifier in the data file itself, etc.). The data processing system may compare the identifier to a data source database that includes a list of data sources and their respective identifiers. The data processing system may identify the data source that provided the data file based on the data source having a matching identification to an identifier in the database. The data processing system may label the data file and/or the data the data processing system extracted from the data file with an identification of the data source. In some embodiments, the data processing system may label the data with the source type (e.g., general practice clinic, hospital, emergency clinic, orthopedic clinic, etc.) in a similar manner (e.g., compare the identifier for the data source to a database containing identifications of source types). Thus, the data processing system may maintain a record of the data sources that provided data files to the data processing system.

In some embodiments, in addition to or instead of categorizing the extracted data based on the type, source, and/or source type of the data, the data processing system may categorize the extracted data based on the file or document type of the file or document from which the data was extracted. Examples of file or document types include, but are not limited to, ADT's, CCDA's, SDOH surveys, attribution files, pre-adjudicated claims, etc. The data processing system may identify the document type or file type by using natural language processing techniques or object character recognition techniques on the documents or files and identifying language or images that correspond to the document or file type. The data processing system may then label the data extracted from the data files or documents based on the identified types.

At operation 608, the data processing system selects queues in memory to insert the parsed data. The queues may be shared or separate dedicated locations to store data in memory. Each queue may be associated with a distinct priority (e.g., high, medium, or low, or 1, 2, or 3). The data processing system may select the queues for each separate piece of data (e.g., text, phrase, or image) or for the data files themselves based on the labels the data processing system determined for the data or the data files. To do so, the data processing system may identify the labels on the data or data files. The data processing system may compare the labels to a database to identify the priorities that correspond to the labels. Upon identifying the priorities for the data or data files, at operation 610, the data processing system inserts the data or data files into the corresponding selected queues with matching priorities by storing the data or data files in the location or the queues in memory.

The data processing system may identify priorities for data or data files based on any combination of labels (e.g., data type, source, source type, document or data file type, etc.). For example, the data processing system may identify priorities for data based on the document or data file type of the data from which the data was extracted. Doing so may be advantageous in healthcare because different types of documents may have higher priority data about patients than other types of documents. For instance, an ADT may have higher priority data than and SDOH surveys because an ADT may be more likely to have PHI and/or information from ADTs may be more likely to include information that will create or significantly strengthen edges between nodes. In another example, the data processing system may identify the priorities of the individual pieces of data based on the types of data. For instance, the data processing system may identify higher priorities for PHI than for demographic data. In yet another example, the data processing system may identify the priorities of the data or the data files based on the sources or source types from which the data or data files originated. For instance, the data processing system may identify higher priorities from general practice clinics than from orthopedic clinics because general practice clinics may have more sensitive information (e.g., blood type, disease diagnoses, etc.). By prioritizing the data or data files in this manner, the data processing system may ensure higher priority information is available for retrieval from the data structure earlier than lower priority data, enabling physicians to have access to PHI faster to help the physicians make more accurate diagnoses.

At operation 612, the data processing system initiates a data upload of the extracted data. The data processing system may do so by starting to retrieve data from the queues to upload into the data structure. The data processing system may initiate the data upload using a batch processing or continuous processing technique.

At operation 614, the data processing system identifies a queue from which to retrieve data. The data processing system may identify the queue according to a stored set of criteria. For instance, the data processing system may store a set of rules that indicate an order of queues from which to retrieve data. The rules may indicate to retrieve data from the queues in sequential order (e.g., retrieve all of the data from the highest priority queue, then from the next highest priority queue, etc.), retrieve a defined amount of data (e.g., a defined number of attributes) from each queue in a defined sequence and then repeating the sequence, or according to any other rules. The data processing system may identify a queue according to the set of criteria.

After identifying the queue, at operation 616, the data processing system retrieves data from the queue. The data processing system may retrieve data from the queue in the order in which the data was stored. For example, when storing the data in the queue, the data processing system may store time stamps with the data to indicate the time in which the data was stored. The data processing system may query timestamps in the queue and identify the data that is associated with the earliest time stamp and retrieve the identified data.

At operation 618, the data processing system updates the data structure with the retrieved data. The data processing system may update the data structure by adding the retrieved data to the data structure. In some embodiments, the data processing system updates the data structure by updating a node graph data structure in a similar manner to the manner described with respect to method 400, shown and described with reference to FIG. 4.

At operation 620, the data processing system determines if there is any more data to retrieve to update the data structure. The data processing system may do so by querying the queues according to the stored set of criteria. For example, upon updating the data structure in operation 618, the data processing system may identify the next queue from which to retrieve data according to the stored criteria. The data processing system may query the queue for data, and if there is a piece of data in the queue, repeat operations 618-620 to retrieve and update the data structure with the data from the queue. If there is not any data left in the queue, the data processing system may identify the next queue according to the stored criteria (e.g., the next queue in a sequence or the queue with the next highest priority) and query the next queue for data. The data processing system may continuously repeat operations 614-620 until the data processing system determines there is not any more data to retrieve in the queues.

Upon determining there is not anymore data to retrieve from the queues, in operation 622, the data processing system generates a notification indicating the update is complete. The notification may be a record that includes a list of data the data processing system uploaded to the data structure. The data processing system may transmit the notification to an administrator device to indicate the data from the data files has been successfully uploaded to the data structure and is available for sharing.

Figure 7:
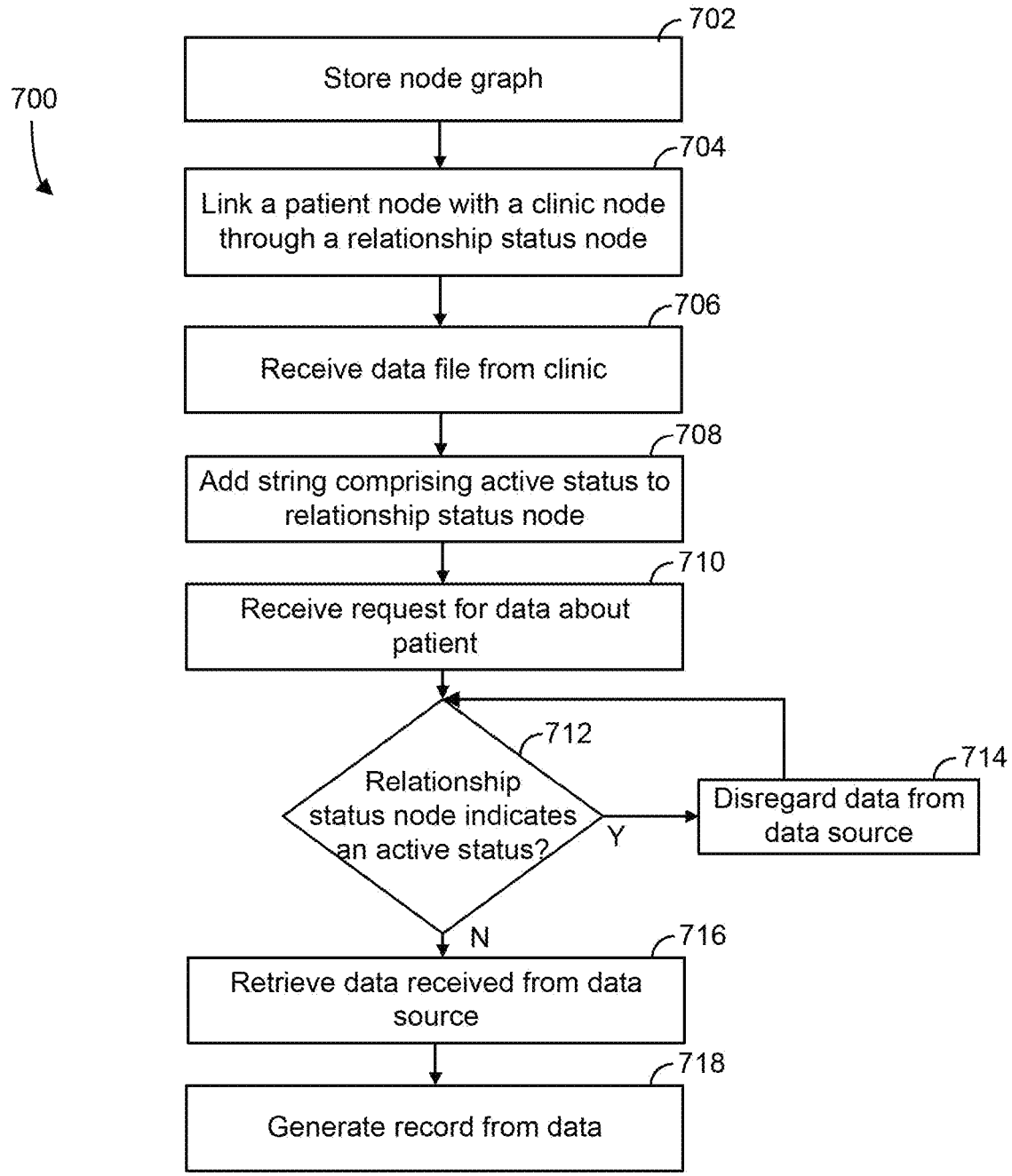
FIG. 7 is an example method for maintaining a clinic care status node in a node graph data structure, in accordance with some embodiments.

Referring now to FIG. 7, an example method 700 for maintaining a clinic care status node in a node graph data structure is shown, in accordance with some embodiments. Method 700 can be performed by a data processing system (e.g., a client device 308, 310, or 312 or a node graph generator 314, shown and described with reference to FIG. 3, a server system, etc.). Method 700 may include more or fewer operations and the operations may be performed in any order. Performance of method 700 may enable the data processing system to use a node graph data structure to retrieve accurate sets of data in a manner that enables the data processing system to avoid retrieving stale or inaccurate data. For example, the data processing system may store a node graph data structure that contains data for different patients as described herein. The data processing system may link a patient node with a clinic node through a relationship status node that maintains a history of the relationship between a patient and a clinic of the respective patient and clinic nodes. The data processing system may update the relationship status node over time as the data processing system goes through periods of not receiving any data from the clinic regarding the patient and periods in which the data processing system receives data from the clinic regarding the patient. The data processing system may then use the data in the status history node to determine whether to retrieve data from the node graph data structure in response to a request. In this way, the data processing system may avoid retrieving data that may be inaccurate because the data was received or identified the patient in error or the clinic does not have accurate up-to-date information about the patient so the data processing system cannot verify the data is accurate.

At operation 702, the data processing system stores a node graph data structure. The data processing system may store the node graph data structure in a similar manner to how the data processing system stores the node graph data structure in operation 402, as described with reference to FIG. 4.

At operation 704, the data processing system links a patient node with a clinic node through a relationship status node. The data processing system may link the patient node with the clinic node in response to receiving a data file from a clinic associated with the clinic node indicating a patient associated with the patient node received or is actively receiving care from the clinic. To link the patient node with the clinic node, the data processing system may generate a "relationship status" node. A relationship status node may be a node that contains a status history list indicating time periods in which a patient is actively receiving care from a clinic. The data processing system may generate the relationship status node by instantiating a relationship status node at a location in the node graph that includes a string indicating the relationship status node is a relationship status node, such as "active care" or "relationship status." The data processing system may link the relationship status node with the patient node and the clinic node.

At operation 706, the data processing system receives a data file from the clinic of the clinic node that identifies the patient and the clinic. The data processing system may receive the data file and parse the data file to determine the data file includes the identifications of the clinic and the patient.

At operation 708, the data processing system adds a string including an active status to the relationship status node. The data processing system may add the string including the "active" status to the relationship status node responsive to receiving the data file from the clinic. The data processing system may identify the status history list in the relationship status node and add strings indicating an identification of the status, a start date and/or time of the active status, and an expiration date and/or time of the active status. The data processing system may set the identification of the status as an alphanumerical character that sequentially increases for each active status the data processing system adds to the relationship status node. Because the relationship status node includes a history of active statuses that have been added, the data processing system may maintain a history indicating times in which patients received care from a patient.

In one example of performing operations 706 and 708, the data processing system uses the status relationship node to determine a time period for which to add new evidence (e.g., the time period edge for which to adjust a weight). For instance, the data processing system may determine an "as of date" as the month or time period to apply a data file (or extracted data) to use as evidence. The data processing system may do so based on the time stamp the data processing system assigned or determined for the data file. Next, the data processing system may determine a month or time period score for the time period or month according to the following formula:

LOG BASE 2(sum of monthly(evidence weight*source trust factor))

The monthly or time period evidence count (e.g., a count of the number of evidence documents the data processing system received for the month or time period) and data source count (e.g., a count of the number of data sources that provided data for the month or time period) that are stored as attributes of the edge (e.g., attributes stored in a vertex or separate data structure that stores data for the edge) may be updated based on the data file. The data processing system may also store a pointer to a separate database that stores the data file and a timestamp indicating when data from the data file was added to the node graph data structure in the attributes of the edge.

The data processing system may next evaluate the evidence to determine a status update is necessary. The data processing system may determine a status update is necessary if:

a. the relationship is currently in an active status and the expiration date calculated based on the evidence being evaluated is greater than the current active expiration date. In this case, the current active expiration date should be updated based on the new evidence according to the equation:

EXPIRATION DATE=CURRENT DATE+EVIDENCE SCORE/EVIDENCE DECAY FACTOR.

b. the relationship is not currently active and the expiration date calculated based on the evidence being evaluated is greater than the current date (e.g., the expiration date is in the future). In this case, the data processing system may create a new active status in the relationship status node with an as of date equal to the date the evidence is being processed and an expiration date equal to the expiration date calculated based on the new evidence. The expiration date may be calculated according to the equation:

EXPIRATION DATE=CURRENT DATE+EVIDENCE SCORE/EVIDENCE DECAY FACTOR.

c. The relationship is not currently active and the expiration date calculated based on the evidence being evaluated is greater than the most recent expiration date for the last expired active status (e.g., the expiration date calculated from the backdated evidence would extend the time period covered by the most recent active status even though it does not create a current active care status). This expiration date may need to be updated as it may facilitate access to more recent patient data than would be allowed by the statuses in the current status history node. The data processing system may mark the active care status as a post-dated active status (e.g., it is being applied retroactively so that it would be clear when data would have been shared and when it would not have).

In performing the above operations, the data processing system may calculate weights for individual pieces of evidence based on the evidence or source of the evidence as described herein. The data processing system may calculate the scores for the edges such that the scores do not decay directly over time, but rather are binned by time period or month. If the data processing system never receives a data file for a time period of an edge, the data processing system may not create an edge for the time period. Finally, the data processing system may track a status history independently of the weights for the individual months and indicate active periods of the relationship between two nodes. Every time evidence is submitted the evidence may be evaluated to determine if a new active status should be established or an existing expiration date updated. In this way, the data processing system may store a record of when patients received care from particular clinics and when the patients stopped receiving such care.

At operation 710, the data processing system receives a request for data about a patient. The request may include a time stamp or time period indicating times from which to retrieve data. Upon receiving the request, the data processing system may identify the patient node for the patient from the node graph data structure. The data processing system may also identify the relationship status nodes to which the patient node is linked.

At operation 712, the data processing system determines whether the relationship status node indicates an active status for the time period or a time period that includes the time stamp. For each relationship status node, the data processing system may identify active status time periods (e.g., the time between the as of date and the expiration date of the active status) and determine if the respective relationship status nodes have an active status time period that includes the time period or time stamp in the request. For any relationship status that does not include such an active status, at operation 714, the data processing system may insert a label in memory indicating not to retrieve any data from the data source for the request.

Upon identifying relationship status nodes with an active status time period containing the time period or the time stamp, at operation 716, the data processing system may retrieve data that is associated with the clinic nodes linked by the relationship node with the active status. For example, the data processing system may identify the clinic nodes that are linked to relationship nodes with an active status for the time period or timestamp in the request. The data processing system may retrieve identifications of the clinics associated with such clinic nodes to send in a response to the request, in some embodiments only responsive to determining the weight for the edge that corresponds to the requested time period or time stamp and/or the exceeds a threshold. Thus, the data processing system may retrieve a list of clinics from which the patient received active care during a requested time period.

In some embodiments, the data processing system may additionally or instead identify pointers to the data files in the edge for the time period between the patient node and the clinic node. The data processing system may identify the pointers from the edge by accessing the pointers from the attributes of the edge. The data processing system may select the pointers to access the locations of the data files from a database (e.g., a local database stored in the data processing system or a remote database stored by another computer). The data processing system may retrieve the data files and/or the name of the clinic from the clinic node.

At operation 718, the data processing system generates a record from the retrieved data. The data processing system may generate the record by creating a folder that includes the retrieved data files and/or a document indicating names of the clinics that had an active care status during the requested time period or time of the time stamp. The data processing system may then transmit the record to the requesting computing device.

Figure 8:
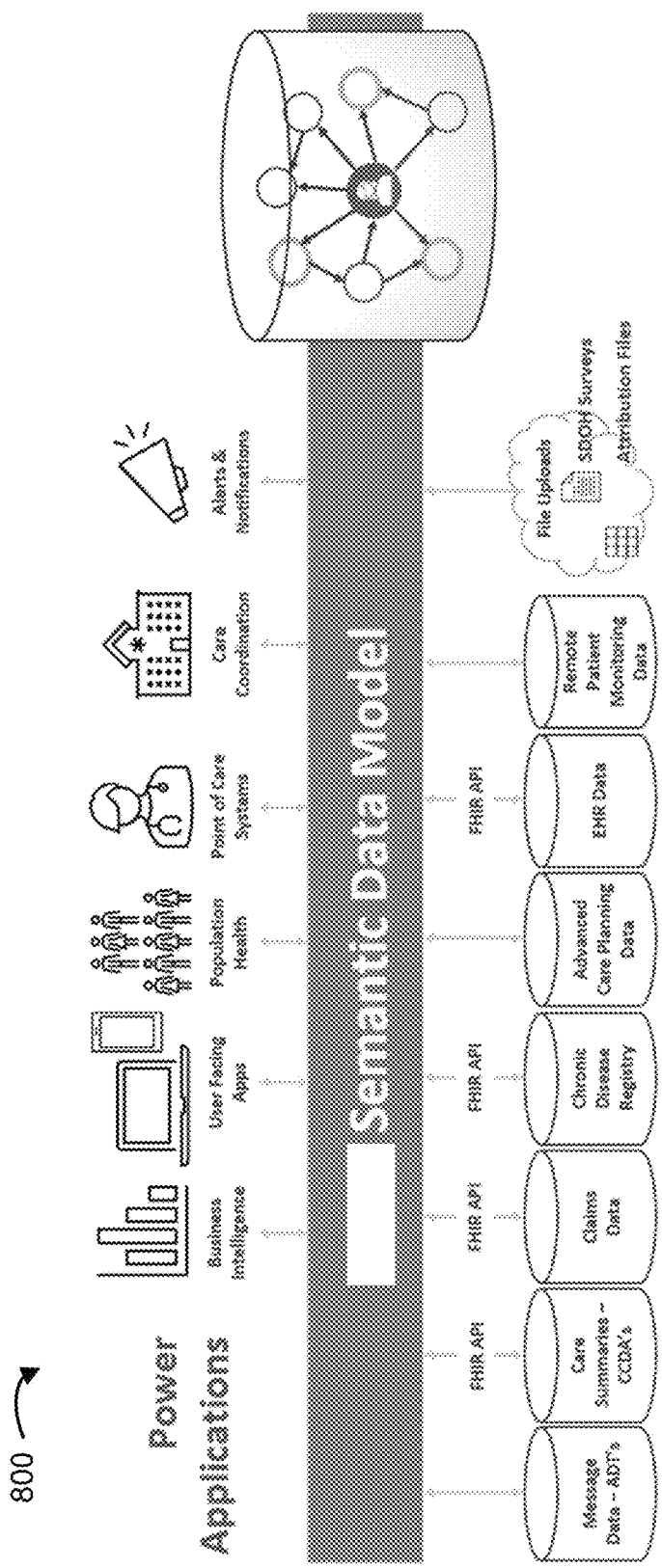
FIG. 8 is an illustration of an example semantic data model that can be used to retrieve and store data from multiple clinics in a node graph data structure, in accordance with some embodiments.

FIG. 8 is an illustration of an example semantic data model 800 that can be used to retrieve and store data from multiple clinics in a node graph data structure, in accordance with some embodiments. Semantic data model 800 may be a program or application executed by a data processing system (e.g., a client device 308, 310, or 312 or a node graph generator 314, shown and described with reference to FIG. 3, a server system, etc.) to retrieve data from different types of documents and/or sources. As illustrated, semantic data model 800 may retrieve message data, care summaries, claims data, data from the chronic disease registry, advanced care planning data, EHR data, remote patient monitoring data, etc., from data or data files stored in a database of the data processing system. Semantic data model 800 may also receive data file uploads such as SDOH surveys and/or attribution files that include data about individual patients. The data processing system may retrieve data from the stored data and/or extract data from the data files and upload the data to a node graph data structure over time to maintain an up-to-date node graph data structure.

In addition to or instead of using the data to update the node graph data structure, semantic data model 800 may communicate with computing devices at different clinics. Semantic data model 800 may receive requests for data about individual patients from computing devices at the clinics. In response to receiving the requests, semantic data model 800 may retrieve the requested data from the node graph data structure and transmit the requested data to the requesting devices. In doing so, semantic data model 800 may provide the requesting devices with business intelligence, population health information, alerts and notifications, and care coordination. Semantic data model 800 may communicate with the computing devices via user-facing applications and/or point of care systems operating on the computing devices.

Figure 9:
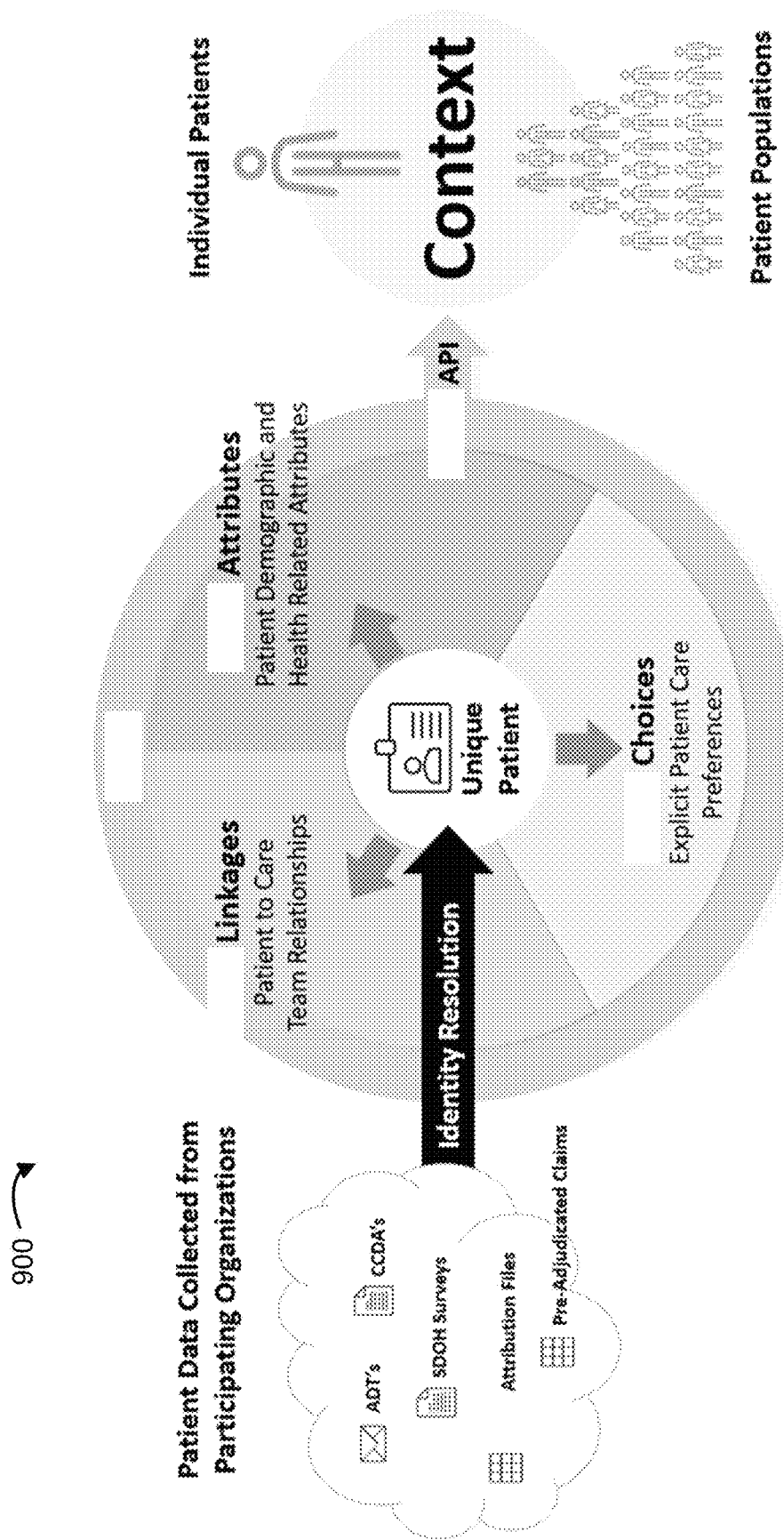
FIG. 9 is an illustration of an example sequence of uploading a data file to a node graph and using the node graph to generate patient and population data, in accordance with some embodiments.

FIG. 9 is an illustration of an example sequence 900 of uploading a data file to a node graph and using the node graph to generate patient and population data, in accordance with some embodiments. As illustrated in sequence 900, patient data can be generated at different clinics in different types of documents, such as ADT's, CCDA's, SDOH surveys, attribution files, and pre-adjudicated claims. The documents can be transmitted as or in data files to a data processing system (e.g., a client device 308, 310, or 312 or a node graph generator 314, shown and described with reference to FIG. 3, a server system, etc.). The data processing system can receive the files and update different linkages for the patients identified in the documents. In doing so, the data processing system may update the linkages (e.g., edges) to indicate different patient to care team relationships, patient demographic and health-related attributes, and explicit patient care preferences for individual patients (e.g., patient nodes for the individual patients may have edges with nodes indicating the relationships between the patients and such teams, attributes, and/or preferences). Via an API, the data processing system may then receive requests from client devices for context data about individual patients and/or patient populations. The data processing system may process the requests by querying the node graph data structure to retrieve the requested data and transmit the requested data to the requesting client devices over the API.

Figure 10:
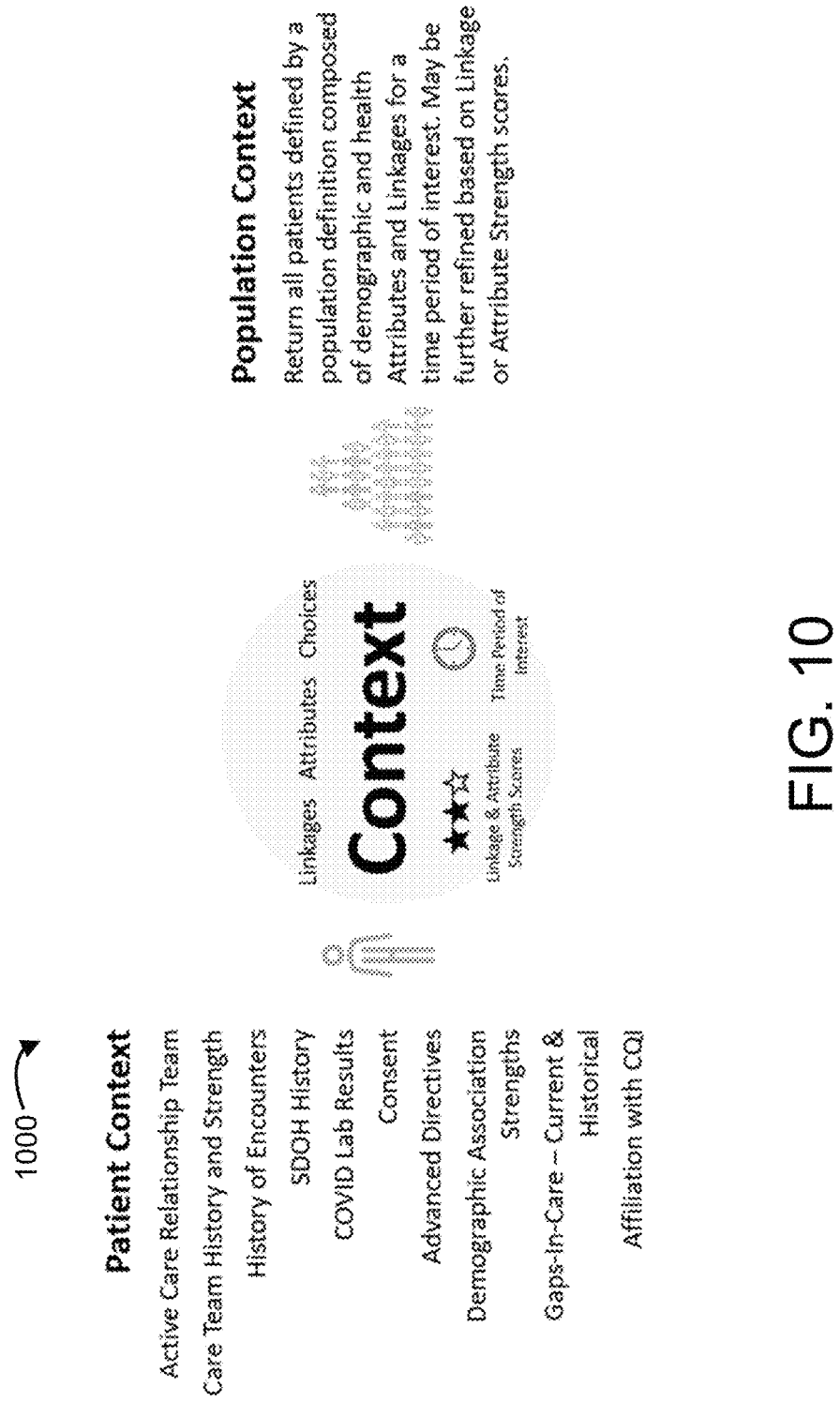
FIG. 10 is an illustration of an example query for patient and population data, in accordance with some embodiments.

FIG. 10 is an illustration of example queries 1000 for patient and population data, in accordance with some embodiments. A data processing system (e.g., a client device 308, 310, or 312 or a node graph generator 314, shown and described with reference to FIG. 3, a server system, etc.) may receive requests for data (e.g., context) about individual patients and/or populations. The requests may include identifications of a time period of interest and/or a minimum edge weight. Upon receiving such requests, the data processing system may query a node graph data structure that stores data collected from various clinics to respond to the request. Examples of requests for data about an individual patient include requests for the active care relationship team of a patient, a care team history and strength, a history of encounters, an SDOH history, COVID lab results, consent, advanced directives, demographic association strengths, gaps-in-care—current and historical, and affiliation with CQI. The data processing system may receive requests for any types of data about individual patients. Upon receipt of such requests, the data processing system may identify a patient node for the patient in the node graph data structure and identify attribute nodes that have shared edges with the patient node, that include data that corresponds to the request, and/or that meets the minimum weight and/or time period of interest included in the request. The data processing system may retrieve data from the edges with the attribute nodes and/or identifications of the attribute nodes themselves as the requested data and transmit the data back to the requesting device.

The data processing system may similarly respond to requests for data about populations. For example, the data processing system may receive a request to return a list of patients that have a defined set of health and/or demographic attributes for a time period of interest. The request may additionally include a minimum weight indicating the minimum confidence the data processing system must have that a patient has a particular attribute when compiling the requested list. Upon receipt of such a request, the data processing system may identify attribute nodes in the node graph data structure. The data processing system may identify patient nodes that have an edge with at least one of the identified attribute nodes and then reduce the identified patient nodes to patient nodes that have edges with all of the requested attributes and meet the weight/time period criteria. The data processing system may identify the patient names as strings from the patient nodes and transmit a list of the identified patient names to the requesting device, thus using the node graph data structure to retrieve a population list according to constraints provided in a request.

Figure 11A:
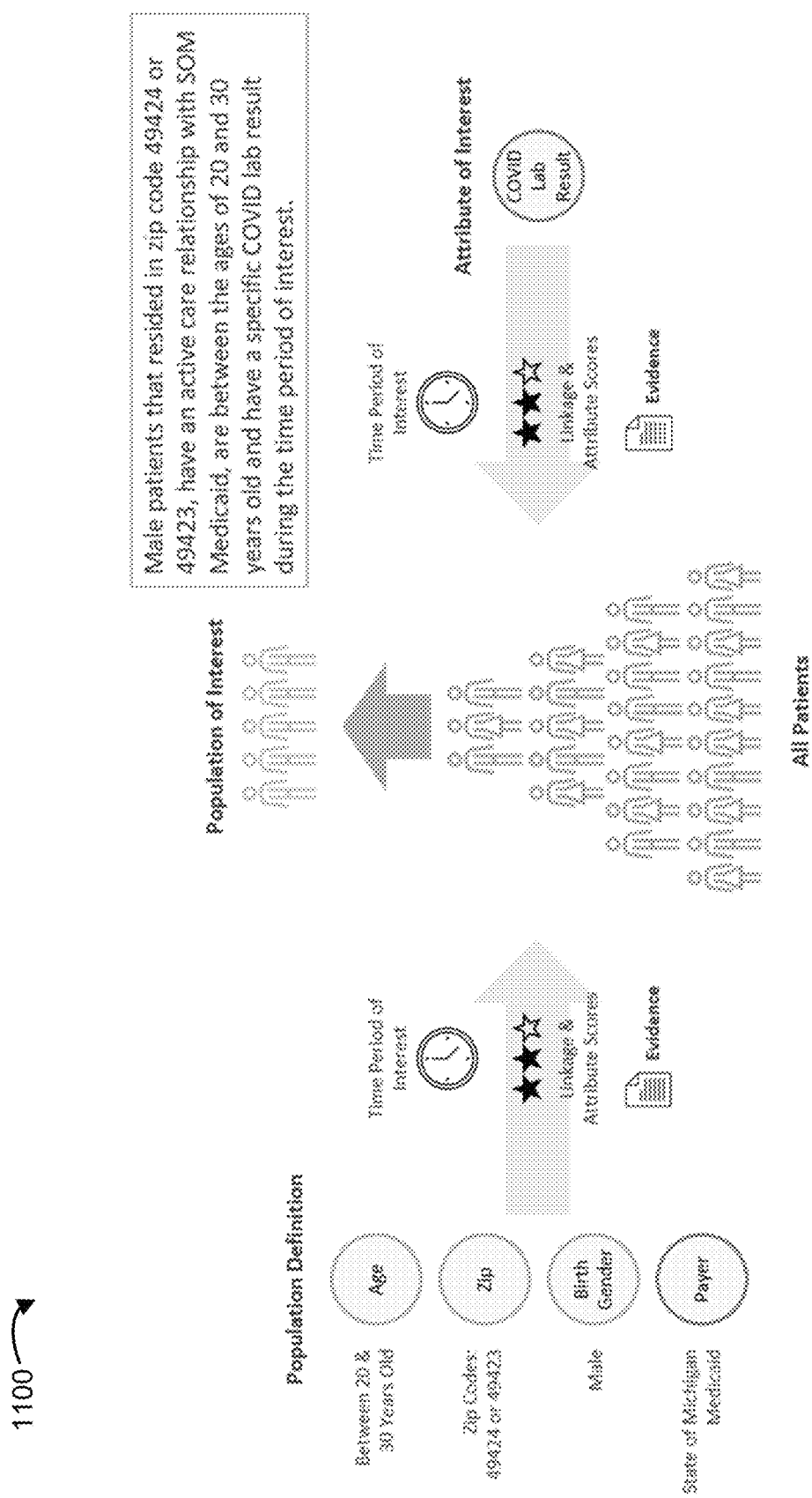
FIG. 11A is an illustration of an example query for population data, in accordance with some embodiments.

FIG. 11A is an illustration of an example query 1100 for population data, in accordance with some embodiments. A data processing system (e.g., a client device 308, 310, or 312 or a node graph generator 314, shown and described with reference to FIG. 3, a server system, etc.) may receive a request for population data indicating a list of people that has a defined set of demographic attributes (e.g., aged between 20 and 30, lives in 49424 or 49423, has a male birth gender, and is a payer of Michigan Medicaid) and that has a defined attribute of interest (e.g., a specific COVID lab result). The request may include separate weights and/or time periods between the attribute of interest and the demographic attributes. The data processing system may identify the patient nodes that meet the criteria for the demographic attributes and the attribute of interest and identify the names of the patients that correspond to the patient nodes as the population for the request. The data processing system may transmit a record including a list including the names of the patients that meet the requested criteria to the requesting computing device. In some embodiments, the data processing system may maintain and increment a counter for the patients and include the final count in the record. Thus, the data processing system may store and retrieve data in a manner that enables fast data retrieval about a population of interest.

Figure 11B:
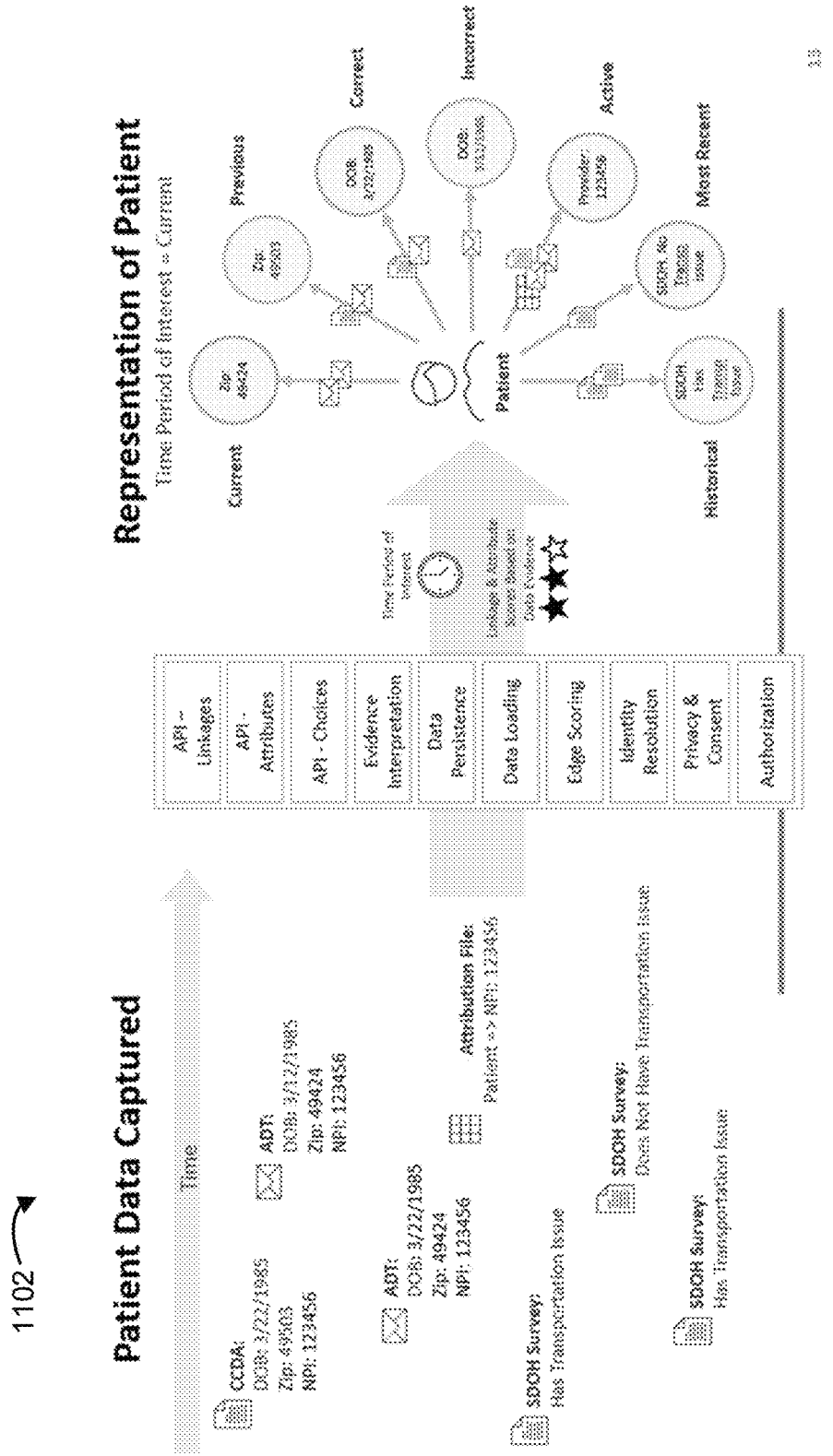
FIG. 11B is an illustration of an example query for individual patient data, in accordance with some embodiments.

FIG. 11B is an illustration of an example query 1102 for individual patient data, in accordance with some embodiments. A data processing system (e.g., a client device 308, 310, or 312 or a node graph generator 314, shown and described with reference to FIG. 3, a server system, etc.) may receive data files from various data sources or clinics about a particular patient. Such data files may include CCDA's, ADT's, attribution files, and/or SDOH surveys. The data processing system may retrieve data from the data files and use the data to update a node graph data structure that contains nodes about individual patients and their attributes. The data processing system may then receive a request identifying the patient, a time period of interest, and a minimum weight. The data processing system may identify a patient node for the patient and then identify attribute nodes that share edges with the patient node that have a weight exceeding the minimum weight and that correspond to time period in the request. The data processing system may retrieve identifications of attributes from such attribute nodes and transmit the identifications to the requesting device. In this way, the data processing system may retrieve requested data while avoiding stale and/or inaccurate data.

Figure 12:
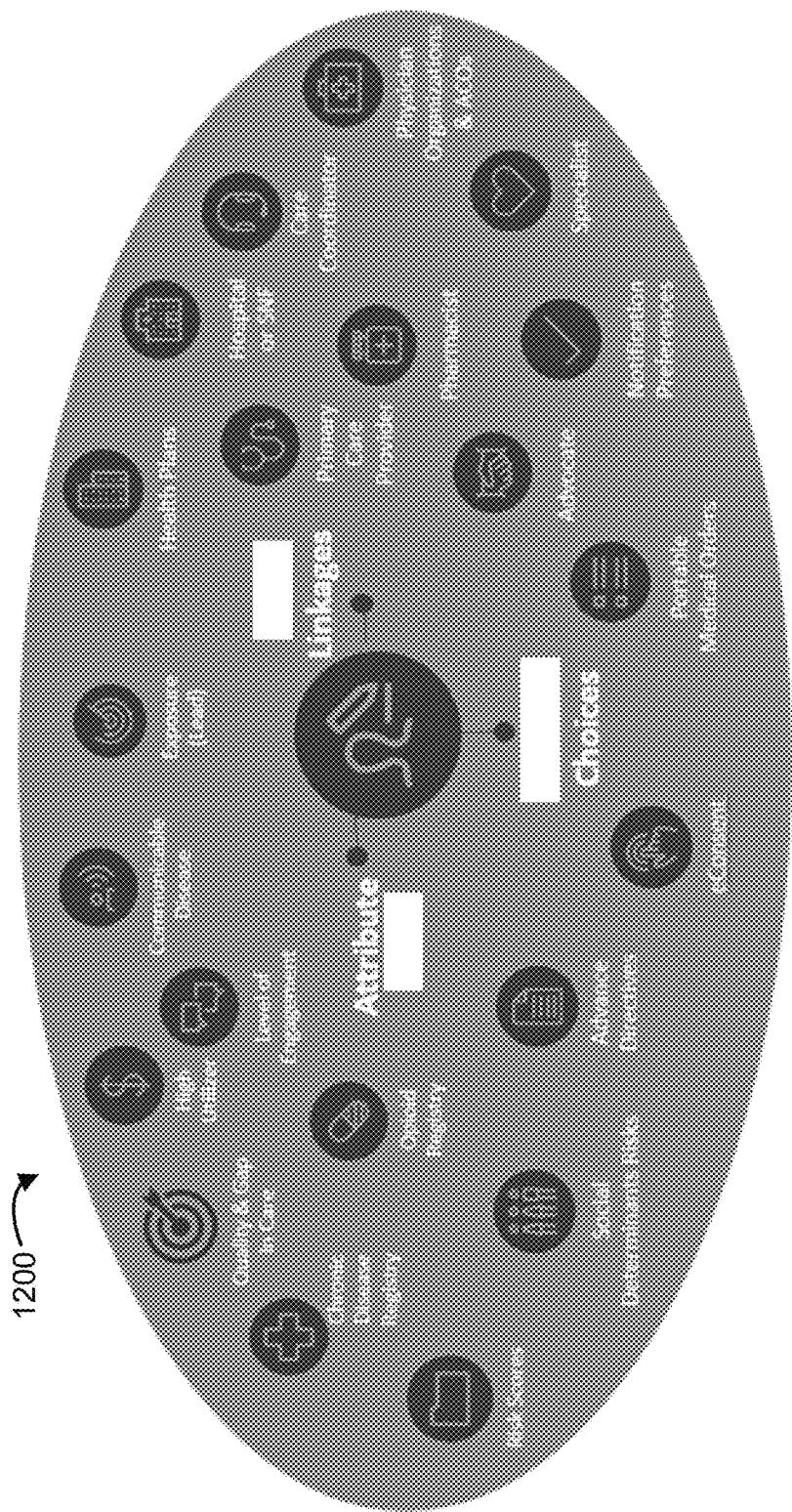
FIG. 12 is an illustration of an example data model of a node graph data structure, in accordance with some embodiments.

FIG. 12 is an illustration of example types of data 1200 in a node graph data structure, in accordance with some embodiments. As illustrated, types of data 1200 may include data indicating attributes of patients, linkages of patients with different clinics, and choices made by the patients. Such data may be individually represented in nodes and/or relationship types in the node graph data structures. Types of data 1200 may include quality and gap in care, high utilizer, level of engagement, opioid registry, chronic disease registry, risk scores, social determinants risks, advance directives, eConsent, portable medical orders, advocate, notification preferences, specialist, pharmacist, physician organizations and ACOS, care coordinator, hospital or SNF, primary care provider, health plans, exposure (lead), communicable disease, etc.

Figure 13:
FIG. 13 is an illustration of examples of types of nodes in a node graph data structure, in accordance with some embodiments.

FIG. 13 is an illustration of examples of types of nodes 1300 in a node graph data structure, in accordance with some embodiments. As illustrated, types of nodes 1300 are organized in a table with groupings in different columns. The different types of nodes may include different types of nodes and sub-type nodes. For instance, the types of nodes may include participant nodes, record/event nodes, quality nodes, location nodes, voice of patient nodes, demographic nodes, clinical nodes, care team nodes, etc.). Participant nodes may include patient nodes, provider nodes, and/or organization nodes. Record/events nodes may include encounter nodes, immunization nodes, COVID Lab nodes, and/or referral nodes. Quality nodes may include gap-in-care nodes, CQI nodes, risk score nodes, and/or value-based contract nodes. Location nodes may include city nodes, zip code nodes, and/or state nodes. Voice of patient nodes may include consent nodes, advanced directive nodes, and/or SDOH surveys. Demographic nodes may include date of birth nodes and/or birth gender nodes. Clinical nodes may include diagnosis nodes. Care team nodes may include delivery preference nodes. Each of the types of nodes may include number of sub-type nodes.

Figure 14:
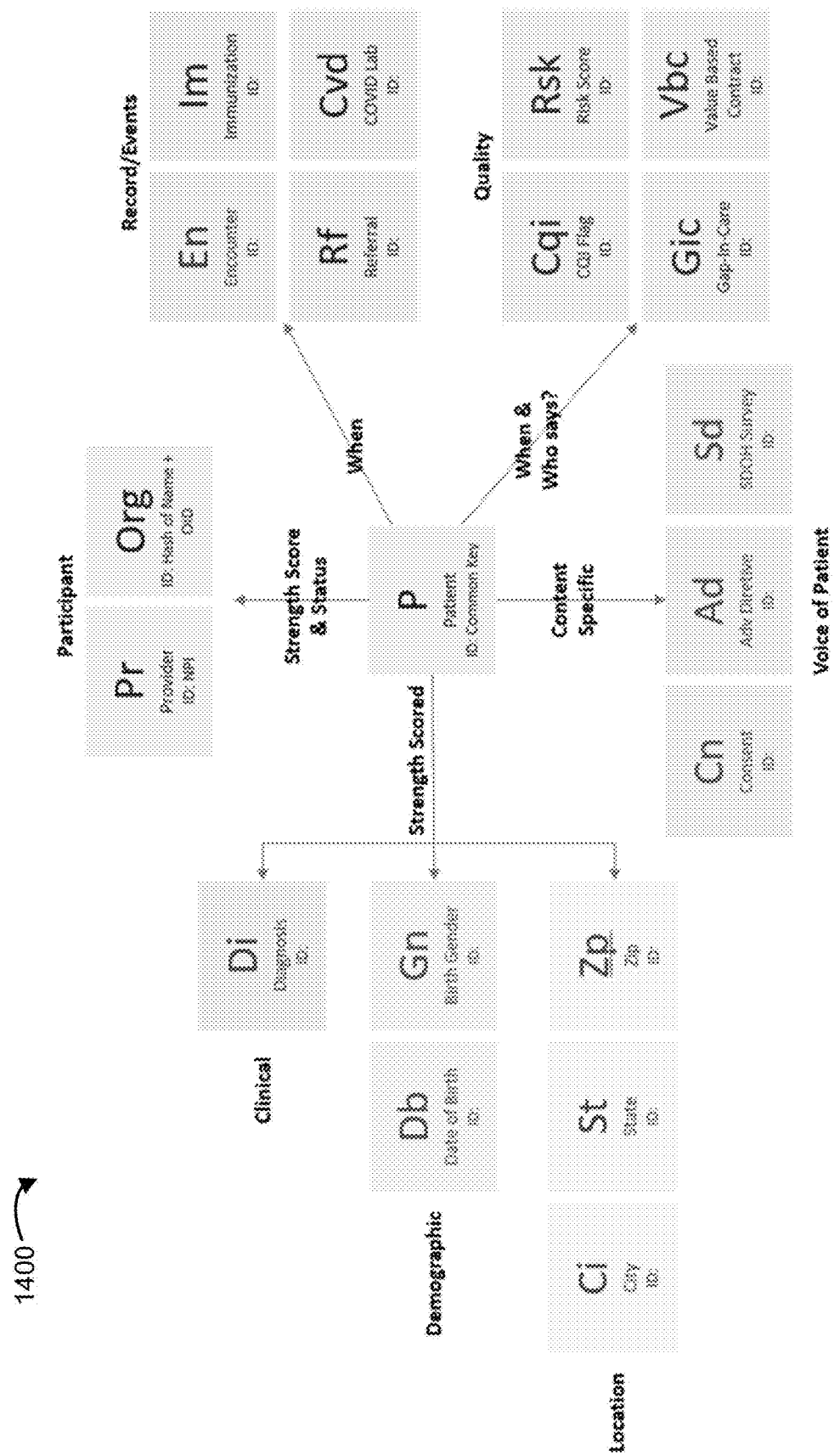
FIG. 14 is an illustration of an example node graph data structure, in accordance with some embodiments.
Figure 15A:
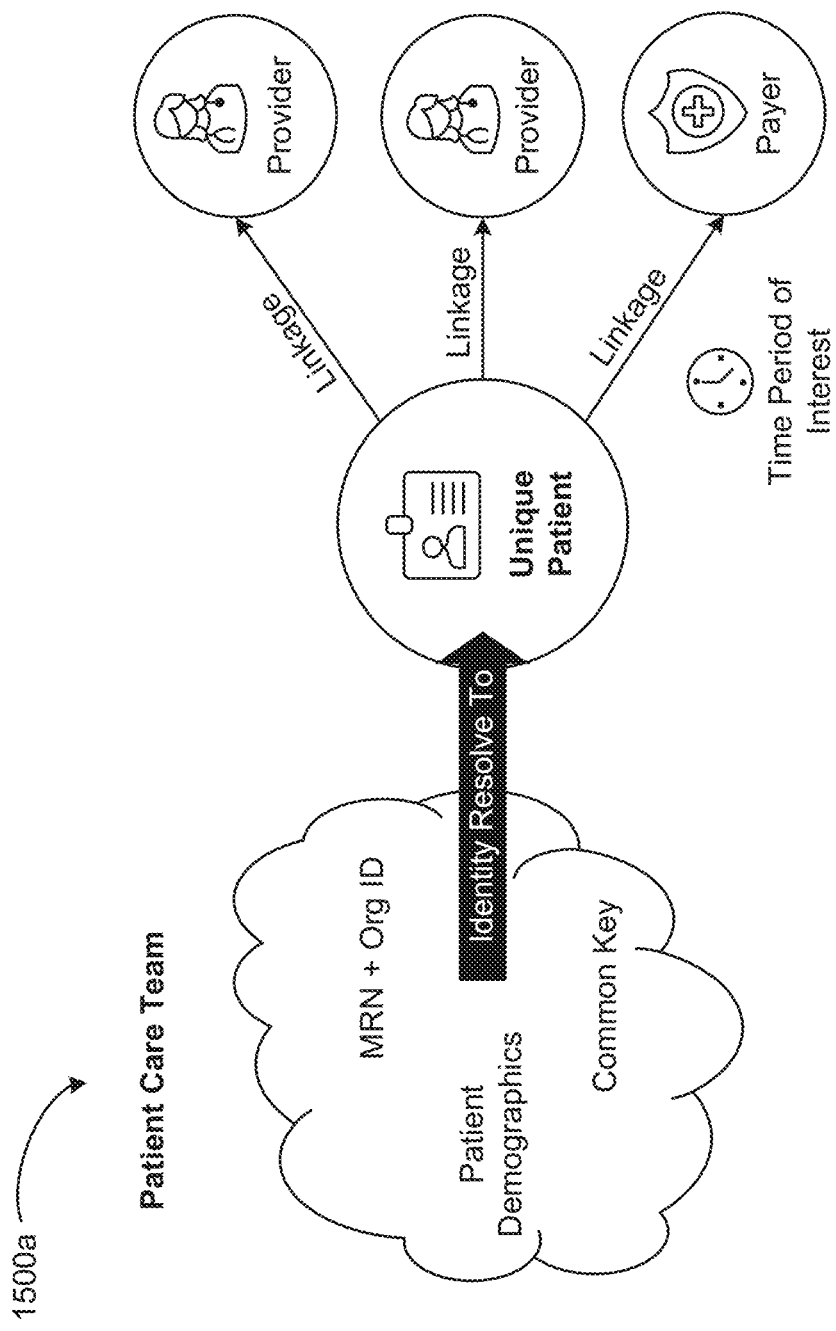
FIGS. 15A-D are illustrations of different example queries for data from node graph data structures, in accordance with some embodiments.
Figure 15B:
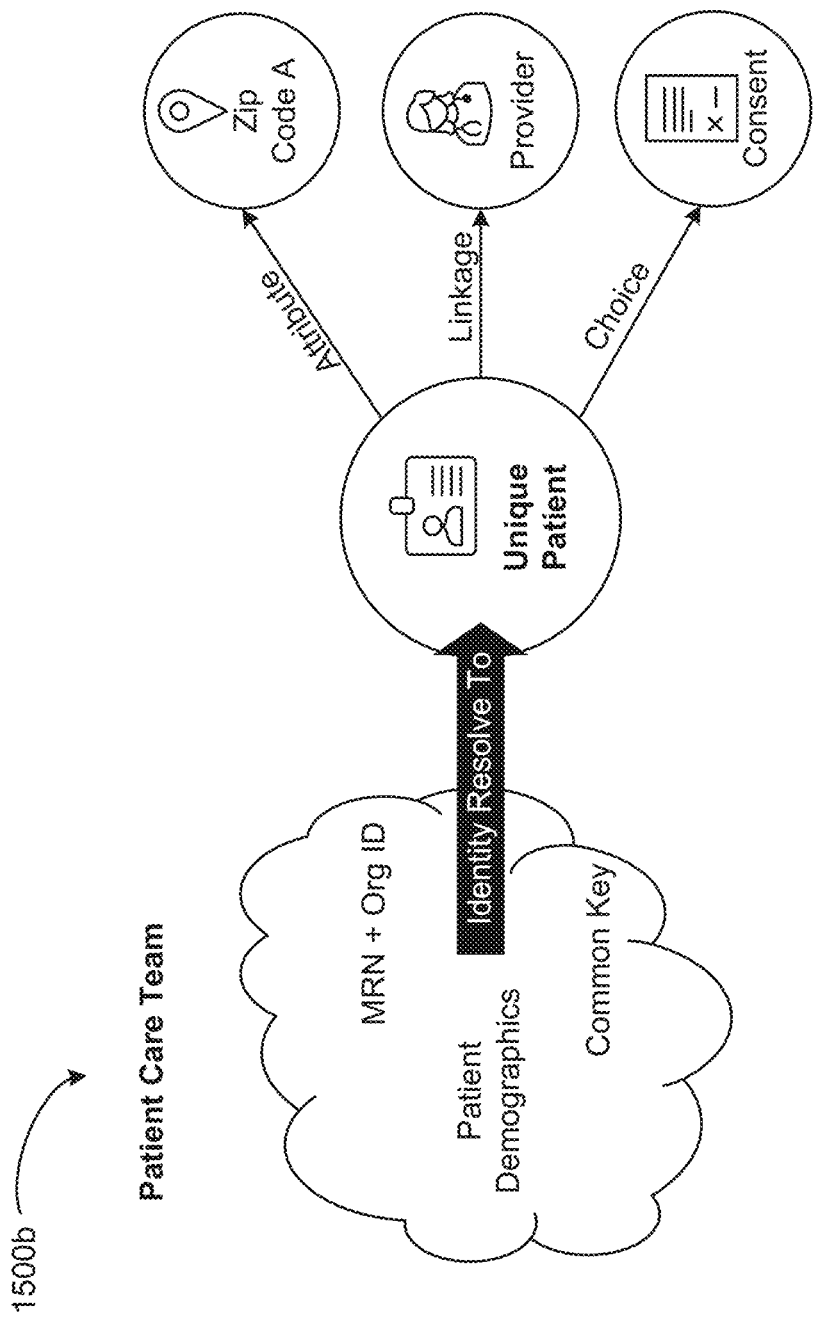
Figure 15C:
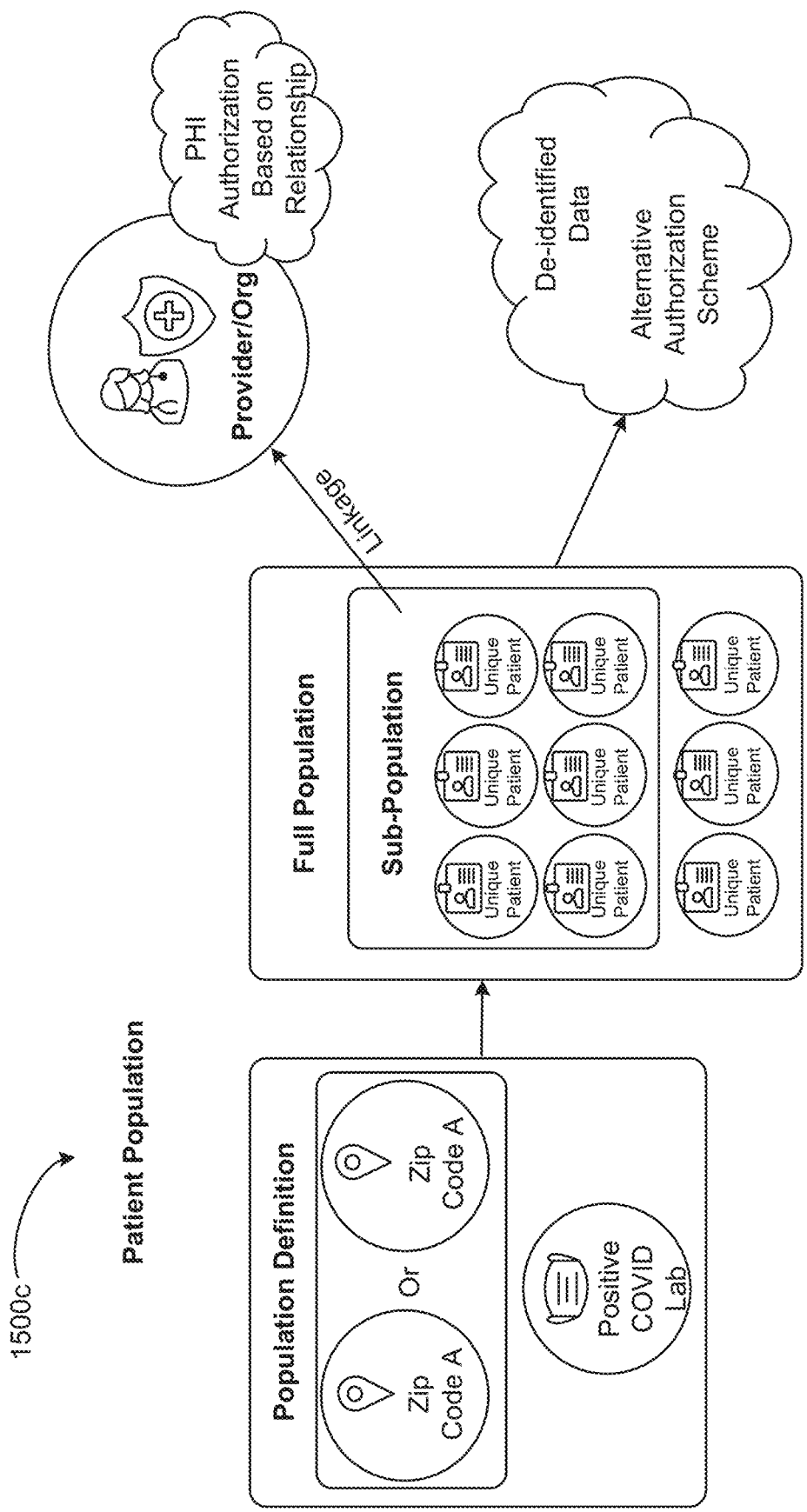
Figure 15D:
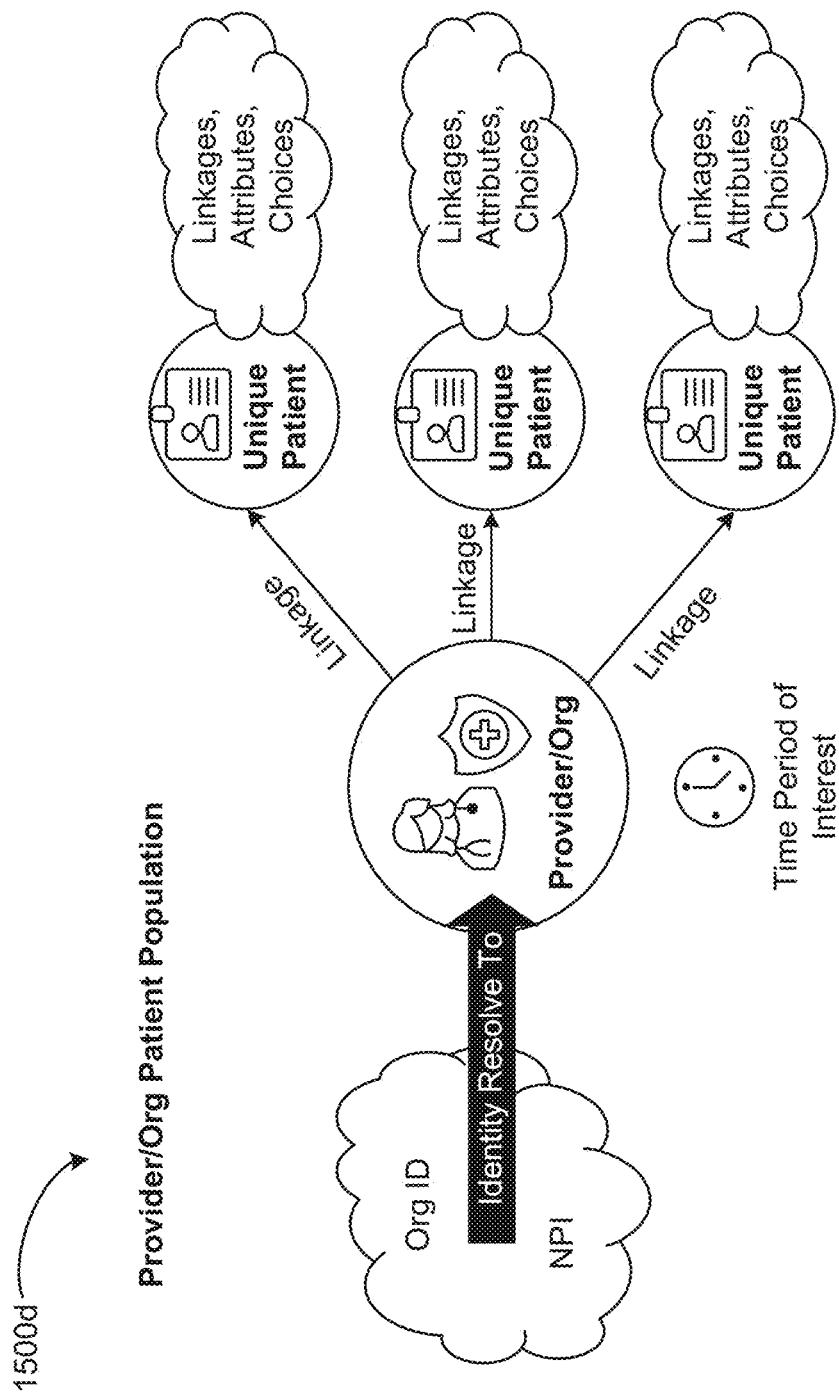

FIG. 14 is an illustration of an example node graph data structure 1400, in accordance with some embodiments. A data processing system (e.g., a client device 308, 310, or 312 or a node graph generator 314, shown and described with reference to FIG. 3, a server system, etc.) may store node graph data structure 1400 as a part of a separate larger node graph data structure that only includes data for a particular patient or patient node of the large node graph data structure. Node graph data structure 1400 may include a patient node linked with different type sub-type nodes as described with respect to FIG. 13. Additionally, node graph data structure 1400 may include descriptions of the types of relationships the patient node has with the different types of nodes. The descriptions may be stored in the data structures that store data for edges between the patient node and the attribute nodes. The data processing system may retrieve the descriptions in response to a request for such description in addition to identifiers of the attributes (e.g., retrieve data identifying the attributes that have edges with the patient node as well as the descriptions that are stored for the edges).

FIGS. 15A-D are illustrations of different types of queries for data from node graph data structures 1500a-d, in accordance with some embodiments. The queries may include requests for a patient care team, a patient context, a patient population, and a clinic patient population. Such requests may additionally include minimum weights and/or time periods of interest. A data processing system (e.g., a client device 308, 310, or 312 or a node graph generator 314, shown and described with reference to FIG. 3, a server system, etc.) may receive such requests and query the node graph data structure for data to include in a response to the request. For example, the data processing system may receive a patient care team request that includes an organization identification, identifications of patient demographics, and a common key for a patient. In response to the request, the data processing system may identify a patient node that has linkages with nodes identifying the data included in the request (and that meets any time period and/or minimum weight criteria in the request). The data processing system may then identify the linkages with different clinic nodes and a payer node to retrieve data indicating the clinics and/or insurance that are a part of the care team providing care to the patient. In another example, the data processing system may receive a request for patient context information. The request may include an organization identification, identifications of patient demographics, and a common key for a patient. In response to the request, the data processing system may identify a patient node that has linkages with nodes identifying the data included in the request (and that meets any time period and/or minimum weight criteria in the request). The data processing system may then identify the linkages the patient node has with other attribute nodes such as a zip code node, a clinic node, and/or a consent node, and retrieve data from the attribute nodes to retrieve context about a particular patient.

In another example, the data processing system may retrieve patient population data. For instance, the data processing system may receive a request that includes a population definition of zip code A or zip code B and positive COVID lab result. In some embodiments, the request may include weight and/or time period criteria. The data processing system may identify the patient nodes in the node graph data structure that are linked to a positive COVID lab result node and either a zip code A node or a zip code B node. The data processing system may then determine if the patient nodes that meet the above criteria (including the weight and/or time period criteria, if applicable) are also linked to a consent node indicating their PHI (e.g., the COVID lab result) may be shared. The data processing system may identify the patient nodes that meet the criteria and that have a link with a consent node and transmit a record identifying the patients of the patient nodes to the requesting client device. In some embodiments, instead of or in addition to including the list identifying the patients in the response, the data processing system may maintain and increment a counter for each patient that meets the criteria, and, in some cases, that is linked to a consent node. The data processing system may transmit the count of the counter to the requesting device, thus providing de-identified data to the requested device and maintaining patient privacy.

In another example, the data processing system may retrieve clinic patient population data. For instance, the data processing system may receive a request that includes an identification of a particular clinic. The data processing system may identify the clinic node in the node graph data structure that includes a matching identifier to the identification of the particular clinic. The data processing system may then identify the patient nodes that are linked to the clinic node and, in some cases, satisfy a time period and/or weight criteria included in the request. The data processing system may generate a record that includes a list of patients that correspond to the identified patient nodes. In some cases, the data processing system may identify attribute nodes that have edges with the patients based on the request including identifications of attributes of the attribute nodes. The data processing system may include identifications of the attributes in the record. The data processing system may then transmit the record to the requesting client device.

Figure 16:
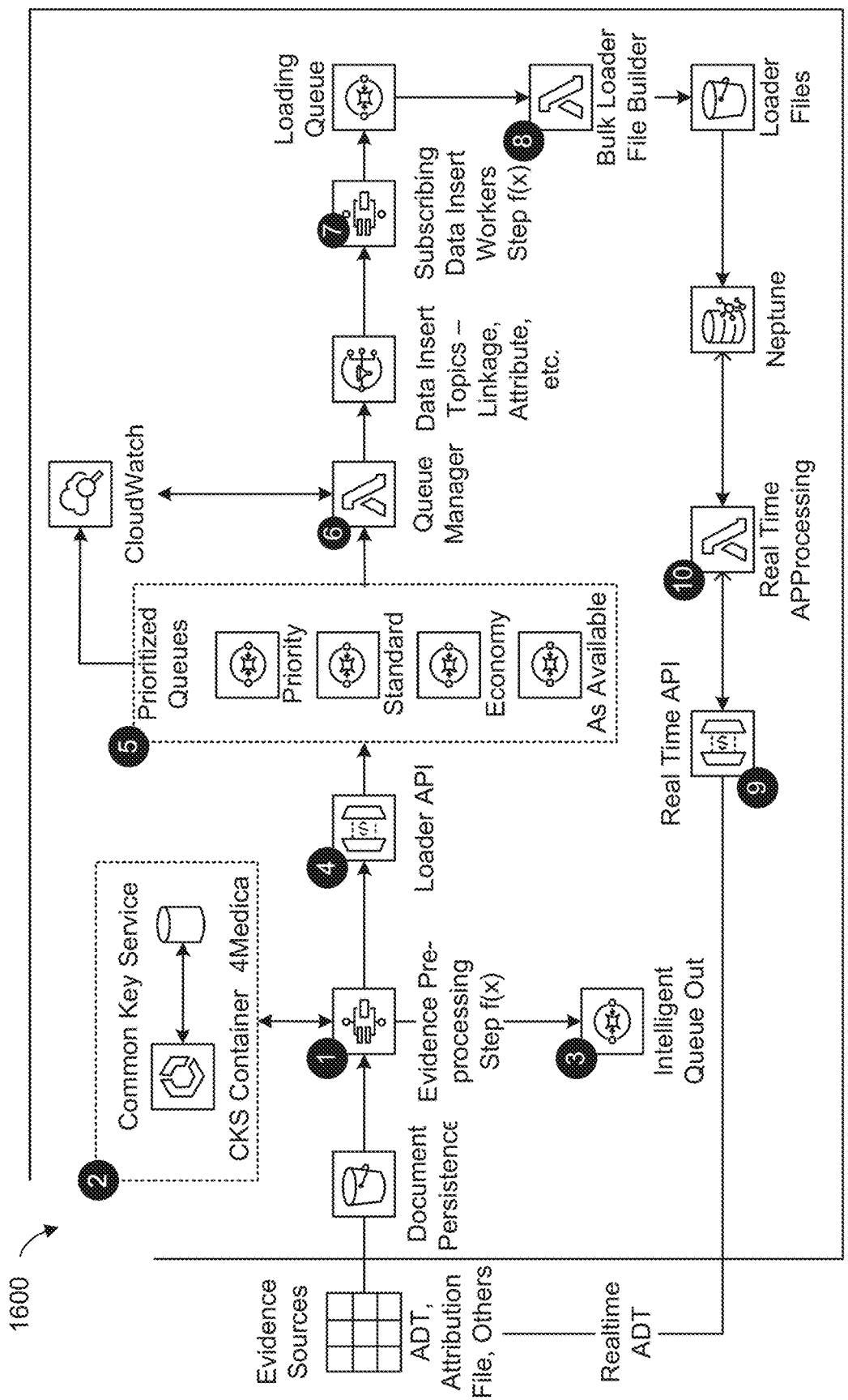
FIG. 16 is an illustration of an example sequence for using priority queues to update a data structure, in accordance with some embodiments.

FIG. 16 is an illustration of an example sequence 1600 for using priority queues to update a data structure, in accordance with some embodiments. In sequence 1600, a data processing system (e.g., a client device 308, 310, or 312 or a node graph generator 314, shown and described with reference to FIG. 3, a server system, etc.) may receive documents from a clinic as data files. Upon receipt of the data files, at operation 1, the data processing system may perform evidence pre-processing of the data files. The pre-processing may include extracting data from the data files using natural language processing and/or object recognition techniques and labeling the extracted data with identifications of the data files from which the data was extracted. In some embodiments, at operation 2, the data processing system may use a common key service (e.g., a set of executable instructions) to identify the identity of the patients that are identified in documents based on common keys that are unique to the patients and that are included as text in the data files. The data processing system may identify the identity of patients that are associated with the documents using the common key service and/or based on the name that is included in the documents and store the patient identities with the patient data that corresponds to the same data files. At operation 3, the data processing system may determine and assign identifications of queues to the extracted data and/or data files. The data processing system may determine the queues for the different pieces of data based on the data source, file type, and/or data type of the respective pieces of data, as described herein.

Figure 17:
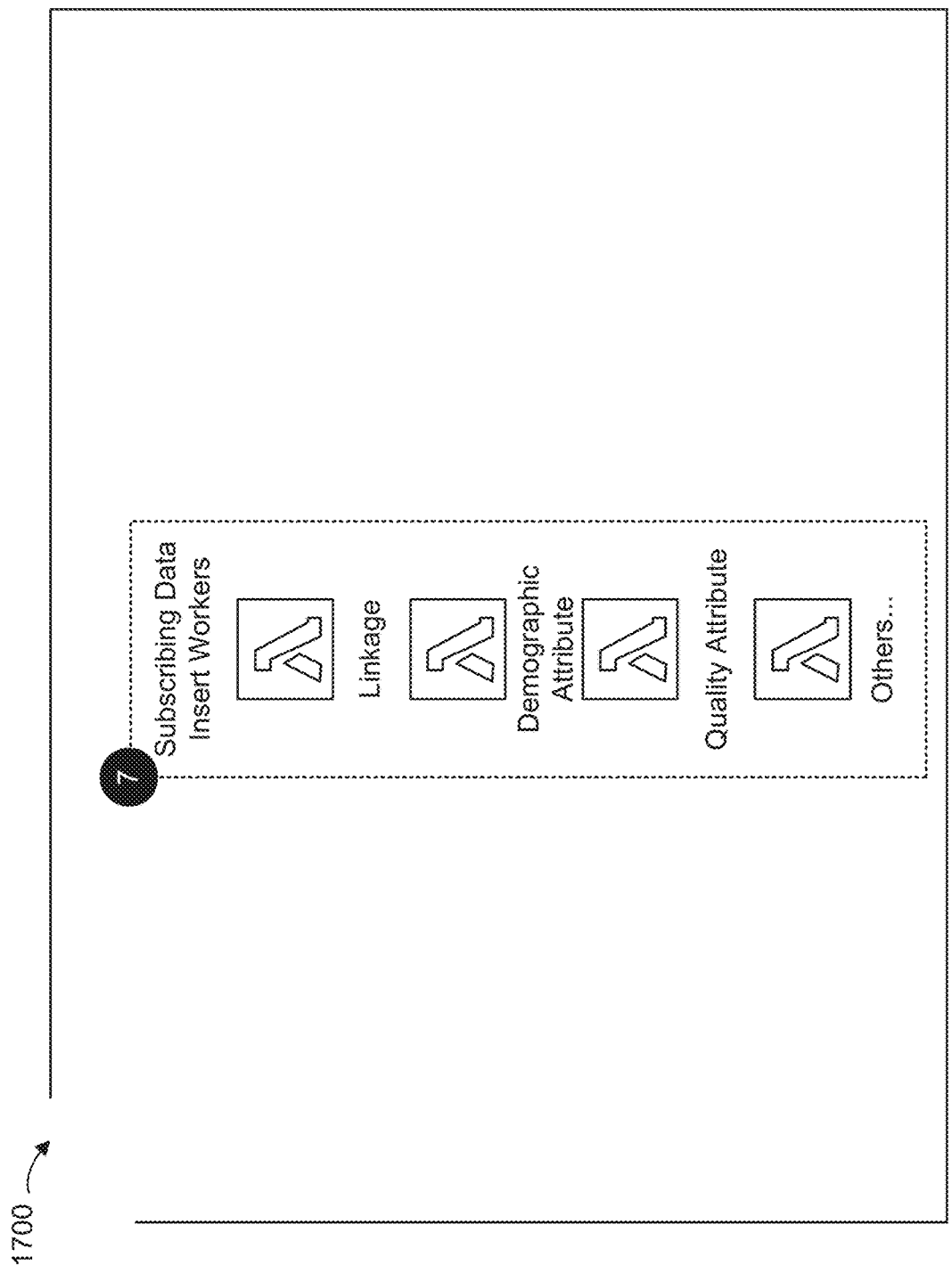
FIG. 17 is an illustration of different subscriptions that can be made when using priority queues to update a data structure, in accordance with some embodiments.

At operation 4, the data processing system may execute a loader API (e.g., a set of executable instructions) to insert the pieces of data into prioritized queues 5. The prioritized queues 5 may include queues such as priority, standard, economy, as available, etc. Via the loader API, the data processing system may retrieve the pieces of data that have been assigned to different queues and insert the pieces of data into the queues according to the assignments. At operation 6, the data processing system may execute a queue manager (e.g., a set of executable instructions) to retrieve data from the prioritized queues 5 according to a defined pattern (e.g., retrieve all of the data from the priority queue, then retrieve all of the data from the standard queues, then retrieve all of the data in the economy queue, etc.). At operation 7, the data processing system may subscribe to the data insert workers (e.g., retrieve data from memory identifying different possible linkages, demographic attributes, quality attributes, etc.). An example of the different subscriptions the data processing system may make at operation 7 is shown in example view of subscription insert workers 1700 in FIG. 17.

At operation 8, the data processing system may execute a bulker loader file builder (e.g., a set of executable instructions) to generate a bulk file of data the data processing system collected from prioritized queues 5. The data processing system may generate the bulk file by inserting retrieved data from the prioritized queues 5 into the bulk file as the data processing system retrieves further data from the prioritized queues 5. Accordingly, the data processing system may insert data into the bulk file in the order of priority of the data and/or according to the pattern in which the data processing system retrieved the data. The data processing system may use batch processing techniques to retrieve data from the bulk file upon the bulk file reaching a capacity threshold or upon an internal clock of the data processing system indicating to process data in the bulk file. The data processing system may then update a data structure, such as a node graph data structure with the retrieved data and/or store the data files themselves in a separate database to preserve the data in a retrievable manner. At operations 9 and 10, the data processing system may execute a real-time API (e.g., a set of executable instructions) to continuously retrieve or receive data from data sources to continue sequence 1600. In this way, the data processing system may store patient data in the data structure using a priority system to ensure PHI data and data that can be used to create or verify relationships between nodes can be uploaded to the data structure earlier. Accordingly, when clinicians are accessing the data structure to retrieve data, the data may be available earlier than other data that is less important, such as demographic information.

Figure 18:
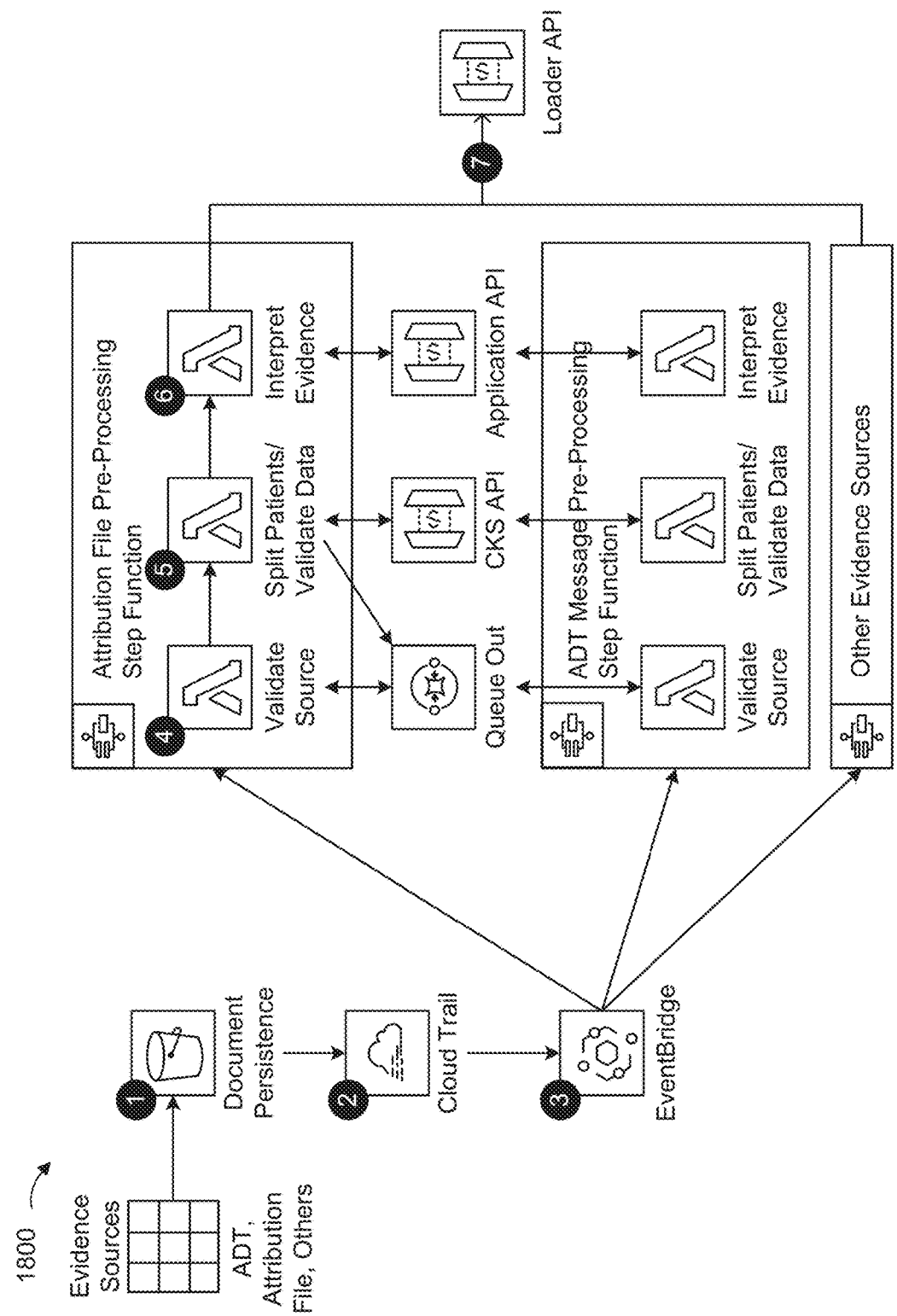
FIG. 18 is an illustration of an example sequence of pre-processing data prior to updating a data structure, in accordance with some embodiments.

FIG. 18 is an illustration of an example sequence 1800 of pre-processing data prior to updating a data structure, in accordance with some embodiments. In sequence 1800, a data processing system (e.g., a client device 308, 310, or 312 or a node graph generator 314, shown and described with reference to FIG. 3, a server system, etc.) may receive documents from a clinic or clinics. The data processing may receive the documents in data files from different sources and then identify the types of the documents. For example, the data processing system may identify the types of the documents using natural language processing techniques and/or object recognition techniques to determine whether the documents are ADT's, CCDA's, SOH surveys, attribution files, etc. If the data processing system determines a document is an ADT message, the data processing system may execute an ADT message pre-processing step function. In doing so, the data processing system may validate the source that sent the document (e.g., validate the certificate or signature that is on or included with the document), validate the data in the document (e.g., validate the format of the data to make sure it matches the formats of other data of the same type), and interpret the evidence (e.g., determine the types of data in the document). If the data processing system determines a document is an attribution file, the data procession may execute an attribution file pre-processing step function. In doing so, the data processing system may validate the data source, identify the different patients and the data that pertains to the different patients in the attribution file, and interpret the evidence. The data processing system may perform similar operations for other document types. Upon doing so, the data processing system may upload the documents or the data from the documents to prioritized queues as described herein.

Figure 19:
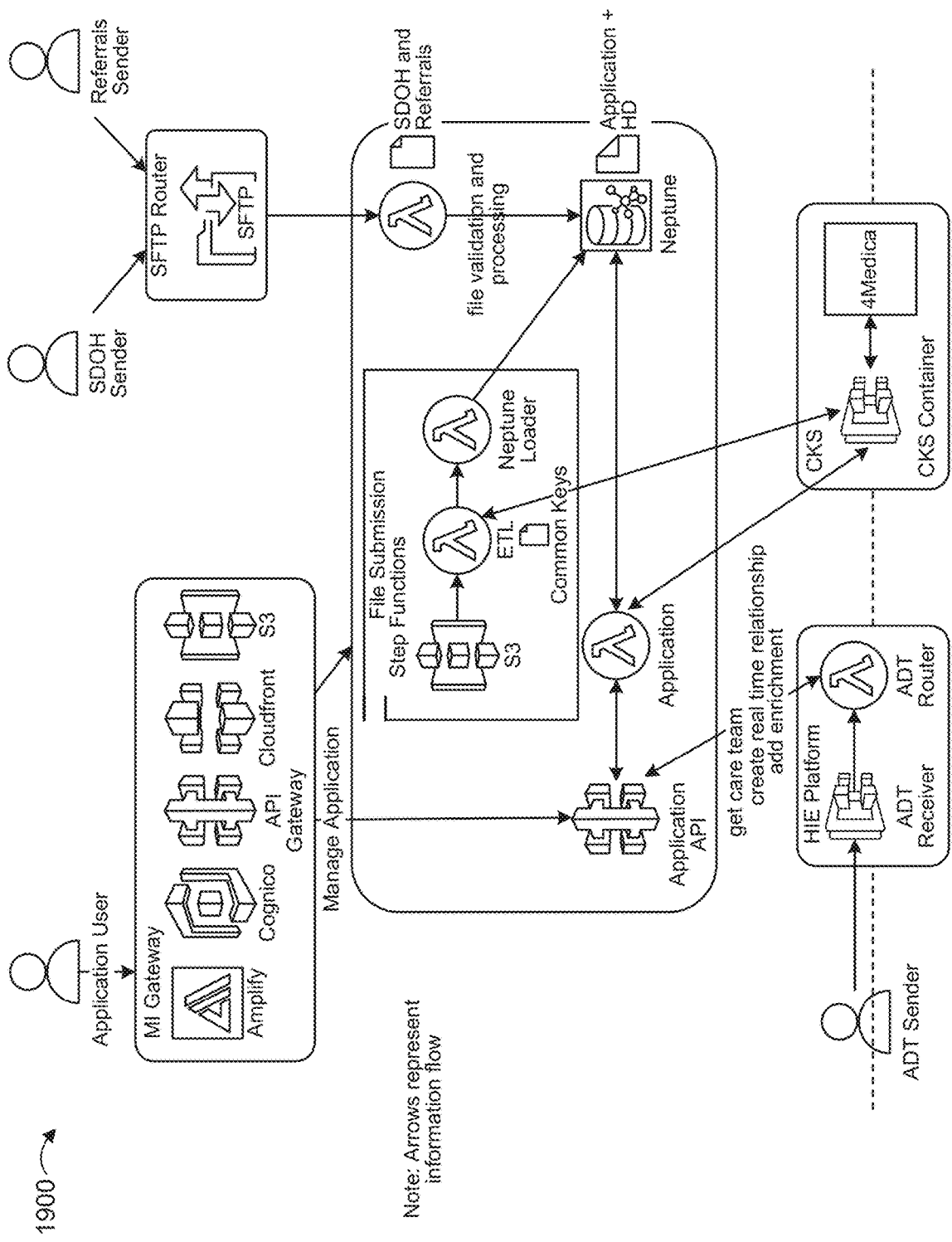
FIG. 19 is an illustration of an example environment for uploading data to a node graph generation system, in accordance with some embodiments.

FIG. 19 is an illustration of different examples of an environment 1900 for uploading data to a node graph generation system, in accordance with some embodiments. Environment 1900 may include the same or similar components to node graph generation system 300, shown and described with reference to FIG. 3. In environment 1900, an application administrator may access a computing device hosting an application configured to store a node graph data structure with patient data. The application administrator can configure how the application operates and stores various types of data in the node graph data structure. Additionally, environment 1900 may include an ADT sender that accesses a computer that receives the ADT and routes the ADT to an application API hosted by the computer hosting the application. The computer may receive the ADT and use data from the ADT to update the node graph data structure according to the systems and methods described herein. Similarly, environment 1900 may include SDOH senders and referral senders accessing computers that transmit the SDOH and referral data files to the computer hosting the application via an SFTP router. The computer hosting the application may receive the SDOH and referral data files, extract data from the data files, and upload the extracted data to the node graph data structure. In some cases, the data processing system may perform identity resolution on the data files that the computer receives and transmit a key (e.g., a common key) to an external device, which may store a database with relationships between such keys and identities of individuals. The external device may compare the key to the database as an index, identify the identity of the individuals identified in the document, and transmit the identity back to the computer to use to update the node graph data structure (e.g., to identify the patient node of the individual).

Figure 20:
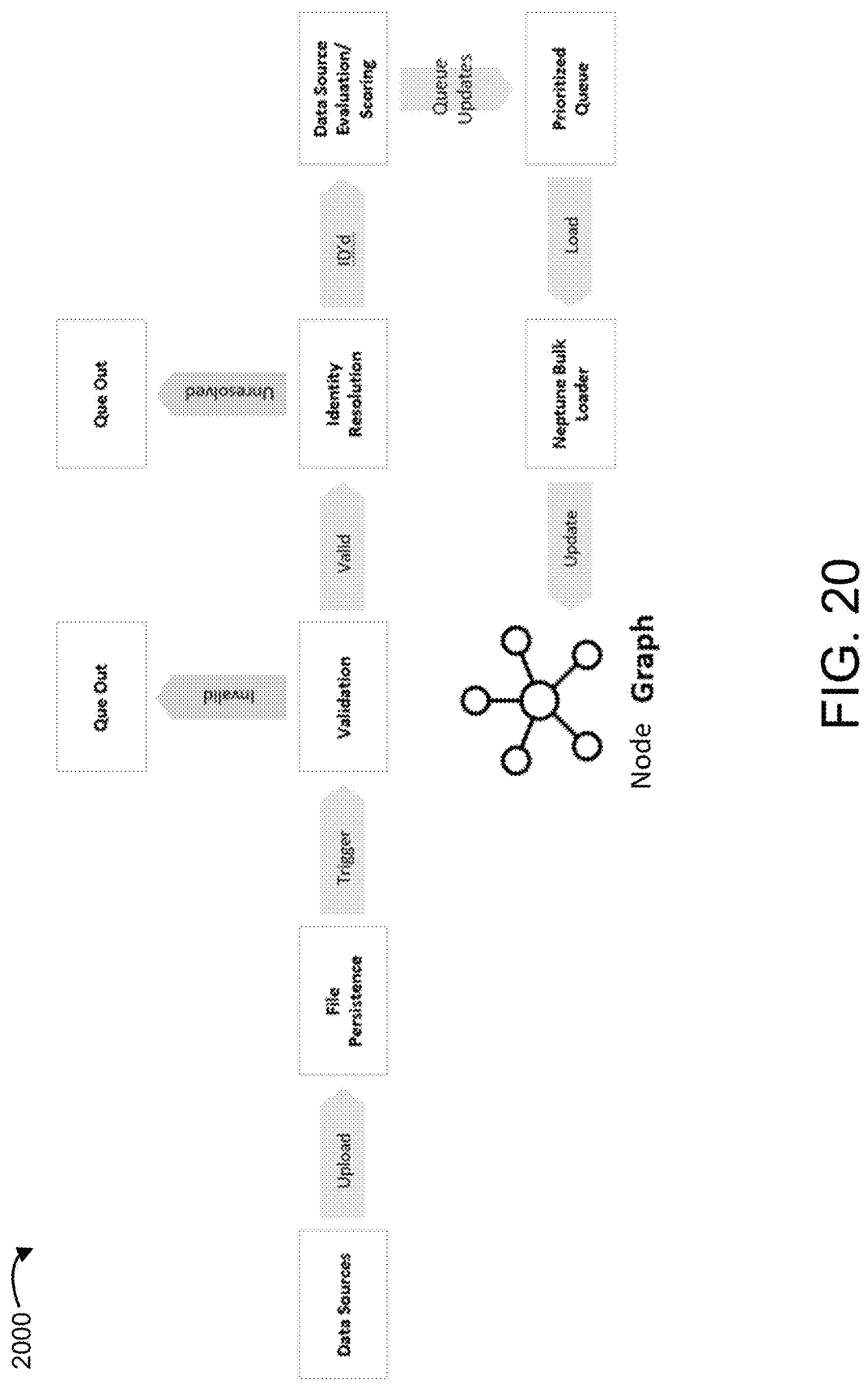
FIG. 20 is an illustration of an example sequence for uploading data to a node graph data structure, in accordance with some embodiments.

FIG. 20 is an illustration of an example sequence 2000 for uploading data to a node graph data structure, in accordance with some embodiments. In sequence 2000, via client devices at various data sources (e.g., clinics), the data sources may upload data files containing documents that include information about various patients that visit or visited the respective clinics for care. The client devices may upload the data files to a data processing system (e.g., a client device 308, 310, or 312 or a node graph generator 314, shown and described with reference to FIG. 3, a server system, etc.) that may store the data files in a local database. Upon receiving the data files, the data processing system may validate the data files such as by authenticating signatures on the documents in the data files against stored signatures to determine if the signatures match or match within a threshold. If the data processing system cannot validate a particular document or data file, the data processing system may discard (e.g., remove from memory) the data file.

If the data processing system can validate the data file or document in the data file, the data processing system can perform identity resolution techniques on the documents to determine the identities of the patients associated with the documents (e.g., determine the identity of patients associated with the documents according to a common key system). If the data processing system cannot identify a patient for a particular document, the data processing system may discard the document. Otherwise, for each document for which the data processing system identified a patient, the data processing system can identify the data sources and/or trust scores for the data sources that provided the documents. The data processing system can store the data in prioritized queues, as described herein. The data processing system may then retrieve the data from the queues according to their priority and load the retrieved data to update a node graph data structure with the retrieved data.

Figure 21:
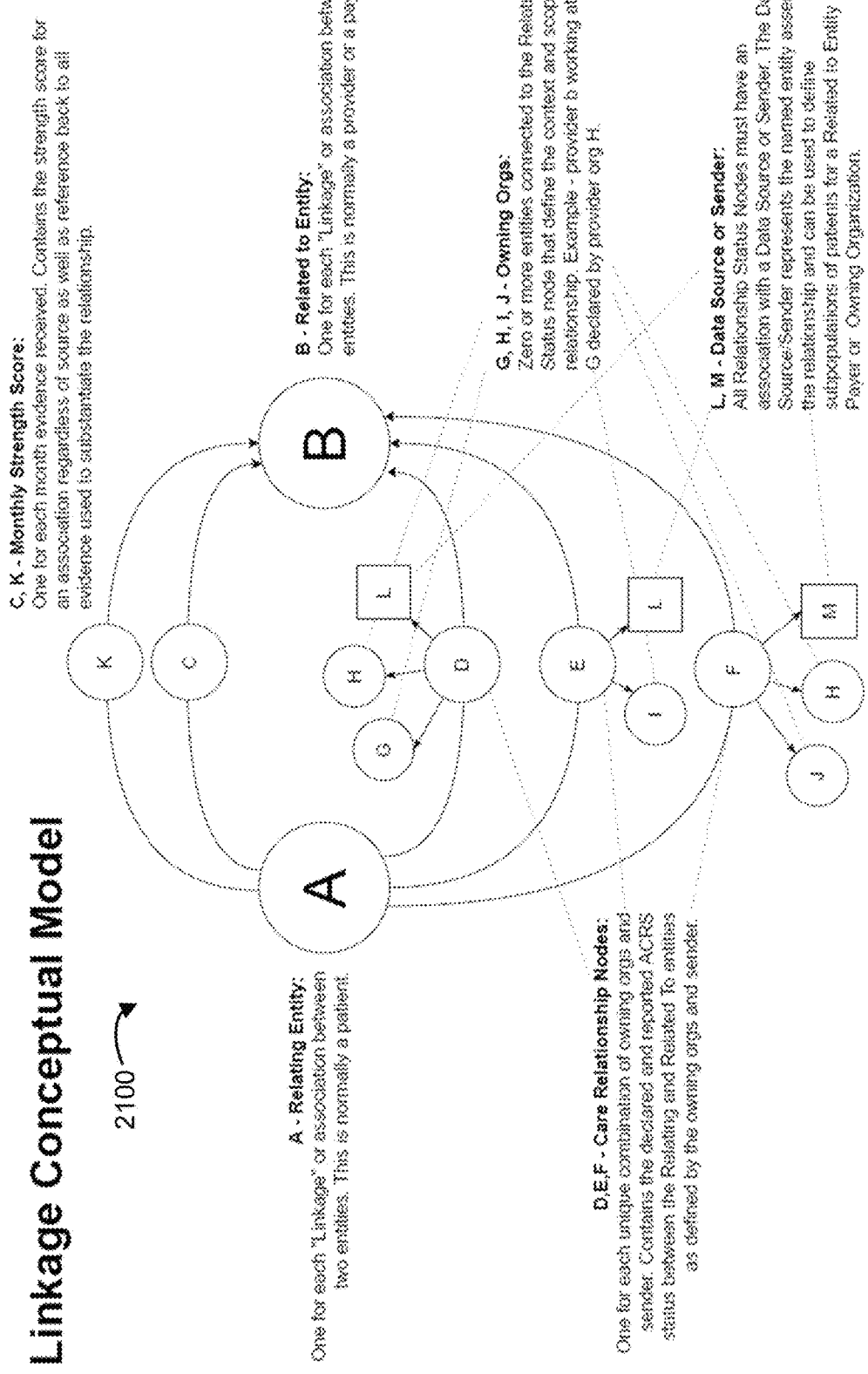
FIG. 21 is an illustration of example linkages in a node graph data structure, in accordance with some embodiments.
Figure 22:
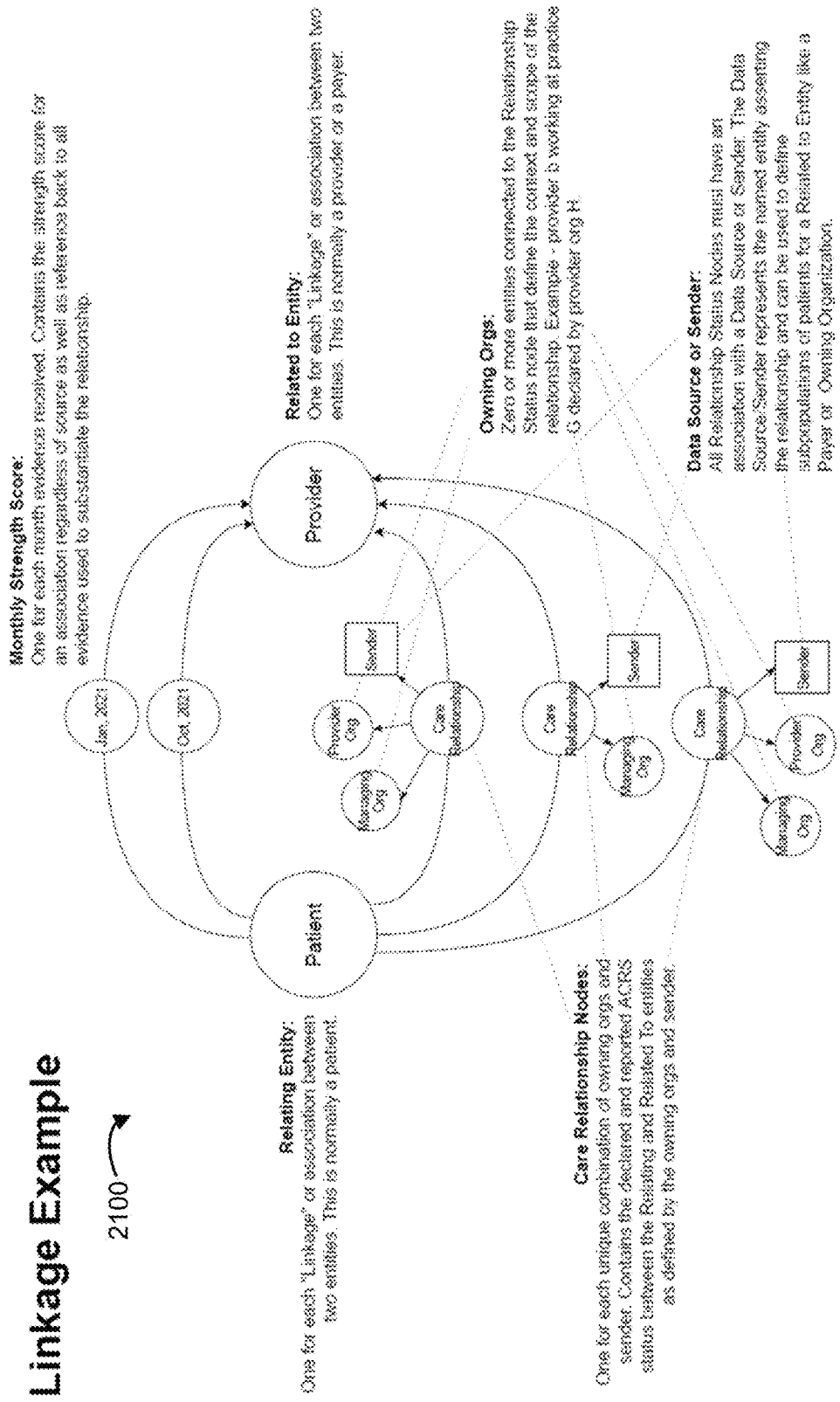
FIG. 22 is another illustration of example linkages in a node graph data structure, in accordance with some embodiments.

FIGS. 21 and 22 are illustrations of example linkages in a node graph data structure 2100, in accordance with some embodiments. Node graph data structure 2100 may include one or more relating entity nodes. Node graph data structure 2100 may include a least one relating entity nodes for each linkage or association between two entities. A relating entity node may be a patient node. Node graph data structure 2100 may also include at least one related to entity node for each linkage or associations between two entities. A related to entity node may be a clinic node, a provider node, a payer node, etc. Node graph data structure 2100 may additionally include strength scores (e.g., weights) for edges between relating entity nodes. Node graph data structure 2100 may contain strength scores between two relating entity nodes for multiple time periods for which evidence was received regardless of the source as well as references (e.g., pointers to the locations) to the evidence that was used to determine the strength scores to substantiate the relationship between the two nodes.

Node graph data structure 2100 may also include care relationship nodes (e.g., relationship status nodes). Node graph data structure 2100 may include one care relationship node for each unique combination of owning organizations and senders. Care relationship nodes may contain the declared and reported care status between the relating and related entities as defined by the owning organizations and the sender.

Node graph data structure 2100 may include owning organization nodes. Owning organization nodes may represent entities connected to the care relationship node that define the context and score of the relationship. For example, an owning organization node may indicate provider b is working at practice g declared by provider organization H.

Node graph data structure may include data source and/or sender nodes. The data source or sender nodes may represent the named entities asserting the relationships and can be used to subpopulations of patients for a related to entity, such as a payer or owning organization. In some embodiments, all care relationship nodes must have an association with a data source or sender node.

Figure 23:
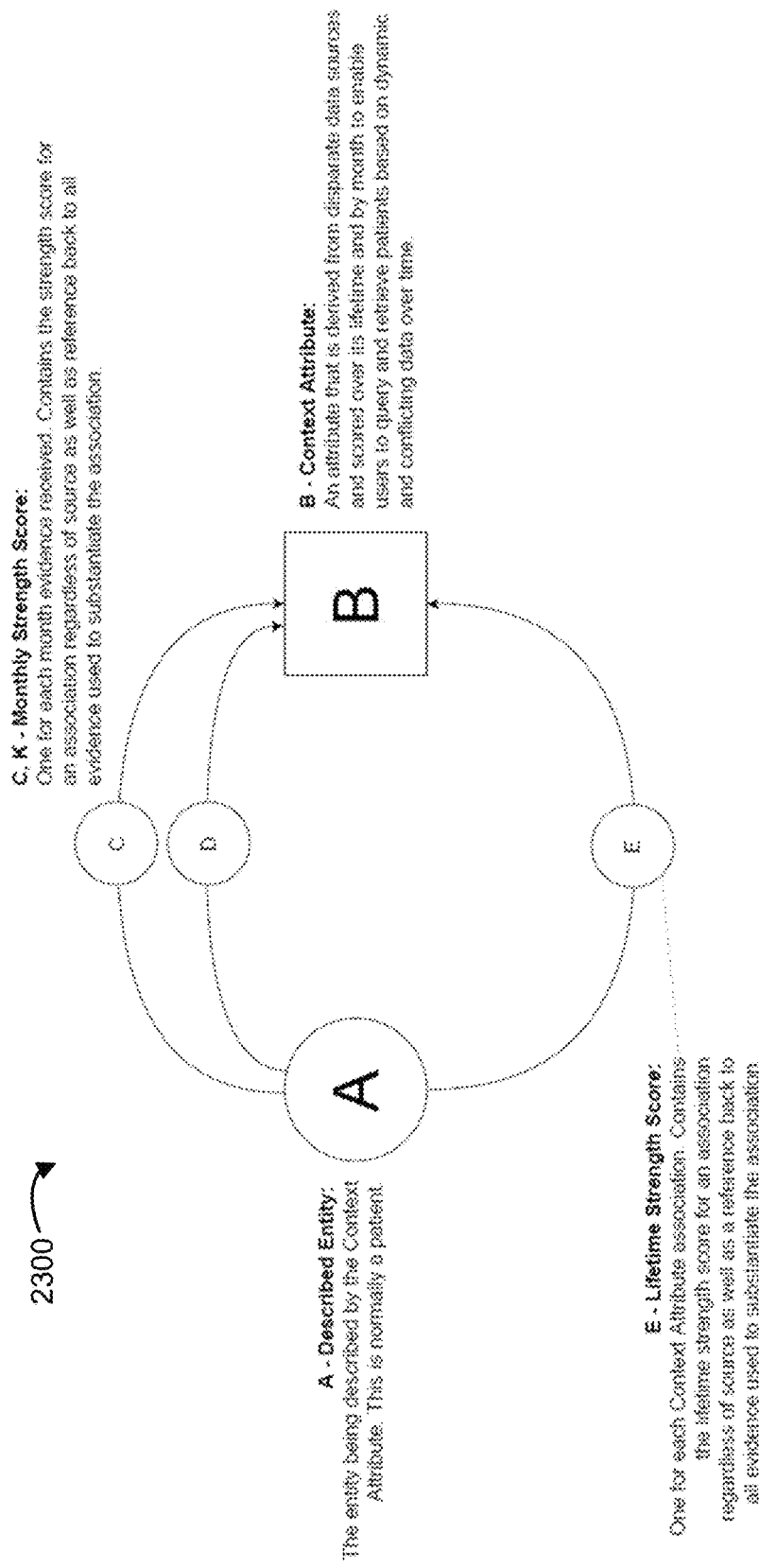
FIG. 23 is an illustration of example linkages between a patient node and an attribute node, in accordance with some embodiments.
Figure 24:
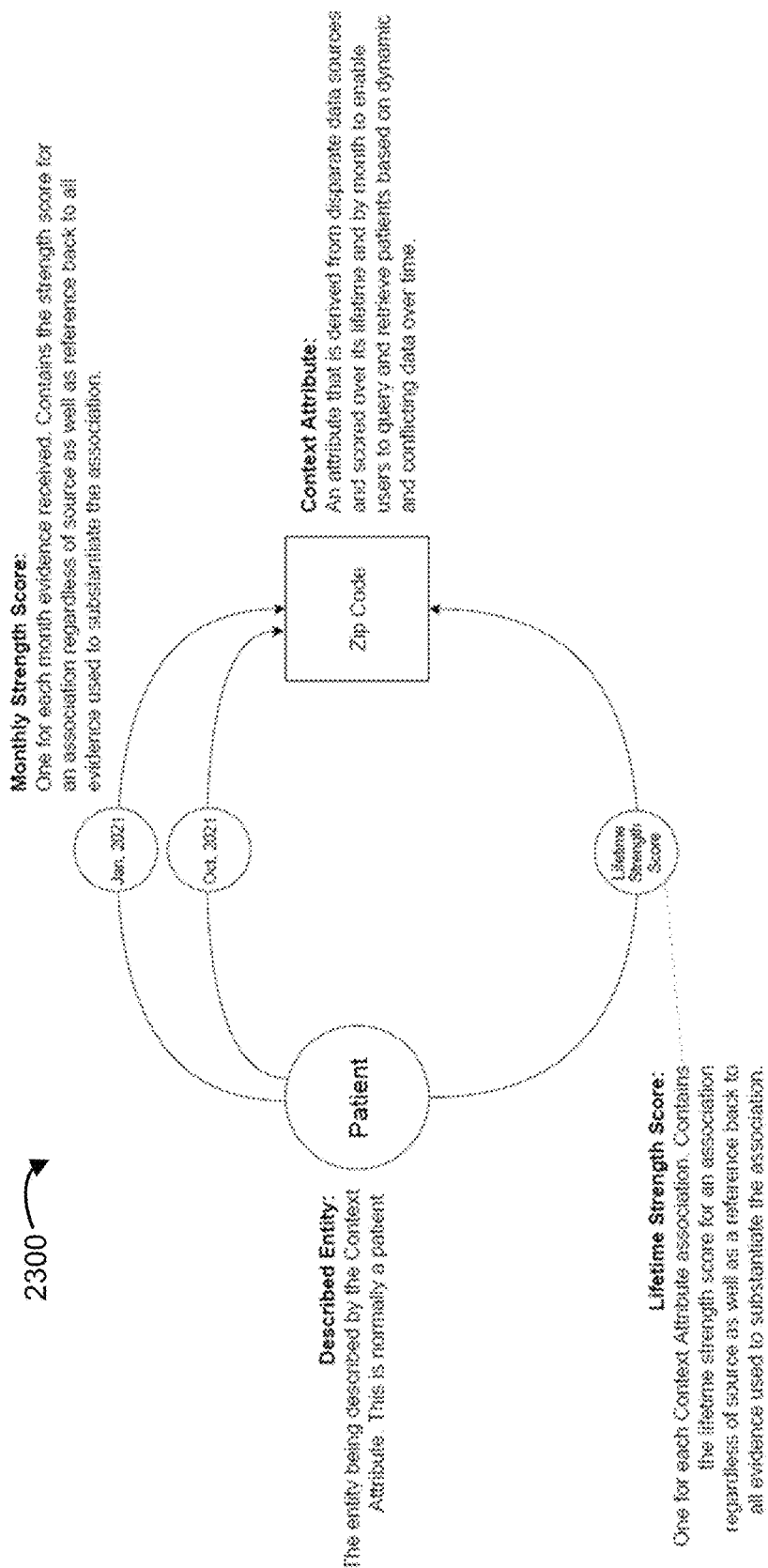
FIG. 24 is another illustration of example linkages between a patient node and an attribute node, in accordance with some embodiments.

FIGS. 23 and 24 are illustrations of example linkages between a patient node and an attribute node of a node graph data structure 2300, in accordance with some embodiments. As illustrated, node graph data structure 2300 may include a described entity node linked to a context attribute node. The described entity node may be associated with an entity (e.g., a patient) that is being described by an attribute (e.g., a zip code) that is associated with the context attribute node. The attribute associated with the context attribute node may be an attribute derived from disparate data sources and scored over its lifetime and by a time period (e.g., a month) to enable users to query and retrieve patient data based on dynamic and conflicting data over time. The described entity node may be linked to the context attribute node by three edges, two edges that are associated with and contain strength scores for separate time periods and a third edge that contains a lifetime strength for the association between the described entity node and the context attribute node.

Figure 25:
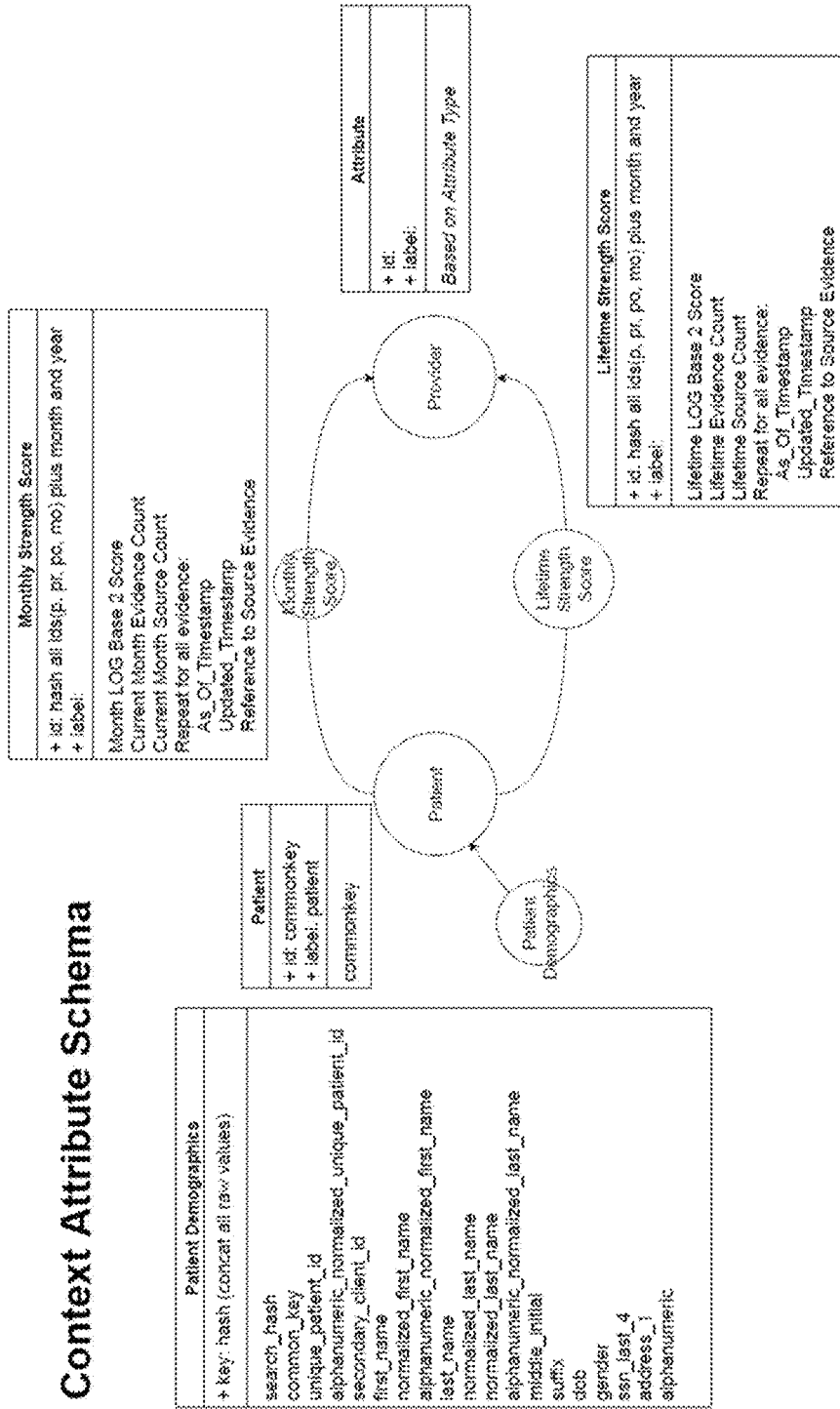
FIG. 25 is an illustration of an example context attribute schema, in accordance with some embodiments.

FIG. 25 is an illustration of an example context attribute schema of a node graph data structure 2600, in accordance with some embodiments. The context attribute schema illustrates the data structures of each of the nodes in node graph data structure 2500 as well as the data that is included in the data structures. Node graph data structure 2500 may include a patient node that is linked to nodes for patient demographics. In some embodiments, the patient node may be linked to a single attribute node that contains a set of patient demographics. In such embodiments, the attribute node may include a key that is a hash of a concatenation of all of the raw values of patient demographics. When retrieving demographic data about a patient, the data processing system may query node graph data structure 2500 using the key to quickly identify the patient demographics node. The data processing system may identify the patient node using a common key. The patient node may additionally store the label "patient" that indicates the patient node is associated with a patient.

The patient node may be linked to the attribute node through at least one time period edge. The attribute node may include an identification of the attribute and/or a label indicating the type of the attribute. The time period edge may include a data structure that stores data for the time period such as the weight for the time period, a current time period evidence count, a current time period source count, and, for all of the evidence (e.g., documents that provide evidence of the link between the patient node and attribute node): as of timestamps, updated timestamps, and pointers to a database to access the evidence. The time period edge may be identified based on a hash of the data stored in the data structure and/or the time period, such as the month and year. The data processing system may identify the data structure of the time period edge using the hash and retrieve data from the data structure to respond to a request.

The patient node may additionally or instead be linked to the attribute node through a lifetime edge. The lifetime edge may include a data structure that stores for the lifetime of the relationship between the patient node and the attribute node. The data structure may store data the data processing system received as evidence for the relationship between the patient node and the attribute node. In doing so, the data processing system may store the same data as all of the time period edges between the patient node and the attribute node. The lifetime edge may be identified based on a hash of the data stored in the data structure and/or the time period of the lifetime, such as the month and year. The data processing system may identify the data structure of the lifetime edge using the hash and retrieve data from the data structure to respond to a request.

Figure 26:
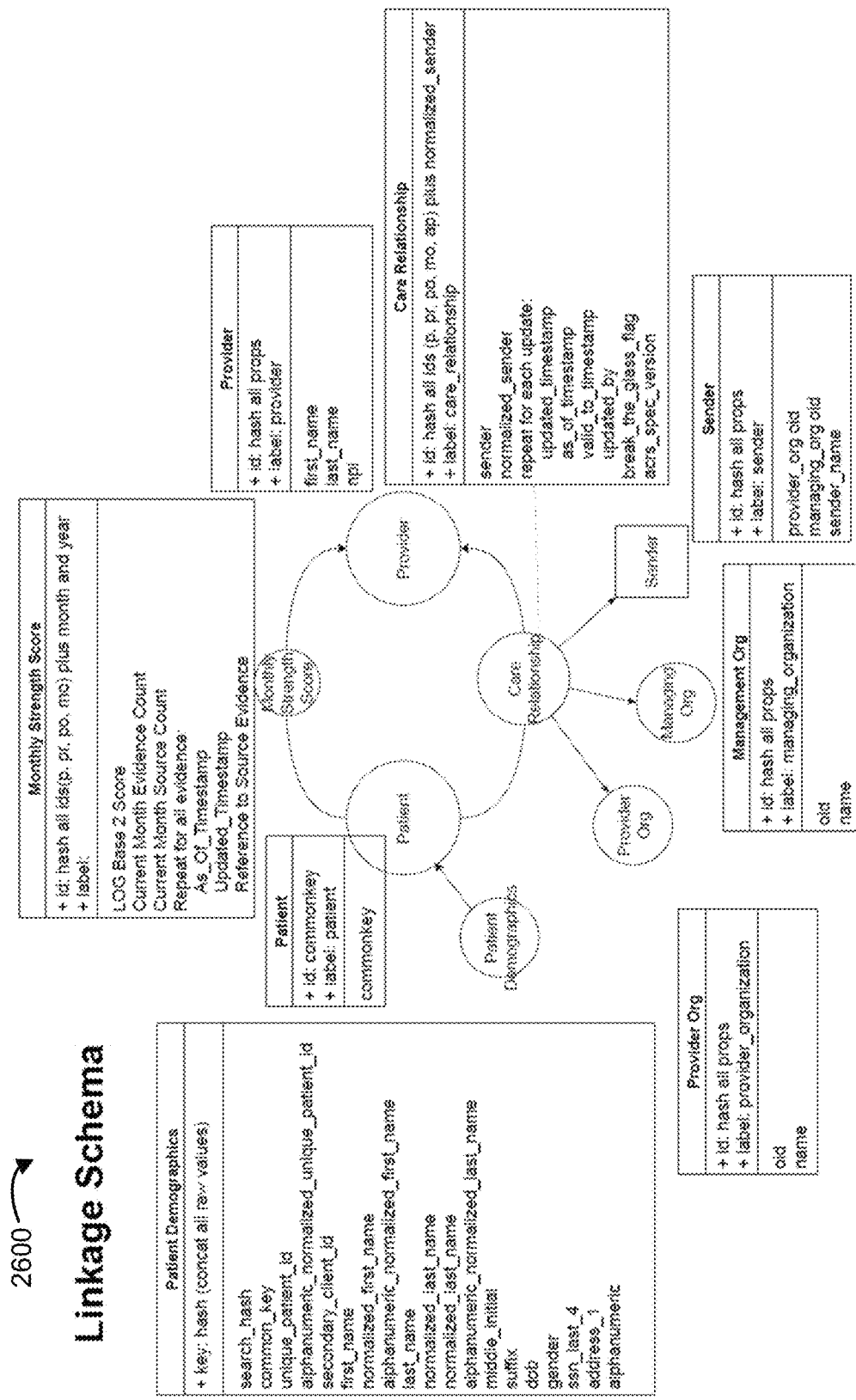
FIG. 26 is an illustration of an example linkage schema of a node graph data structure, in accordance with some embodiments.

FIG. 26 is an illustration of an example linkage schema of a node graph data structure 2600, in accordance with some embodiments. The linkage schema illustrates the data structures of each of the nodes in node graph data structure 2600 as well as the data that is included in the data structures. As illustrated, a patient node may be linked to a clinic node via one or more time period edges and/or a relationship status node. The patient node may be linked to a patient demographics node. The patient node, the demographics node, and the time period edges may be similar to the patient and demographics nodes and the time period edges described with reference to FIG. 25. The clinic node may be or include a data structure that stores data for a first name, a last name, and/or a national provider identifier number. The clinic node may be linked to nodes identifying such data in node graph data structure or store the data itself. The clinic node may be identifiable with a hash of a concatenation of the data that identifies the clinic.

The patient node and the clinic node may be connected through a relationship status node. The relationship status node may be a data structure that stores data indicating time periods in which the patient received active care from the clinic. In some cases, the relationship status node may also store data indicating a sender that referred the patient to the clinic. The relationship status node may also include a label indicating the node as a relationship status node, such as "care relationship." The relationship status node may include a hash of the data stored in the relationship status node the data processing system may use to quickly identify the relationship status node when querying node graph data structure 2600.

The relationship status node may be linked to separate nodes for a provider organization, a management organization, and/or a sender. The nodes may each include a data structure that stores data. Each of the separate nodes may store a name of the entity the represents, a label indicating a type of the entity, and/or a hash of the data stored in the node. The sender node may additionally store the names of the provider and/or the management organization, in some embodiments.

Figure 27:
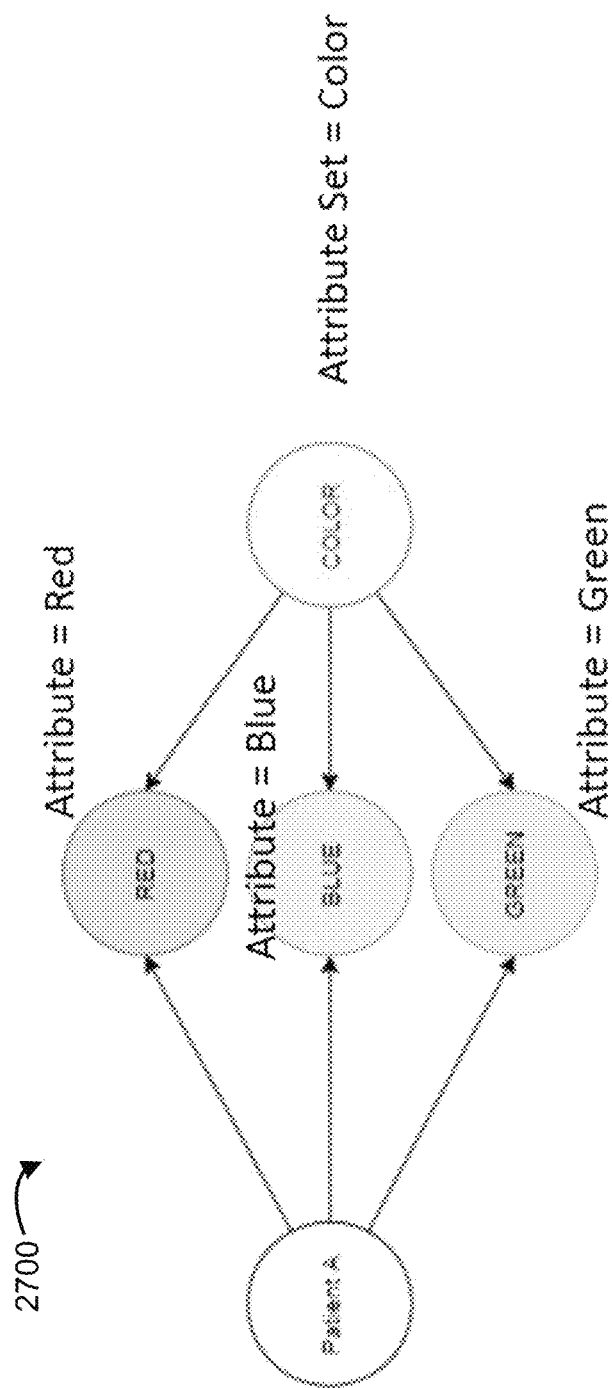
FIG. 27 is an illustration of an example patient node linked to a set of attribute nodes, in accordance with some embodiments.

FIG. 27 is an illustration of an example patient node linked to a set of attribute nodes in a node graph data structure 2700, in accordance with some embodiments. As illustrated, the patient node may have edges with three different attribute nodes associated with attributes (e.g., red, blue, and green) of the same type (e.g., color). Because the attributes may be attributes of the same type, the attribute may similarly be linked to an attribute type node indicating the attribute type. By including an attribute type node in node graph data structure 2700, a data processing system (e.g., a client device 308, 310, or 312 or a node graph generator 314, shown and described with reference to FIG. 3, a server system, etc.) may quickly retrieve data relating to patients that have any of the attributes of that type (e.g., the data processing system may identify the attribute type node and then identify the patient nodes that are linked to attribute nodes associated with attributes of the attribute type).

Figure 28:
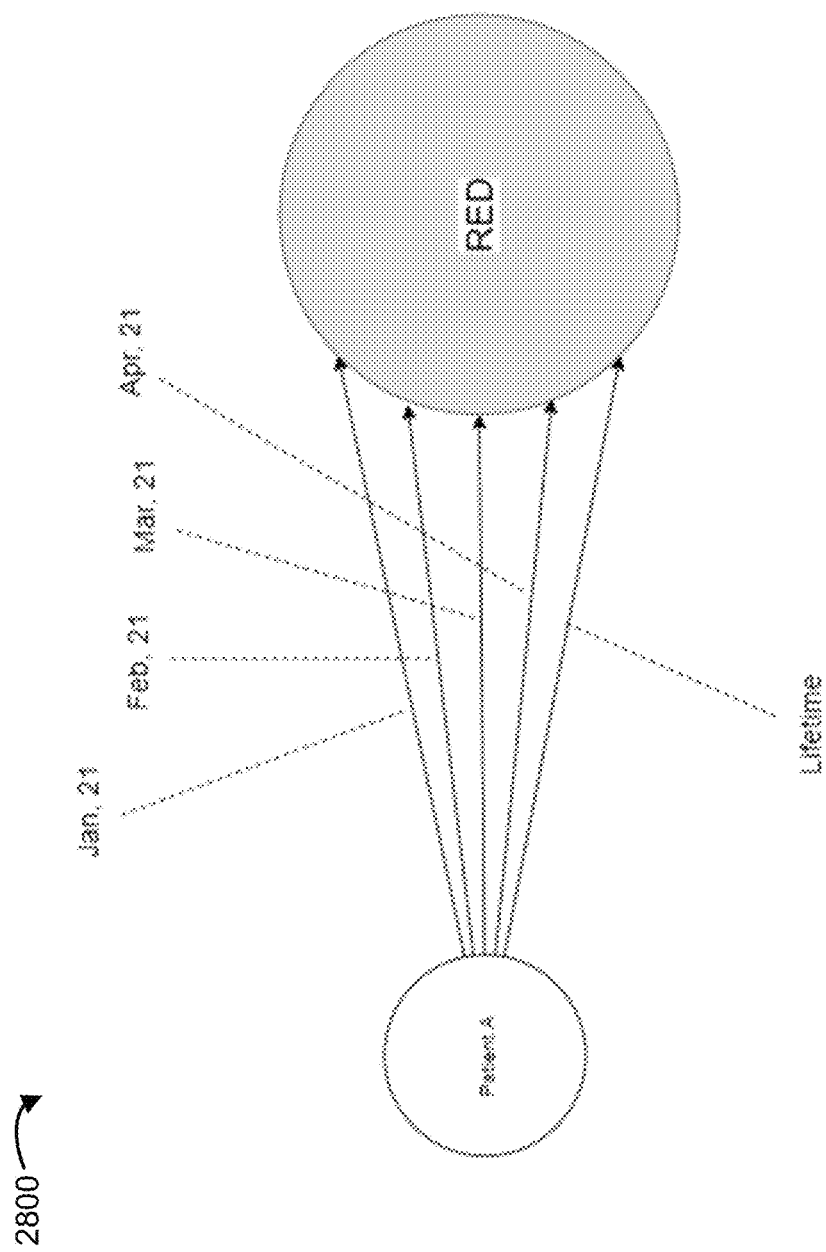
FIG. 28 is an illustration of an example patient node linked to an attribute node for separate time periods, in accordance with some embodiments.

FIG. 28 is an illustration of an example patient node linked to an attribute node (e.g., an attribute node for the "red" attribute) for separate time periods in a node graph data structure 2800, in accordance with some embodiments. As illustrated, the patient node may be linked, via edges, to the attribute node for four different time periods (e.g., months) and for a lifetime of the relationship between the patient node and the attribute node. Each edge may have its own weight indicating the strength of the relationship for the respective time period, as calculated based on evidence that was used to generate and update the weight. By storing multiple time period-based edges between two nodes in node graph data structure 2800, a data processing system (e.g., a client device 308, 310, or 312 or a node graph generator 314, shown and described with reference to FIG. 3, a server system, etc.) may retrieve data from the node graph data structure according to a requested time period.

Figure 29:
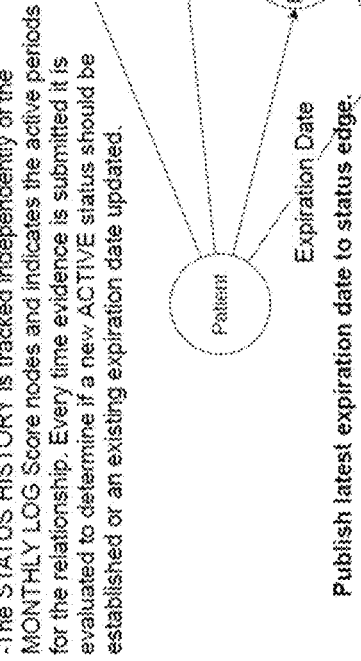
FIG. 29 is an illustration of an example patient node linked to a clinic node via time period nodes and a status history node, in accordance with some embodiments.

FIG. 29 is an illustration of an example patient node linked to a clinic node via time period nodes and a status history node in a node graph data structure 2900, in accordance with some embodiments. The time period nodes may be or represent the data structures for the edges between the patient node and the clinic node. For instance, the time period nodes may each include a weight for an edge according to evidence that is associated with the respective edge time periods, an evidence count for the time period, a data source count for the time period, pointers to the evidence that was used to calculate the weight for the time period, and time stamps indicating times associated with the evidence. The relationship status node may be or include a status history of the care the patient associated with the patient received from the clinic associated with the clinic node. The relationship status node may contain an active/inactive status history for the relationship as well as the future expiration date if the relationship currently has an active status. In one example, data in the relationship status node may include:

```
{
    "status_history": {
        "active_care": [
        {
            "id": "1234",
            "as_of": "2021-01-25T00:00:000Z"
            "expiration_timestamp": "2021-03-25T00:00:00.000Z"
        },
        {
            "id": "1235",
            "as_of": "2021-04-25T00:00:000Z"
            "expiration_timestamp": "2021-07-25T00:00:00.000Z"
```

-continued

```
        },
        {
            "id": "1236",
            "as_of": "2021-08-25T00:00:000Z"
            "expiration_timestamp": "2021-11-25T00:00:00.000Z"
        },
        ]
    }
}
```

In the above example, the relationship status node may include active status time periods between the "as of" dates and times and the "expiration timestamps." The data processing system may identify the active status time periods when determining time periods in which a patient was actively receiving care from a clinic.

Figure 30:
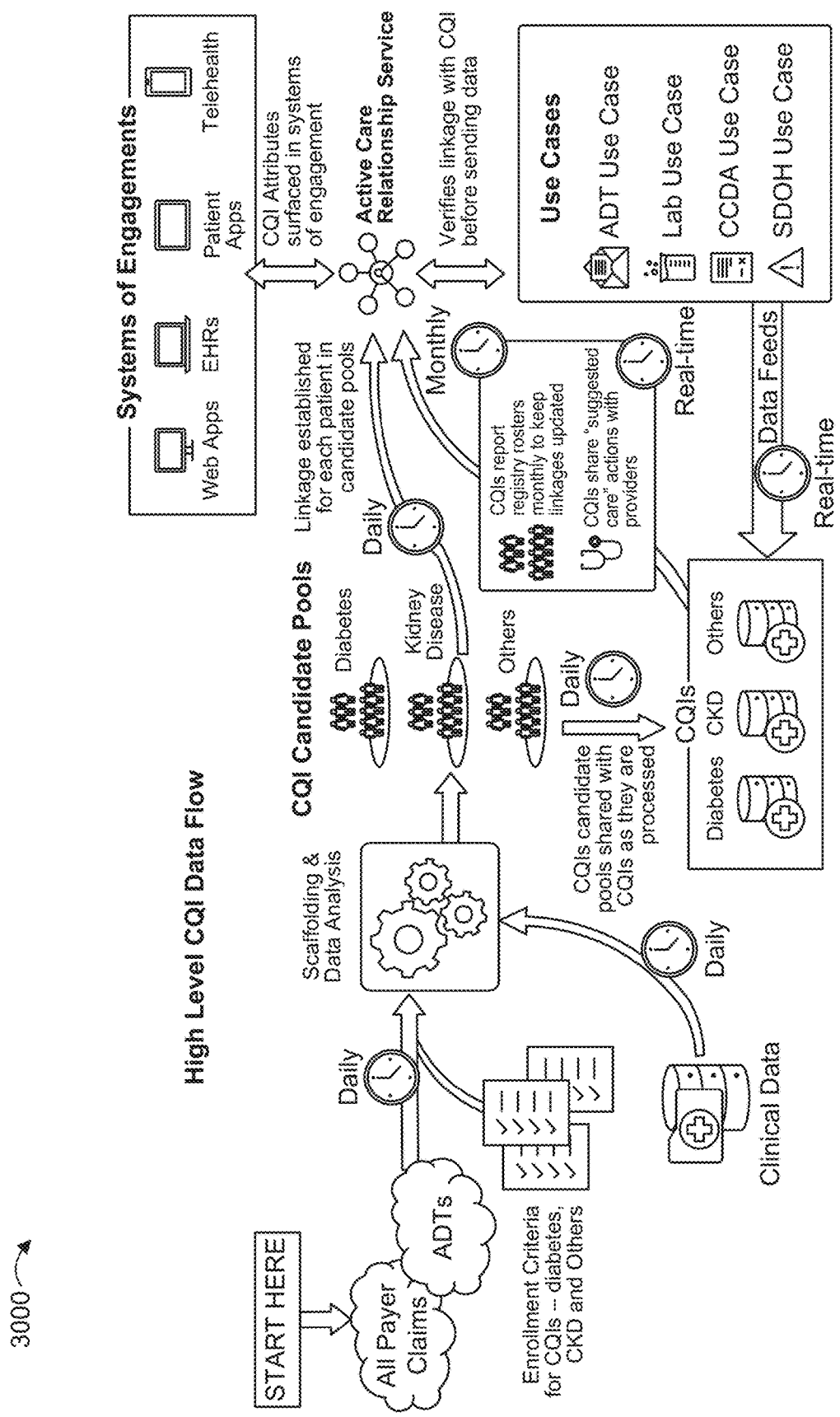
FIG. 30 is an illustration of an example sequence for using a node graph data structure for care quality improvement, in accordance with some embodiments.

FIG. 30 is an illustration of an example sequence 3000 for using a node graph data structure for care quality improvement (CQI), in accordance with some embodiments. In sequence 3000, a data processing system (e.g., a client device 308, 310, or 312 or a node graph generator 314, shown and described with reference to FIG. 3, a server system, etc.) may receive data containing documents for different patients and upload data from the documents into a node graph data structure. The data processing system may additionally receive indications that the patients are in different CQI candidate pools, such as CQI candidate pools for diabetes, kidney disease, etc. Upon receiving such indications, the data processing system may create CQI candidate pool nodes for the different candidate pools and generate edges between the patient nodes for the patients in the candidate pools and the corresponding CQI candidate pool nodes. The data processing system may receive such data at set time periods, such as daily or monthly. By doing so, the data processing system may quickly retrieve lists of patients in the different CQI candidate pools upon receipt of requests.

Figure 31:
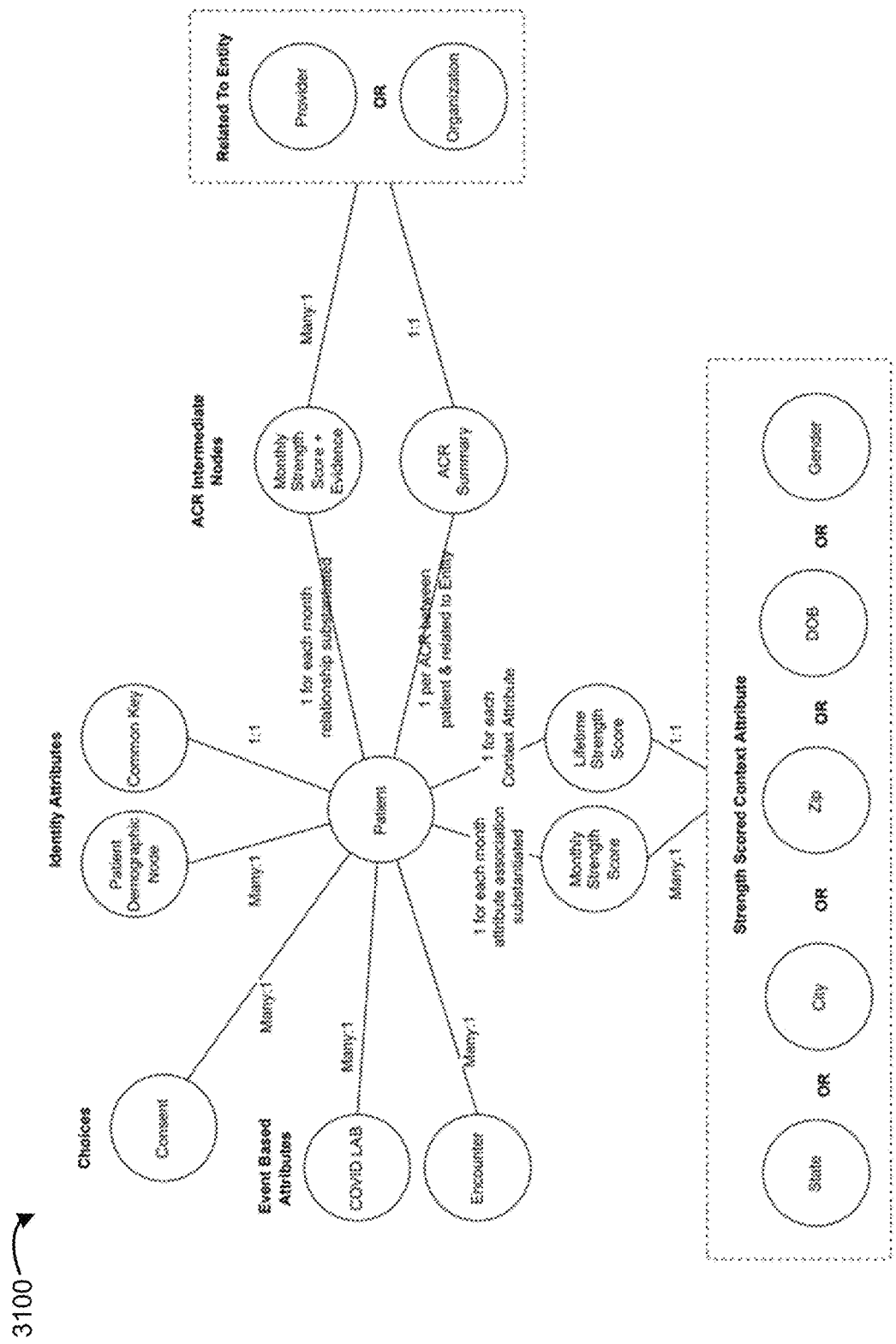
FIG. 31 is an illustration of an example node graph data structure, in accordance with some embodiments.

FIG. 31 is an illustration of an example node graph data structure 3100, in accordance with some embodiments. As illustrated, node graph data structure 3100 may include an entity node (e.g., a patient node) linked to different attribute nodes. The entity node can be linked to different attribute nodes that correspond to different types of attributes. For example, the entity node can be linked to attribute nodes corresponding to identity attributes, such as patient demographics or a common key for the entity node within node graph data structure 3100. The entity node can be linked to choice nodes that correspond to choices the entity has made (e.g., types of surgery the entity has choices to undertake or identifications of whether the entity has given consent for different procedures). The entity node can be linked to event-based attributes, such as encounters between the entity and a healthcare provider (e.g., a clinician or doctor) or lab results the entity has obtained. The entity node can be linked to different context attribute nodes, such as attribute nodes for address, date of birth, or gender. The entity node can be linked to individual context-based attribute nodes through different edges that each correspond to a different time period or a lifetime, for example. The entity node can be linked to group entity nodes (e.g., clinic nodes). The group entity nodes can correspond to clinics such as different healthcare providers or healthcare organizations. The entity node can be linked to the group entity nodes through multiple edges, one or more edges that correspond to data structures for different time periods and evidence that corresponds to such time periods, and an edge that corresponds to a summary of data for the patient that corresponds to the group entity. Such edges can link the entity node through intermediate nodes between the entity node and the group entity node.

Figure 32:
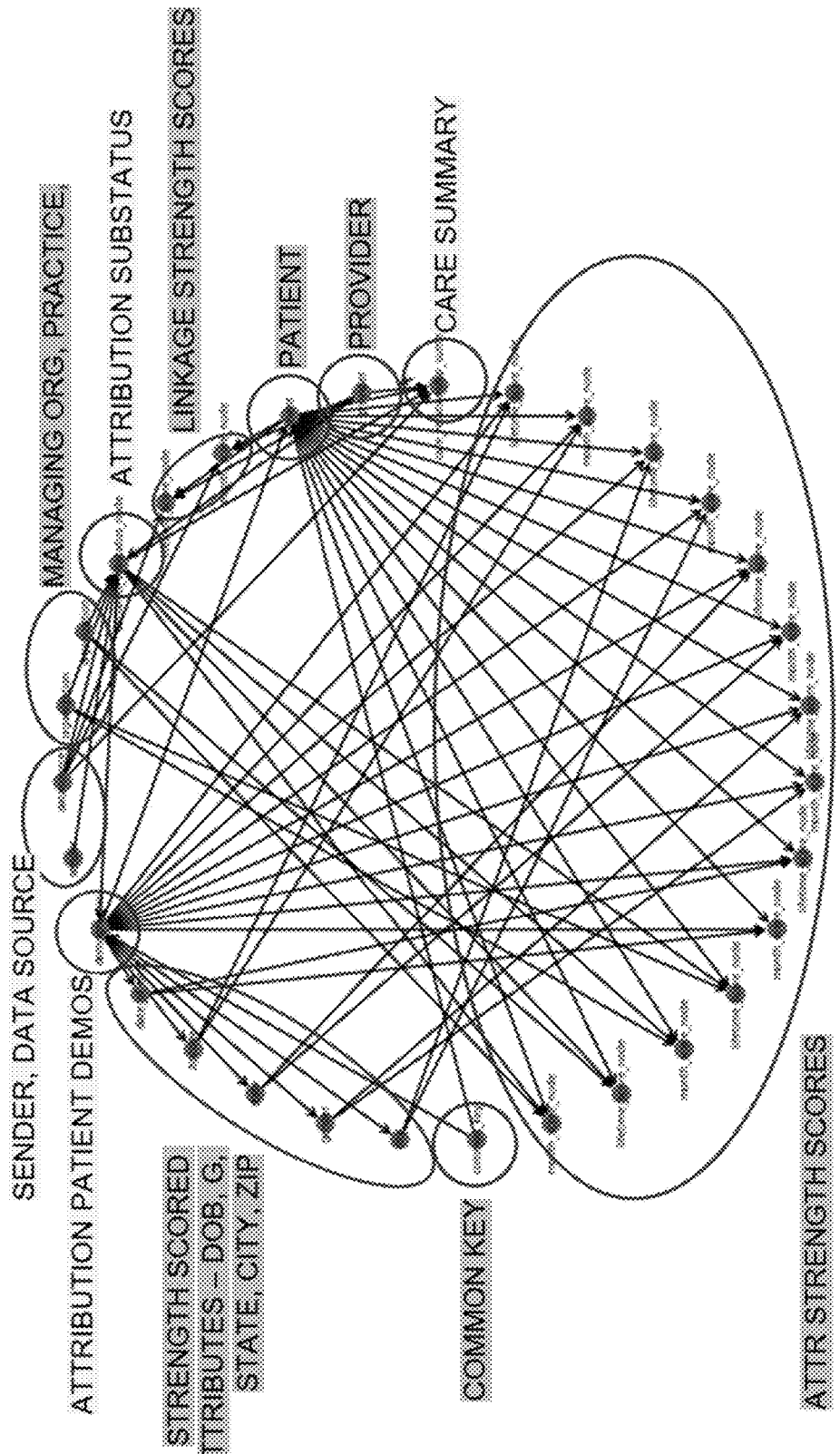
FIG. 32 is an illustration of an example node graph data structure, in accordance with some embodiments.

FIG. 32 is an illustration of an example node graph data structure 3200, in accordance with some embodiments. As illustrated, node graph data structure 3200 may include an entity node (e.g., a patient node) linked to different attribute nodes. The node graph data structure 3200 may be another representation of the node graph data structure 3100, shown and described with reference to FIG. 31.

In summary, by implementing the systems and methods described herein, a computer may receive and organize data about patients from a large number of clinics in a node graph data structure. In doing so, the data processing system may be able to provide data received from one clinic to clinicians operating at other clinics. This may be particularly useful if a clinician requests previous diagnoses or lab results about a patient while providing treatment to the patient and needs the information quickly. The data processing system may receive such requests and retrieve the requested data by traversing the edges and nodes of the node graph data structure instead of querying the databases of other clinics or searching through thousands of entries in a single database for all data that satisfies the clinician's requests. By implementing the systems and methods described herein, the computer may further enable the clinician to tailor the search to specific time periods and confidences so the clinician can receive relevant data to form a new diagnosis for the patient. The computer may further update its database over time prioritizing data that may create new relationships between nodes and/or strengthen important information such as PHI to ensure the data is shareable more quickly than data that is less likely to aid the clinician in performing a diagnosis.

In one aspect, the present disclosure describes a method for prioritized updating of a node graph data structure. The method may include storing, by one or more processors, a node graph comprising a plurality of patient nodes and a plurality of attribute nodes, each patient node of the plurality of patient nodes associated with a different patient that has visited a clinic for care and each attribute node of the plurality of attribute nodes associated with a different attribute of patients represented in the node graph by patient nodes; receiving, by the one or more processors, a set of data from one or more data sources, each of the one or more data sources corresponding to a different clinic visited by one or more patients represented in the node graph; inserting, by the one or more processors from the set of data, a first piece of data regarding a first patient having a first patient node in the node graph into a first queue responsive to determining the first piece of data comprises a first type of information, and a second piece of data regarding a second patient having a second patient node in the node graph into a second queue responsive to determining the second piece of data comprises a second type of information; and updating, by the one or more processors, the node graph with the first piece of data prior to updating the node graph with the second piece of data based on priority information of the first queue and the second queue.

In some embodiments, the first queue corresponds to a higher priority than the second queue, and wherein inserting the first piece of data regarding the first patient into the first comprises: determining, by the one or more processors, the first piece of data comprises protected health information of the first patient; and inserting, by the one or more processors, the first piece of data into the first queue based on the determining the first piece of data comprises protected health information. In some embodiments, determining the first piece of data comprises protected health information comprises using natural language processing techniques or object recognition techniques on the first piece of data.

In some embodiments, the first queue corresponds to a higher priority than the second queue, and wherein inserting the second piece of data regarding the second patient into the second queue comprises: determining, by the one or more processors, the second piece of data comprises demographic information of the second patient; and inserting, by the one or more processors, the second piece of data into the second queue based on the determining the second piece of data comprises demographic information.

In some embodiments, the first queue corresponds to a higher priority than the second queue, and wherein inserting the first piece of data regarding the first patient comprises: determining, by the one or more processors, the first piece of data originated from a type of document associated with the first queue; and inserting, by the one or more processors, the first piece of data into the first queue based on the determining the first piece of data originated from the type of document associated with the first queue.

In some embodiments, the type of document comprises an admission discharge and transfer document. In some embodiments, the first queue corresponds to a higher priority than the second queue, and wherein inserting the first piece of data regarding the first patient comprises: determining, by the one or more processors, the first piece of data comprises a file type of associated with the first queue; and inserting, by the one or more processors, the first piece of data into the first queue based on the determining the first piece of data comprises the file type associated with the first queue. In some embodiments, the first piece of data is a data file containing an electronic document generated at a clinic that provided care to the first patient. In some embodiments, the priority information indicates the first queue has a higher priority than the second queue.

In another aspect, the present disclosure describes a method for updating a node graph. The method may include storing, by one or more processors, a node graph comprising a plurality of patient nodes and a plurality of attribute nodes, each patient node of the plurality of patient nodes associated with a different patient that has visited a clinic for care and each attribute node of the plurality of attribute nodes associated with a different attribute of patients represented in the node graph by patient nodes; receiving, by the one or more processors from a data source during a plurality of time periods, a plurality of data files comprising data for a first patient, the data source corresponding to a clinic visited by one or more patients represented in the node graph; identifying, by the one or more processors, a plurality of edges between a first patient node of the plurality of patient nodes that identifies the first patient and a first attribute node of the plurality of attribute nodes that identifies a first attribute of the first patient, each of the plurality of edges corresponding to a value and a different time period of the plurality of time periods, the value indicating a confidence in the edge between the first patient node and the first attribute node for the time period of the edge; and for each of the plurality of data files, updating, by the one or more processors, a value for an edge of the plurality of edges that corresponds to a time period associated with the data file.

In some embodiments, updating the value for the edge comprises identifying, by the processor, a weight associated with the data source; and aggregating, by the processor, the value for the edge with a second value corresponding to the weight associated with the data source. In some embodiments, the method further includes incrementing, by the one or more processors, a counter for each data source that provided a data file based on which the value was determined; and storing, by the one or more processors in a data structure associated with the edge, a count of the counter. In some embodiments, updating the value for the edge comprises: identifying, by the one or more processors, a document type of a document stored in the data file; identifying, by the one or more processors, a weight associated with the document type; and aggregating, by the one or more processors, the value for the edge with a second value corresponding to the weight associated with the document.

In some embodiments, updating the value for the edge comprises: identifying, by the one or more processors, a first weight associated with the data source; identifying, by the one or more processors, a document type of a document stored in the data file; identifying, by the one or more processors, a second weight associated with the document type; calculating, by the one or more processors, an evidence weight for the data file based on the first weight and the second weight; and aggregating, by the one or more processors, the value for the edge with the evidence weight for the data file.

In some embodiments, the method further includes receiving, by the one or more processors, a second data file comprising data for the first patient and the first attribute of the first patient and associated with a second time period; responsive to receiving the second data file, determining, by the one or more processors, there is not an edge between the first patient node of the first patient and the first attribute node of the first attribute for the second time period; and generating, by the one or more processors, a second edge for the second time period between the first patient node and the first attribute node responsive to receiving the second data file associated with the second time period and determining there is not an edge between the first patient node of the first patient and the first attribute node of the first attribute for the second time period.

In some embodiments, generating the second edge for the second time period comprises: assigning, by the one or more processors and based on the second data file, a second value indicating a second confidence in the second edge between the first patient node and the first attribute for the second time period. In some embodiments, the method further includes identifying, by the one or more processors, a time stamp for each of the plurality of data files based on text in the data file, a time in which the one or more processors received the data file, or a timestamp in a data packet containing the data file; and determining, by the one or more processors, time periods for the plurality of data files based on the identified time stamps. In some embodiments, the plurality of data files comprise one or more of an admission discharge and transfer document, a consolidated clinical document architecture document, a social determinants of health document, an attribution file, or a pre-adjudicated claim.

In another aspect, the present disclosure describes a method for data storage and retrieval. The method may include storing, by one or more processors, a node graph comprising a plurality of patient nodes and a plurality of clinic nodes, each patient node of the plurality of patient nodes associated with a different patient that has visited a clinic for care and each clinic node of the plurality of attribute nodes associated with a different clinic of the clinics visited by patients represented in the node graph by patient nodes; linking, by the one or more processors, a patient node of the plurality of patient nodes with a clinic node of the plurality of clinic nodes through a relationship status node, the relationship status node having an inactive status indicating a patient associated with the patient node is currently not receiving clinical care from a clinic associated with the clinic node; receiving, by the one or more processors from a data source corresponding to the clinic, a data file comprising data identifying the patient; and adding, by the processor, a string comprising an active status to the relationship status node responsive to the data file comprising the data identifying the patient.

In some embodiments, adding the string comprising the active status to the relationship status node comprises adding, by the one or more processors, an expiration date of the active status to the relationship status node. In some embodiments, adding the string comprising the active status to the relationship status node comprises adding, by the one or more processors, a beginning date of the active status to the relationship status node. In some embodiments, the method further includes determining, by the one or more processors, an expiration date of the active status by aggregating a defined value with the beginning date. In some embodiments, the method further includes receiving, by the one or more processors, a request for data regarding the patient; identifying, by the one or more processors, the active status of the relationship node linking the patient node with the clinic node; and retrieving, by the one or more processors, data regarding the patient and corresponding to the clinic node responsive to determining the relationship node linking the patient node with the clinic node indicates an active status.

In some embodiments, retrieving the data comprises identifying, by the one or more processors, one or more pointers in an edge between the patient node and the clinic node; using, by the one or more processors, the one or more pointers to access a database that stores data regarding the patient for the clinic; and retrieving the data regarding the patient for the clinic from the accessed database. In some embodiments, the method further includes receiving, by the one or more processors from a computing device, a request for a list of clinics with which the patient is receiving active care; identifying, by the one or more processors, each relationship node in the node graph that links the patient node with a different clinic; generating, by the one or more processors, a record comprising a list of clinics with clinic nodes linked with the patient node through a relationship node having an active status; and transmitting, by the one or more processors, the record to the requesting computing device.

In another aspect, the present disclosure describes a method for data storage and retrieval. The method may include storing, by one or more processors, a node graph comprising a plurality of patient nodes and a plurality of attribute nodes, each patient node of the plurality of patient nodes associated with a different patient that has visited a clinic for care and each attribute node of the plurality of attribute nodes associated with a different attribute of patients represented in the node graph by patient nodes, data for the attribute nodes stored in the node graph based on data files received from clinics visited by the patients for care; receiving, by the one or more processors from a client device, a request for data comprising a plurality of identifications of a plurality of attributes; identifying, by the one or more processors, a plurality of attribute nodes responsive to each attribute node of the plurality of attribute nodes having a matching identifier to an identification of the plurality of identifications; selecting, by the one or more processors, a set of patient nodes associated with a set of patients responsive to determining each patient node of the set has an edge with each of the plurality of attribute nodes; and transmitting, by the one or more processors, a record identifying the set of patients to the client device.

In some embodiments, the method further includes incrementing, by the one or more processors, a counter for each patient node of the set of patient nodes, wherein the record further identifies a count of the counter. In some embodiments, the method further includes identifying, by the one or more processors, a patient node that has at least one edge with the identified plurality of attribute nodes; and determining, by the one or more processors, the patient node has an edge with each of the plurality of attribute nodes, wherein selecting the set of patient nodes is performed in response to the determining the patient node has an edge with each of the plurality of attribute nodes. In some embodiments, determining the patient node has an edge with each of the plurality of attribute nodes comprises determining, by the one or more processors, the patient node has an edge with a weight exceeding a threshold with each of the plurality of attribute nodes. In some embodiments, the plurality of attribute nodes comprises a subset of demographic nodes identifying patient demographic attributes and a subset of lab result nodes identifying patient lab results.

In another aspect, the present disclosure describes a method for data storage and retrieval. The method may include storing, by a processor, a node graph comprising a plurality of entity nodes and a plurality of attribute nodes, each entity node of the plurality of entity nodes associated with a different entity and each attribute node of the plurality of attribute nodes associated with a different attribute; receiving, by the processor from a client device, a request for data comprising an identification of a first entity; identifying, by the processor, an entity node associated with the first entity based on the identification; selecting, by the processor, a set of attribute nodes associated with a set of attributes responsive to determining each attribute node of the set of attribute nodes has an edge with the entity node; and transmitting, by the processor, a record identifying the set of attributes to the client device.

In some embodiments, selecting the set of attribute nodes comprises selecting, by the processor, the set of attribute nodes responsive to each of the set of attribute nodes having a weight exceeding a threshold. In some embodiments, the receiving the request for data comprises receiving a request for lab result data generated about the first entity; and wherein selecting the set of attribute nodes comprises selecting, by the processor, the set of attributes responsive to determining each attribute node of the contains lab result data. In some embodiments, the method further includes generating, by the processor, a first edge between the patient node and a first attribute node of the set of attribute nodes responsive to receiving a first data file from a first data source; and generating, by the processor, a second edge between the patient node and a second attribute node of the set of attribute nodes responsive to receiving a second data from a second data source.

B. Computing Environment

Having discussed specific embodiments of the present solution, it may be helpful to describe aspects of the operating environment as well as associated system components (e.g., hardware elements) in connection with the methods and systems described herein.

Figure 33A:
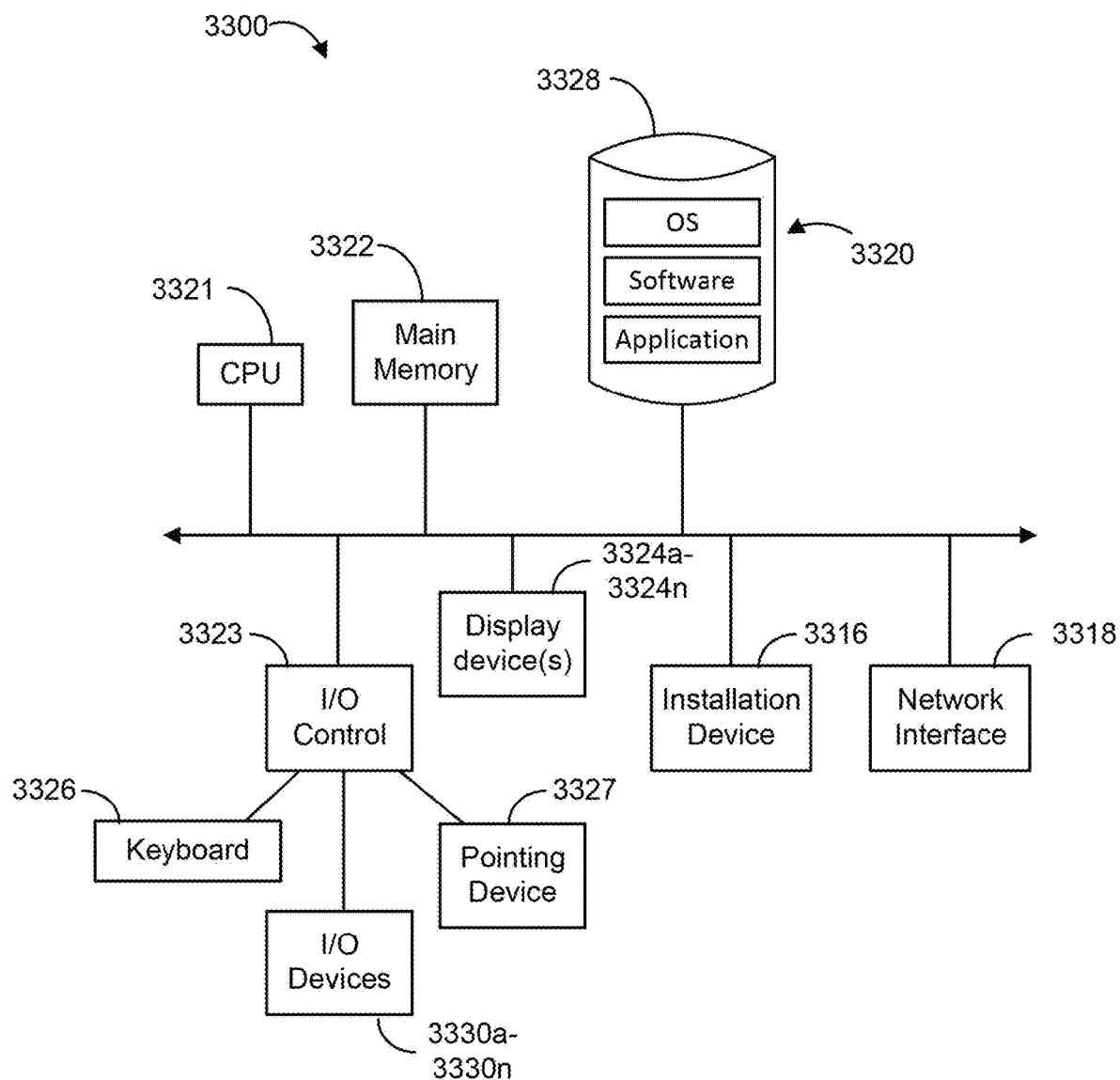
FIGS. 33A and 33B are block diagrams depicting embodiments of computing devices useful in connection with the methods and systems described herein.
Figure 33B:
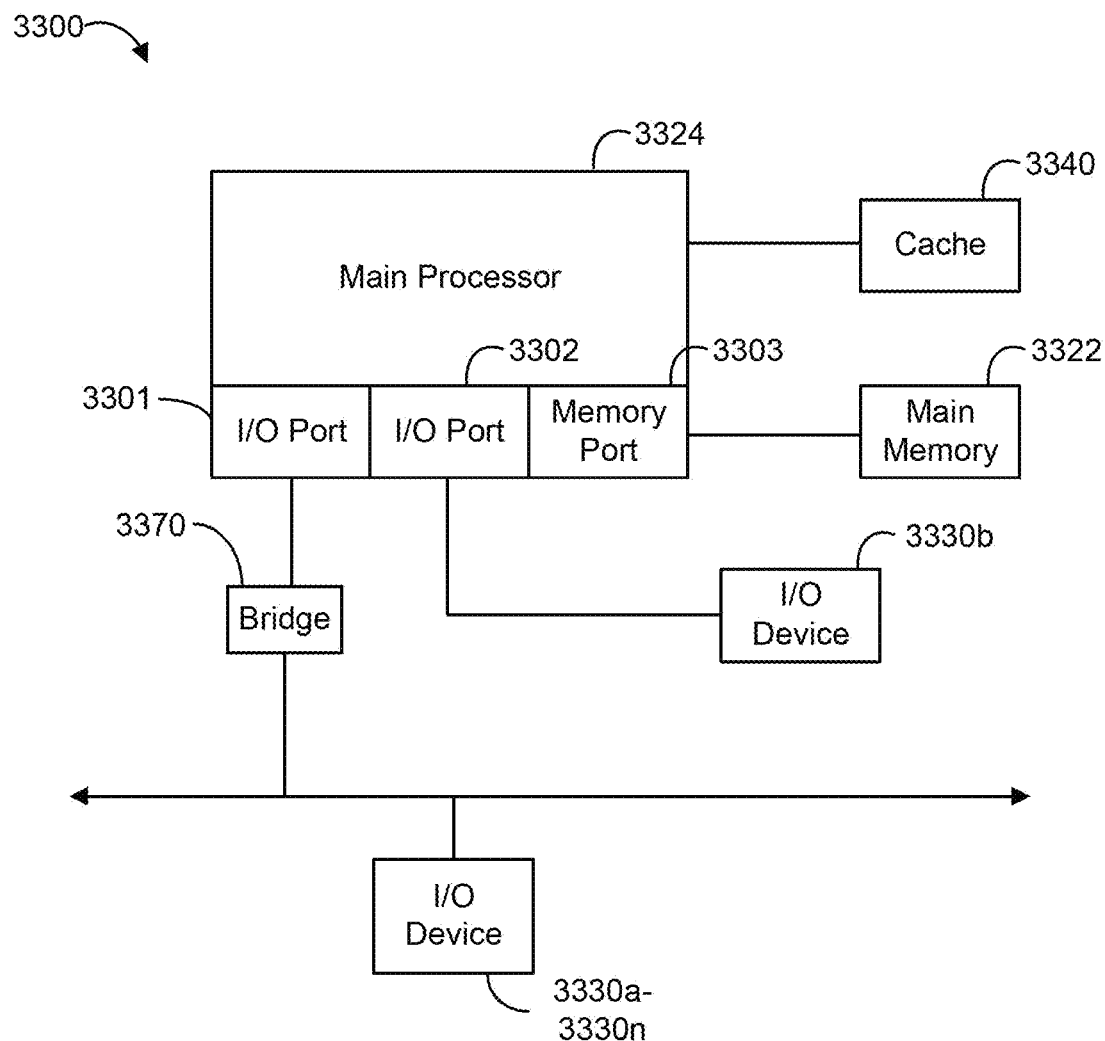

The systems discussed herein may be deployed as and/or executed on any type and form of computing device, such as a computer, network device or appliance capable of communicating on any type and form of network and performing the operations described herein. FIGS. 33A and 33B depict block diagrams of a computing device 3300 useful for practicing an embodiment of the wireless communication devices 3302 or the access point 3306. As shown in FIGS. 33A and 33B, each computing device 3300 includes a central processing unit 3321, and a main memory unit 3322. As shown in FIG. 33A, a computing device 3300 may include a storage device 3328, an installation device 3316, a network interface 3318, an I/O controller 3323, display devices 3324a-3324n, a keyboard 3326 and a pointing device 3327, such as a mouse. The storage device 3328 may include, without limitation, an operating system and/or software. As shown in FIG. 33B, each computing device 3300 may also include additional optional elements, such as a memory port 3303, a bridge 3370, one or more input/output devices 3330a-3330n (generally referred to using reference numeral 3330), and a cache memory 3340 in communication with the central processing unit 3321.

The central processing unit 3321 is any logic circuitry that responds to and processes instructions fetched from the main memory unit 3322. In many embodiments, the central processing unit 3321 is provided by a microprocessor unit, such as: those manufactured by Intel Corporation of Mountain View, California; those manufactured by International Business Machines of White Plains, New York; or those manufactured by Advanced Micro Devices of Sunnyvale, California. The computing device 3300 may be based on any of these processors, or any other processor capable of operating as described herein.

Main memory unit 3322 may be one or more memory chips capable of storing data and allowing any storage location to be directly accessed by the microprocessor 3321, such as any type or variant of Static random access memory (SRAM), Dynamic random access memory (DRAM), Ferroelectric RAM (FRAM), NAND Flash, NOR Flash and Solid State Drives (SSD). The main memory 3322 may be based on any of the above described memory chips, or any other available memory chips capable of operating as described herein. In the embodiment shown in FIG. 33A, the processor 3321 communicates with main memory 3322 via a system bus 3380 (described in more detail below). FIG. 33B depicts an embodiment of a computing device 3300 in which the processor communicates directly with main memory 3322 via a memory port 3303. For example, in FIG. 33B the main memory 3322 may be DRDRAM.

FIG. 33B depicts an embodiment in which the main processor 3321 communicates directly with cache memory 3340 via a secondary bus, sometimes referred to as a backside bus. In other embodiments, the main processor 3321 communicates with cache memory 3340 using the system bus 3380. Cache memory 3340 typically has a faster response time than main memory 3322 and is provided by, for example, SRAM, BSRAM, or EDRAM. In the embodiment shown in FIG. 33B, the processor 3321 communicates with various I/O devices 3330 via a local system bus 3380. Various buses may be used to connect the central processing unit 3321 to any of the I/O devices 3330, for example, a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 3324, the processor 3321 may use an Advanced Graphics Port (AGP) to communicate with the display 3324. FIG. 33B depicts an embodiment of a computer 3300 in which the main processor 3321 may communicate directly with I/O device 3330b, for example via HYPERTRANSPORT, RAPIDIO, or INFINIBAND communications technology. FIG. 33B also depicts an embodiment in which local busses and direct communication are mixed: the processor 3321 communicates with I/O device 3330a using a local interconnect bus while communicating with I/O device 3330b directly.

A wide variety of I/O devices 3330a-3330n may be present in the computing device 3300. Input devices include keyboards, mice, trackpads, trackballs, microphones, dials, touch pads, touch screen, and drawing tablets. Output devices include video displays, speakers, inkjet printers, laser printers, projectors and dye-sublimation printers. The I/O devices may be controlled by an I/O controller 3323 as shown in FIG. 33A. The I/O controller may control one or more I/O devices such as a keyboard 3326 and a pointing device 3327, e.g., a mouse or optical pen. Furthermore, an I/O device may also provide storage and/or an installation medium 3316 for the computing device 3300. In still other embodiments, the computing device 3300 may provide USB connections (not shown) to receive handheld USB storage devices such as the USB Flash Drive line of devices manufactured by Twintech Industry, Inc. of Los Alamitos, California.

Referring again to FIG. 33A, the computing device 3300 may support any suitable installation device 3316, such as a disk drive, a CD-ROM drive, a CD-R/RW drive, a DVD-ROM drive, a flash memory drive, tape drives of various formats, USB device, hard-drive, a network interface, or any other device suitable for installing software and programs. The computing device 3300 may further include a storage device, such as one or more hard disk drives or redundant arrays of independent disks, for storing an operating system and other related software, and for storing application software programs such as any program or software 3320 for implementing (e.g., configured and/or designed for) the systems and methods described herein. Optionally, any of the installation devices 3316 could also be used as the storage device. Additionally, the operating system and the software can be run from a bootable medium.

Furthermore, the computing device 3300 may include a network interface 3318 to interface to the network 3304 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, IEEE 802.11ac, IEEE 802.11ad, CDMA, GSM, WiMax and direct asynchronous connections). In one embodiment, the computing device 3300 communicates with other computing devices 3300' via any type and/or form of gateway or tunneling protocol such as Secure Socket Layer (SSL) or Transport Layer Security (TLS). The network interface 3318 may include a built-in network adapter, network interface card, PCMCIA network card, card bus network adapter, wireless network adapter, USB network adapter, modem or any other device suitable for interfacing the computing device 3300 to any type of network capable of communication and performing the operations described herein.

In some implementations, the computing device 3300 may include or be connected to one or more display devices 3324a-3324n. As such, any of the I/O devices 3330a-3330n and/or the I/O controller 3323 may include any type and/or form of suitable hardware, software, or combination of hardware and software to support, enable or provide for the connection and use of the display device(s) 3324a-3324n by the computing device 3300. For example, the computing device 3300 may include any type and/or form of video adapter, video card, driver, and/or library to interface, communicate, connect or otherwise use the display device(s) 3324a-3324n. In one embodiment, a video adapter may include multiple connectors to interface to the display device(s) 3324a-3324n. In other embodiments, the computing device 3300 may include multiple video adapters, with each video adapter connected to the display device(s) 3324a-3324n. In some implementations, any portion of the operating system of the computing device 3300 may be configured for using multiple displays 3324a-3324n. One ordinarily skilled in the art will recognize and appreciate the various ways and embodiments that a computing device 3300 may be configured to have one or more display devices 3324a-3324n.

In further embodiments, an I/O device 3330 may be a bridge between the system bus 3380 and an external communication bus, such as a USB bus, an Apple Desktop Bus, an RS-232 serial connection, a SCSI bus, a FireWire bus, a FireWire 500 bus, an Ethernet bus, an AppleTalk bus, a Gigabit Ethernet bus, an Asynchronous Transfer Mode bus, a FibreChannel bus, a Serial Attached small computer system interface bus, a USB connection, or a HDMI bus.

A computing device 3300 of the sort depicted in FIGS. 33A and 33B may operate under the control of an operating system, which control scheduling of tasks and access to system resources. The computing device 3300 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: Android, produced by Google Inc.; WINDOWS 7 and 8, produced by Microsoft Corporation of Redmond, Washington; MAC OS, produced by Apple Computer of Cupertino, California; WebOS, produced by Research In Motion (RIM); OS/2, produced by International Business Machines of Armonk, New York; and Linux, a freely-available operating system distributed by Caldera Corp. of Salt Lake City, Utah, or any type and/or form of a Unix operating system, among others.

The computer system 3300 can be any workstation, telephone, desktop computer, laptop or notebook computer, server, handheld computer, mobile telephone or other portable telecommunications device, media playing device, a gaming system, mobile computing device, or any other type and/or form of computing, telecommunications or media device that is capable of communication. The computer system 3300 has sufficient processor power and memory capacity to perform the operations described herein.

In some implementations, the computing device 3300 may have different processors, operating systems, and input devices consistent with the device. For example, in one embodiment, the computing device 3300 is a smart phone, mobile device, tablet or personal digital assistant. In still other embodiments, the computing device 3300 is an Android-based mobile device, an iPhone smart phone manufactured by Apple Computer of Cupertino, California, or a Blackberry or WebOS-based handheld device or smart phone, such as the devices manufactured by Research In Motion Limited. Moreover, the computing device 3300 can be any workstation, desktop computer, laptop or notebook computer, server, handheld computer, mobile telephone, any other computer, or other form of computing or telecommunications device that is capable of communication and that has sufficient processor power and memory capacity to perform the operations described herein.

Although the disclosure may reference one or more "users", such "users" may refer to user-associated devices or stations (STAs), for example, consistent with the terms "user" and "multi-user" typically used in the context of a multi-user multiple-input and multiple-output (MU-MIMO) environment.

Although examples of communications systems described above may include devices and APs operating according to an 802.11 standard, it should be understood that embodiments of the systems and methods described can operate according to other standards and use wireless communications devices other than devices configured as devices and APs. For example, multiple-unit communication interfaces associated with cellular networks, satellite communications, vehicle communication networks, and other non-802.11 wireless networks can utilize the systems and methods described herein to achieve improved overall capacity and/or link quality without departing from the scope of the systems and methods described herein.

It should be noted that certain passages of this disclosure may reference terms such as "first" and "second" in connection with devices, mode of operation, transmit chains, antennas, etc., for purposes of identifying or differentiating one from another or from others. These terms are not intended to merely relate entities (e.g., a first device and a second device) temporally or according to a sequence, although in some cases, these entities may include such a relationship. Nor do these terms limit the number of possible entities (e.g., devices) that may operate within a system or environment.

It should be understood that the systems described above may provide multiple ones of any or each of those components and these components may be provided on either a standalone machine or, in some implementations, on multiple machines in a distributed system. In addition, the systems and methods described above may be provided as one or more computer-readable programs or executable instructions embodied on or in one or more articles of manufacture. The article of manufacture may be a floppy disk, a hard disk, a CD-ROM, a flash memory card, a PROM, a RAM, a ROM, or a magnetic tape. In general, the computer-readable programs may be implemented in any programming language, such as LISP, PERL, C, C++, C #, PROLOG, or in any byte code language such as JAVA. The software programs or executable instructions may be stored on or in one or more articles of manufacture as object code.

While the foregoing written description of the methods and systems enables one of ordinary skill to make and use what is considered presently to be the best mode thereof, those of ordinary skill will understand and appreciate the existence of variations, combinations, and equivalents of the specific embodiment, method, and examples herein. The present methods and systems should therefore not be limited by the above described embodiments, methods, and examples, but by all embodiments and methods within the scope and spirit of the disclosure.

What is claimed is:

1. A method for prioritized updating of a node graph data structure, comprising:

storing, by one or more processors, a node graph comprising a plurality of patient nodes and a plurality of attribute nodes, each patient node of the plurality of patient nodes associated with a different patient that has visited a clinic for care and each attribute node of the plurality of attribute nodes associated with a different attribute of patients represented in the node graph by patient nodes;

receiving, by the one or more processors, a set of data from one or more data sources over a network, each of the one or more data sources corresponding to a different clinic visited by one or more patients represented in the node graph;

inserting, by the one or more processors from the set of data, a first piece of data regarding a first patient having a first patient node in the node graph into a first queue located in a first dedicated location in memory responsive to determining the first piece of data comprises a first type of information, and a second piece of data regarding a second patient having a second patient node in the node graph into a second queue in a second dedicated location in memory outside of the first dedicated location in the memory responsive to determining the second piece of data comprises a second type of information;

executing, by the one or more processors, a bulk loader file builder to generate a bulk file by inserting data, including the first piece of data, retrieved from the first queue instead of the second queue into the bulk file based on priority information of the first queue and the second queue, wherein using the priority information of the first queue and the second queue for data retrieval reduces the processing power and memory requirements of updating the node graph; and responsive to detecting the bulk file is at a capacity threshold, updating, by the one or more processors, the node graph with the bulk file containing the first piece of data in a first batch processing period and updating the node graph with the second piece of data in a second bulk file in a second batch processing period subsequent to the first batch processing period.

2. The method of claim 1, wherein the first queue corresponds to a higher priority than the second queue, and wherein inserting the first piece of data regarding the first patient into the first queue comprises:

determining, by the one or more processors, the first piece of data comprises protected health information of the first patient; and inserting, by the one or more processors, the first piece of data into the first queue based on the determining the first piece of data comprises protected health information.

3. The method of claim 2, wherein determining the first piece of data comprises protected health information comprises using natural language processing techniques or object recognition techniques on the first piece of data.

4. The method of claim 1, wherein the first queue corresponds to a higher priority than the second queue, and wherein inserting the second piece of data regarding the second patient into the second queue comprises:

determining, by the one or more processors, the second piece of data comprises demographic information of the second patient; and inserting, by the one or more processors, the second piece of data into the second queue based on the determining the second piece of data comprises demographic information.

5. The method of claim 1, wherein the first queue corresponds to a higher priority than the second queue, and wherein inserting the second piece of data regarding the second patient comprises:
   determining, by the one or more processors, the first piece of data originated from a type of document associated with the first queue; and
   inserting, by the one or more processors, the first piece of data into the first queue based on the determining the first piece of data originated from the type of document associated with the first queue.

6. The method of claim 5, wherein the type of document comprises an admission discharge and transfer document.

7. The method of claim 1, wherein the first queue corresponds to a higher priority than the second queue, and wherein inserting the first piece of data regarding the first patient comprises:
   determining, by the one or more processors, the first piece of data comprises a file type of associated with the first queue; and
   inserting, by the one or more processors, the first piece of data into the first queue based on the determining the first piece of data comprises the file type associated with the first queue.

8. The method of claim 7, wherein the first piece of data is a data file containing an electronic document generated at a clinic that provided care to the first patient.

9. The method of claim 1, wherein the priority information indicates the first queue has a higher priority than the second queue.

10. A system for prioritized updating of a node graph data structure, comprising:
   one or more processors coupled with memory and configured by computer-readable instructions to:
      store a node graph comprising a plurality of patient nodes and a plurality of attribute nodes, each patient node of the plurality of patient nodes associated with a different patient that has visited a clinic for care and each attribute node of the plurality of attribute nodes associated with a different attribute of patients represented in the node graph by patient nodes;
      receive a set of data from one or more data sources over a network, each of the one or more data sources corresponding to a different clinic visited by one or more patients represented in the node graph;
      insert, from the set of data, a first piece of data regarding a first patient having a first patient node in the node graph into a first queue located in a first dedicated location in memory responsive to determining the first piece of data comprises a first type of information, and a second piece of data regarding a second patient having a second patient node in the node graph into a second queue in a second dedicated location in memory outside of the first dedicated location in the memory responsive to determining the second piece of data comprises a second type of information;
      execute a bulk loader file builder to generate a bulk file by inserting data, including the first piece of data, retrieved from the first queue instead of the second queue into the bulk file based on priority information of the first queue and the second queue, wherein using the priority information of the first queue and the second queue for data retrieval reduces the processing power and memory requirements of updating the node graph; and
      responsive to detecting the bulk file is at a capacity threshold, update the node graph with the bulk file containing the first piece of data in a first batch processing period and updating the node graph with the second piece of data in a second bulk file in a second batch processing period subsequent to the first batch processing period.

11. The system of claim 10, wherein the first queue corresponds to a higher priority than the second queue, and wherein the instructions cause the one or more processors to insert the first piece of data regarding the first patient into the first queue by:
   determining the first piece of data comprises protected health information of the first patient; and
   inserting the first piece of data into the first queue based on the determining the first piece of data comprises protected health information.

12. The system of claim 11, wherein the instructions cause the one or more processors to determine the first piece of data comprises protected health information by using natural language processing techniques or object recognition techniques on the first piece of data.

13. The system of claim 10, wherein the first queue corresponds to a higher priority than the second queue, and wherein the instructions cause the one or more processors to insert the second piece of data regarding the second patient into the second queue by:
   determining the second piece of data comprises demographic information of the second patient; and
   inserting the second piece of data into the second queue based on the determining the second piece of data comprises demographic information.

14. The system of claim 10, wherein the first queue corresponds to a higher priority than the second queue, and wherein the instructions cause the one or more processors to insert the second piece of data regarding the second patient by:
   determining the first piece of data originated from a type of document associated with the first queue; and
   inserting the first piece of data into the first queue based on the determining the first piece of data originated from the type of document associated with the first queue.

15. The system of claim 14, wherein the type of document comprises an admission discharge and transfer document.

16. The system of claim 10, wherein the first queue corresponds to a higher priority than the second queue, and wherein the instructions cause the one or more processors to insert the first piece of data regarding the first patient comprises:
   determining the first piece of data comprises a file type of associated with the first queue; and
   inserting the first piece of data into the first queue based on the determining the first piece of data comprises the file type associated with the first queue.

17. The system of claim 10, wherein the priority information indicates the first queue has a higher priority than the second queue.

18. Non-transitory computer readable media for prioritized updating of a node graph data structure, comprising instructions which, when executed by one or more processors, cause the one or more processors to:
   store a node graph comprising a plurality of patient nodes and a plurality of attribute nodes, each patient node of the plurality of patient nodes associated with a different patient that has visited a clinic for care and each attribute node of the plurality of attribute nodes associated with a different attribute of patients represented in the node graph by patient nodes;

receive a set of data from one or more data sources over a network, each of the one or more data sources corresponding to a different clinic visited by one or more patients represented in the node graph;

insert, from the set of data, a first piece of data regarding a first patient having a first patient node in the node graph into a first queue located in a first dedicated location in memory responsive to determining the first piece of data comprises a first type of information, and a second piece of data regarding a second patient having a second patient node in the node graph into a second queue in a second dedicated location in memory outside of the first dedicated location in the memory responsive to determining the second piece of data comprises a second type of information;

execute a bulk loader file builder to generate a bulk file by inserting data, including the first piece of data, retrieved from the first queue instead of the second queue into the bulk file based on priority information of the first queue and the second queue, wherein using the priority information of the first queue and the second queue for data retrieval reduces the processing power and memory requirements of updating the node graph; and responsive to detecting the bulk file is at a capacity threshold, update the node graph with the bulk file containing the first piece of data in a first batch processing period and updating the node graph with the second piece of data in a second bulk file in a second batch processing period subsequent to the first batch processing period.

19. The non-transitory computer readable media of claim 18, wherein the first queue corresponds to a higher priority than the second queue, and wherein the instructions cause the one or more processors to insert the first piece of data regarding the first patient into the first queue by:

determining the first piece of data comprises protected health information of the first patient; and inserting the first piece of data into the first queue based on the determining the first piece of data comprises protected health information.

20. The non-transitory computer readable media of claim 19, wherein the instructions cause the one or more processors to determine the first piece of data comprises protected health information by using natural language processing techniques or object recognition techniques on the first piece of data.

* * * * *